US012788469B2

(12) United States Patent
Castellvi et al.

(10) Patent No.: US 12,788,469 B2
(45) Date of Patent: Nov. 10, 2026

(54) MULTI-ELECTRODE SYSTEM AND METHOD FOR DEDUCING TREATMENT EFFECT OUTCOMES

(71) Applicant: Galvanize Therapeutics, Inc., Redwood City, CA (US)

(72) Inventors: Quim Castellvi, Barcelona (ES); Robert E. Neal, II, Redwood City, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 280 days.

(21) Appl. No.: 18/472,535

(22) Filed: Sep. 22, 2023

(65) Prior Publication Data

US 2024/0032984 A1 Feb. 1, 2024

Related U.S. Application Data

(63) Continuation of application No. PCT/US2022/021888, filed on Mar. 25, 2022.

(Continued)

(51) Int. Cl.

*A61B 18/12* (2006.01)
*A61B 18/14* (2006.01)
*A61B 18/00* (2006.01)

(52) U.S. Cl.

CPC .......... *A61B 18/1206* (2013.01); *A61B 18/14* (2013.01); *A61B 2018/00845* (2013.01); *A61B 2018/00875* (2013.01)

(58) Field of Classification Search

CPC ................ A61B 18/14; A61B 18/1485; A61B 2018/00005; A61B 2018/00267;

(Continued)

(56) References Cited

U.S. PATENT DOCUMENTS 874,178 A 12/1907 Forest
4,249,541 A 2/1981 Pratt (Continued)

FOREIGN PATENT DOCUMENTS

AT 306859 B 4/1973
AU 200048007 11/2000

(Continued)

OTHER PUBLICATIONS

A. Valipour et Al. Bronchial Rheoplasty Treatment for Chronic Bronchitis Using the Rheox System, 2020 American Thoracic Society, Abstract, Aug. 5, 2020.

(Continued)

*Primary Examiner* — Michael F Peffley

(74) *Attorney, Agent, or Firm* — Greenberg Traurig, LLP; Christopher C. Bolten

(57) ABSTRACT

Described herein are monopolar treatment delivery systems, and methods for use therewith. Such a system can include an energy delivery electrode, a dispersive electrode, a reference electrode, and a generator in electrical communication with the energy delivery electrode, the dispersive electrode, and the reference electrode. The generator is configured to deliver an impedance measurement signal to target tissue using the energy delivery electrode and the dispersive electrode, while the energy delivery electrode is proximate to the target tissue and the dispersive electrode is remote from the target tissue. The generator is also configured to measure a voltage between the energy delivery electrode and the reference electrode, and to monitor impedance of the target tissue based on a current of the impedance measurement signal and the voltage between the energy delivery electrode and the reference electrode. The monitored impedance can be used, e.g., to deduce a treatment effect outcome.

22 Claims, 18 Drawing Sheets

Related U.S. Application Data

(60) Provisional application No. 63/166,145, filed on Mar. 25, 2021.

(58) Field of Classification Search
CPC A61B 2018/00357; A61B 2018/00577; A61B 2018/00613; A61B 2018/00845; A61B 2018/00875; A61B 2018/00892; A61B 2018/1253; A61B 2018/1437; A61B 2018/144
See application file for complete search history.

(56) References Cited

U.S. PATENT DOCUMENTS

| | | | |
|---|---|---|---|
| 4,822,470 | A | 4/1989 | Chang |
| 5,232,856 | A | 8/1993 | Firth |
| 5,304,120 | A | 4/1994 | Crandell et al. |
| 5,386,837 | A | 2/1995 | Sterzer |
| 5,507,724 | A | 4/1996 | Hofmann et al. |
| 5,601,588 | A | 2/1997 | Tonomura et al. |
| 5,683,384 | A | 11/1997 | Gough et al. |
| 5,704,908 | A | 1/1998 | Hofmann et al. |
| 5,833,710 | A | 11/1998 | Jacobson |
| 5,906,609 | A | 5/1999 | Assa et al. |
| 5,972,026 | A | 10/1999 | Laufer et al. |
| 6,009,347 | A | 12/1999 | Hofmann |
| 6,038,478 | A | 3/2000 | Yuen et al. |
| 6,041,252 | A | 3/2000 | Walker et al. |
| 6,078,490 | A | 6/2000 | Walters |
| 6,083,255 | A | 7/2000 | Laufer et al. |
| 6,107,699 | A | 8/2000 | Swanson |
| 6,120,493 | A | 9/2000 | Hofmann |
| 6,200,333 | B1 | 3/2001 | Laufer |
| 6,219,577 | B1 | 4/2001 | Brown, III et al. |
| 6,233,482 | B1 | 5/2001 | Hofmann et al. |
| 6,248,056 | B1 | 6/2001 | Persson |
| 6,261,831 | B1 | 7/2001 | Agee |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,299,633 | B1 | 10/2001 | Laufer |
| 6,326,177 | B1 | 12/2001 | Schoenbach et al. |
| 6,366,808 | B1 | 4/2002 | Schroeppel et al. |
| 6,411,852 | B1 | 6/2002 | Danek et al. |
| 6,488,673 | B1 | 12/2002 | Laufer et al. |
| 6,520,950 | B1 | 2/2003 | Hofmann et al. |
| 6,569,149 | B2 | 5/2003 | Dev et al. |
| 6,634,363 | B1 | 10/2003 | Danek et al. |
| 6,678,558 | B1 | 1/2004 | Dimmer et al. |
| 6,697,670 | B2 | 2/2004 | Chomenky et al. |
| 6,733,485 | B1 | 5/2004 | Whitehurst et al. |
| 6,738,663 | B2 | 5/2004 | Schroeppel et al. |
| 6,770,070 | B1 | 8/2004 | Balbierz |
| 6,795,728 | B2 | 9/2004 | Chornenky et al. |
| 6,892,099 | B2 | 5/2005 | Jaafar et al. |
| 6,994,706 | B2 | 2/2006 | Chornenky et al. |
| 7,027,869 | B2 | 4/2006 | Danek et al. |
| 7,054,685 | B2 | 5/2006 | Dimmer et al. |
| 7,104,987 | B2 | 9/2006 | Biggs et al. |
| 7,130,697 | B2 | 10/2006 | Chornenky et al. |
| 7,171,263 | B2 | 1/2007 | Darvish |
| 7,198,635 | B2 | 4/2007 | Danek et al. |
| 7,200,445 | B1 | 4/2007 | Dalbec et al. |
| 7,211,083 | B2 | 5/2007 | Chornenky et al. |
| 7,255,693 | B1 | 8/2007 | Johnston et al. |
| 7,264,002 | B2 | 9/2007 | Danek et al. |
| 7,273,055 | B2 | 9/2007 | Danek et al. |
| 7,344,533 | B2 | 3/2008 | Pearson et al. |
| 7,395,112 | B2 | 7/2008 | Keisari et al. |
| 7,412,284 | B2 | 8/2008 | Hofmann |
| 7,412,285 | B2 | 8/2008 | Schroeppel et al. |
| 7,425,212 | B1 | 9/2008 | Danek et al. |
| 7,445,618 | B2 | 11/2008 | Eggers et al. |
| 7,542,802 | B2 | 6/2009 | Danek et al. |
| 7,556,624 | B2 | 7/2009 | Laufer et al. |
| 7,565,205 | B2 | 7/2009 | Palti |
| 7,565,206 | B2 | 7/2009 | Palti |
| 7,594,925 | B2 | 9/2009 | Danek et al. |
| 7,599,745 | B2 | 10/2009 | Palti |
| 7,599,746 | B2 | 10/2009 | Palti |
| 7,620,451 | B2 | 11/2009 | Demarais et al. |
| 7,655,004 | B2 | 2/2010 | Long |
| 7,680,543 | B2 | 3/2010 | Azure |
| 7,708,768 | B2 | 5/2010 | Danek et al. |
| 7,713,740 | B2 | 5/2010 | Jaroszeski et al. |
| 7,722,606 | B2 | 5/2010 | Azure |
| 7,740,017 | B2 | 6/2010 | Danek et al. |
| 7,742,811 | B2 | 6/2010 | Schroeppel et al. |
| 7,756,583 | B2 | 7/2010 | Demarais et al. |
| 7,765,010 | B2 | 7/2010 | Chornenky et al. |
| 7,770,584 | B2 | 8/2010 | Danek et al. |
| 7,805,201 | B2 | 9/2010 | Palti |
| 7,819,908 | B2 | 10/2010 | Ingenito |
| 7,824,870 | B2 | 11/2010 | Kovalcheck et al. |
| 7,837,679 | B2 | 11/2010 | Biggs et al. |
| RE42,016 | E | 12/2010 | Chornenky et al. |
| 7,853,331 | B2 | 12/2010 | Kaplan et al. |
| 7,853,333 | B2 | 12/2010 | Demarais |
| 7,854,734 | B2 | 12/2010 | Biggs et al. |
| 7,879,610 | B1 | 2/2011 | Heller et al. |
| 7,906,124 | B2 | 3/2011 | Laufer et al. |
| 7,917,227 | B2 | 3/2011 | Palti |
| RE42,277 | E | 4/2011 | Jaafar et al. |
| 7,921,855 | B2 | 4/2011 | Danek et al. |
| 7,931,647 | B2 | 4/2011 | Wizeman et al. |
| 7,937,143 | B2 | 5/2011 | Demarais et al. |
| 7,938,123 | B2 | 5/2011 | Danek et al. |
| 7,938,824 | B2 | 5/2011 | Chornenky et al. |
| 7,949,407 | B2 | 5/2011 | Kaplan et al. |
| 7,959,628 | B2 | 6/2011 | Schaer et al. |
| 7,992,572 | B2 | 8/2011 | Danek et al. |
| 8,007,496 | B2 | 8/2011 | Rioux et al. |
| 8,014,854 | B2 | 9/2011 | Schroeppel et al. |
| 8,019,414 | B2 | 9/2011 | Palti |
| 8,024,048 | B2 | 9/2011 | Schroeppel et al. |
| 8,026,223 | B1 | 9/2011 | Heller et al. |
| RE42,835 | E | 10/2011 | Chornenky et al. |
| 8,048,067 | B2 | 11/2011 | Davalos et al. |
| RE43,009 | E | 12/2011 | Chornenky et al. |
| 8,105,324 | B2 | 1/2012 | Palanker et al. |
| 8,109,926 | B2 | 2/2012 | Azure |
| 8,114,070 | B2 | 2/2012 | Rubinsky et al. |
| 8,120,207 | B2 | 2/2012 | Sanders et al. |
| 8,131,371 | B2 | 3/2012 | Demarals et al. |
| 8,145,316 | B2 | 3/2012 | Deem et al. |
| 8,145,317 | B2 | 3/2012 | Demarais et al. |
| 8,150,519 | B2 | 4/2012 | Demarais et al. |
| 8,150,520 | B2 | 4/2012 | Demarais et al. |
| 8,161,978 | B2 | 4/2012 | Danek et al. |
| 8,181,656 | B2 | 5/2012 | Danek et al. |
| 8,221,411 | B2 | 7/2012 | Francischelli et al. |
| 8,231,603 | B2 | 7/2012 | Hobbs et al. |
| 8,235,983 | B2 | 8/2012 | Webster et al. |
| 8,244,345 | B2 | 8/2012 | Palti |
| 8,251,070 | B2 | 8/2012 | Danek et al. |
| 8,251,986 | B2 | 8/2012 | Chornenky et al. |
| 8,257,413 | B2 | 9/2012 | Danek et al. |
| 8,267,094 | B2 | 9/2012 | Danek et al. |
| 8,282,631 | B2 | 10/2012 | Davalos et al. |
| 8,292,882 | B2 | 10/2012 | Danek et al. |
| 8,298,222 | B2 | 10/2012 | Rubinsky et al. |
| 8,298,224 | B2 | 10/2012 | Danek et al. |
| 8,406,870 | B2 | 3/2013 | Palti |
| 8,425,505 | B2 | 4/2013 | Long |
| 8,428,710 | B2 | 4/2013 | Kuriyama et al. |
| 8,443,810 | B2 | 5/2013 | Danek et al. |
| 8,449,538 | B2 | 5/2013 | Long |
| 8,459,268 | B2 | 6/2013 | Danek et al. |
| 8,464,723 | B2 | 6/2013 | Danek et al. |
| 8,465,484 | B2 | 6/2013 | Davalos et al. |
| 8,465,486 | B2 | 6/2013 | Danek et al. |
| 8,480,667 | B2 | 7/2013 | Kaplan et al. |
| 8,500,713 | B2 | 8/2013 | Ferek-Petric |
| 8,504,147 | B2 | 8/2013 | Deem et al. |

(56) References Cited

U.S. PATENT DOCUMENTS 8,512,334 B2 8/2013 Nuccitelli et al.
8,521,274 B2 8/2013 Gutsol et al.
8,534,291 B2 9/2013 Danek et al.
8,540,710 B2 9/2013 Johnson et al.
8,562,588 B2 10/2013 Hobbs et al.
8,568,403 B2 10/2013 Soltesz et al.
8,579,888 B2 11/2013 Hoey et al.
8,584,681 B2 11/2013 Danek et al.
8,600,494 B2 12/2013 Schroeppel et al.
8,603,087 B2 12/2013 Rubinsky et al.
8,620,423 B2 12/2013 Demarais et al.
8,632,534 B2 1/2014 Pearson et al.
8,634,929 B2 1/2014 Chornenky et al.
8,636,726 B1 1/2014 Wells et al.
8,640,711 B2 2/2014 Danek et al.
8,647,338 B2 2/2014 Chornenky et al.
8,652,130 B2 2/2014 Kreindel
8,676,309 B2 3/2014 Deem et al.
8,721,632 B2 5/2014 Hoey et al.
8,733,367 B2 5/2014 Danek et al.
8,740,895 B2 6/2014 Mayse et al.
8,753,335 B2 6/2014 Moshe et al.
8,774,922 B2 7/2014 Zarins et al.
8,777,943 B2 7/2014 Mayse et al.
8,802,643 B1 8/2014 Heller et al.
8,814,860 B2 8/2014 Davalos et al.
8,828,945 B2 9/2014 Laufer et al.
8,888,769 B2 11/2014 Biggs et al.
8,903,488 B2 12/2014 Callas et al.
8,906,006 B2 12/2014 Chornenky et al.
8,911,430 B2 12/2014 Hoey et al.
8,911,439 B2 12/2014 Mayse et al.
8,920,413 B2 12/2014 Danek et al.
8,926,606 B2 1/2015 Davalos et al.
8,927,518 B1 1/2015 Heller et al.
8,944,071 B2 2/2015 Loomas et al.
8,968,210 B2 3/2015 Mugan et al.
8,974,417 B2 3/2015 Kimura et al.
8,992,513 B2 3/2015 Delaney
8,992,517 B2 3/2015 Davalos et al.
9,005,189 B2 4/2015 Davalos et al.
9,017,324 B2 4/2015 Mayse et al.
9,027,564 B2 5/2015 Danek et al.
9,033,976 B2 5/2015 Danek et al.
9,037,230 B2 5/2015 Goldfarb et al.
9,078,665 B2 7/2015 Moss et al.
9,095,323 B2 8/2015 Chu et al.
9,101,764 B2 8/2015 Nuccitelli et al.
9,108,052 B2 8/2015 Jarrard
9,125,666 B2 9/2015 Steinke et al.
9,144,449 B2 9/2015 Burr et al.
9,168,373 B2 10/2015 Nuccitelli et al.
9,173,704 B2 11/2015 Hobbs et al.
9,186,128 B2 11/2015 Mugan et al.
9,198,733 B2 12/2015 Neal, II et al.
9,199,091 B2 12/2015 Danek et al.
9,211,155 B2 12/2015 Fruland et al.
9,242,041 B2 1/2016 Kosik et al.
9,259,235 B2 2/2016 Chierchia et al.
9,265,563 B2 2/2016 Racz et al.
9,272,132 B2 3/2016 Laufer et al.
9,277,957 B2 3/2016 Long et al.
9,283,374 B2 3/2016 Hollett et al.
9,289,606 B2 3/2016 Paul et al.
9,295,516 B2 3/2016 Pearson et al.
9,301,796 B2 4/2016 Burr et al.
9,308,043 B2 4/2016 Zarins et al.
9,308,044 B2 4/2016 Zarins et al.
9,314,620 B2 4/2016 Long et al.
9,327,122 B2 5/2016 Zarins et al.
9,332,973 B2 5/2016 McWeeney et al.
9,339,328 B2 5/2016 Ortiz et al.
9,339,618 B2 5/2016 Deem et al.
9,358,024 B2 6/2016 Danek et al.
9,375,268 B2 6/2016 Long
9,414,881 B2 8/2016 Callas et al.
9,439,726 B2 9/2016 Zarins et al.
9,486,266 B2 11/2016 Soltesz et al.
9,510,888 B2 12/2016 Lalonde
9,526,568 B2 12/2016 Ohri et al.
9,572,619 B2 2/2017 Laufer et al.
9,598,691 B2 3/2017 Davalos
9,610,067 B2 4/2017 Sekikawa
9,610,364 B1 4/2017 Heller et al.
9,629,912 B2 4/2017 Soikum et al.
9,649,153 B2 5/2017 Mayse et al.
9,649,154 B2 5/2017 Mayse et al.
9,655,669 B2 5/2017 Palti et al.
9,656,055 B2 5/2017 Weissberg et al.
9,656,066 B2 5/2017 Nuccitelli et al.
9,668,809 B2 6/2017 Mayse et al.
9,675,406 B2 6/2017 Moss et al.
9,675,412 B2 6/2017 Mayse et al.
9,681,909 B2 6/2017 Bhargav et al.
9,700,368 B2 7/2017 Callas et al.
9,717,552 B2 8/2017 Cosman
9,724,155 B2 8/2017 Nuccitelli et al.
9,788,707 B2 10/2017 Tinkham et al.
9,789,331 B2 10/2017 Danek et al.
9,820,724 B2 11/2017 Mamiya
9,820,797 B2 11/2017 Burr et al.
9,833,617 B2 12/2017 Travers et al.
9,867,648 B2 1/2018 Mulcahey et al.
9,867,652 B2 1/2018 Sano et al.
9,877,708 B2 1/2018 McWeeney et al.
9,888,956 B2 2/2018 Model et al.
9,895,189 B2 2/2018 Pearson
9,931,161 B2 4/2018 Willis
9,931,163 B2 4/2018 Danek et al.
9,943,684 B2 4/2018 Nuccitelli et al.
9,956,391 B2 5/2018 Weissberg et al.
9,974,609 B2 5/2018 Hollett et al.
9,987,081 B1 6/2018 Bowers et al.
9,993,296 B2 6/2018 Ladtkow et al.
9,999,465 B2 6/2018 Long et al.
10,010,666 B2 7/2018 Rubinsky et al.
10,016,232 B1 7/2018 Bowers et al.
D831,199 S 10/2018 Holton et al.
D832,426 S 10/2018 Holton et al.
10,130,423 B1 11/2018 Viswanathan et al.
10,136,943 B1 11/2018 Cosman, Jr. et al.
10,143,512 B2 12/2018 Rubinsky et al.
10,143,759 B1 12/2018 Heller et al.
10,149,714 B2 12/2018 Mayse et al.
10,154,869 B2 12/2018 Onik et al.
10,154,874 B2 12/2018 Davalos et al.
10,166,071 B2 * 1/2019 Sherman ................ A61B 18/12
10,172,673 B2 1/2019 Viswanathan et al.
10,238,447 B2 3/2019 Neal, II et al.
10,245,105 B2 4/2019 Davalos et al.
10,271,893 B2 4/2019 Stewart et al.
10,292,755 B2 5/2019 Arena et al.
10,322,286 B2 6/2019 Viswanathan et al.
10,391,125 B2 8/2019 Nuccitelli et al.
10,426,847 B2 10/2019 Pierce et al.
10,448,989 B2 10/2019 Arena et al.
10,471,254 B2 11/2019 Sano et al.
10,499,980 B2 12/2019 Shuman et al.
10,639,098 B2 * 5/2020 Cosman ............. A61B 18/1206
10,694,972 B2 6/2020 Davalos et al.
10,702,337 B2 7/2020 Waldstreicher et al.
10,722,322 B2 7/2020 Vazales
10,779,887 B2 9/2020 Deem et al.
10,849,678 B2 12/2020 Onik et al.
10,874,451 B2 12/2020 Athos et al.
10,939,958 B2 3/2021 Waldstreicher et al.
10,945,714 B2 3/2021 Ralph
11,039,819 B2 6/2021 Gonzalez
11,051,871 B2 7/2021 Nuccitelli et al.
11,052,246 B2 7/2021 Stewart et al.
11,065,372 B2 7/2021 Stender et al.
11,071,530 B2 7/2021 Wang et al.
11,167,095 B2 11/2021 Ralph et al.
11,324,543 B2 5/2022 Waldstreicher et al.

(56) References Cited

U.S. PATENT DOCUMENTS 11,369,433 B2 6/2022 Waldstreicher et al.
11,382,681 B2 7/2022 Arena et al.
11,471,208 B2 10/2022 Waldstreicher et al.
11,547,851 B2 1/2023 Krimsky et al.
11,638,603 B2 5/2023 Sano et al.
11,696,797 B2 7/2023 Onik
11,723,712 B2 8/2023 Athos et al.
11,737,810 B2 8/2023 Davalos et al.
11,903,690 B2 2/2024 Davalos et al.
11,938,317 B2 3/2024 Krimsky et al.
11,952,568 B2 4/2024 Neal, II et al.
12,059,197 B2 8/2024 Davalos et al.
12,173,280 B2 12/2024 Neal, II et al.
12,178,496 B2 12/2024 Jauregui Johnston et al.
12,201,349 B2 1/2025 Pearson et al.
12,349,967 B2 7/2025 Waldstreicher et al.
12,403,305 B2 9/2025 Waldstreicher et al.
12,458,434 B2 11/2025 O'Brien et al.
2001/0008016 A1 7/2001 Kotani et al.
2001/0020166 A1 9/2001 Daly et al.
2002/0010491 A1 1/2002 Schoenbach et al.
2002/0022839 A1 2/2002 Stewart et al.
2002/0103483 A1 8/2002 Edwards
2002/0104318 A1 8/2002 Jaafar et al.
2002/0115991 A1 8/2002 Edwards
2002/0188242 A1 12/2002 Wu
2002/0198567 A1 12/2002 Keisari et al.
2003/0170898 A1 9/2003 Gundersen et al.
2003/0199050 A1 10/2003 Mangano et al.
2004/0029240 A1 2/2004 Acker
2004/0044338 A1 3/2004 Lennox et al.
2004/0047855 A1 3/2004 Ingenito
2004/0068296 A1 4/2004 Palti
2004/0102818 A1 5/2004 Hakky et al.
2004/0158288 A1 8/2004 Keisari et al.
2004/0176804 A1 9/2004 Palti
2005/0010270 A1 1/2005 Laufer
2005/0049542 A1 3/2005 Sigg et al.
2005/0096584 A1 5/2005 Ferek-Petric
2005/0096644 A1 5/2005 Hall et al.
2005/0096647 A1 5/2005 Steinke et al.
2005/0170510 A1 8/2005 Huang et al.
2005/0171523 A1 8/2005 Rubinsky et al.
2005/0171574 A1 8/2005 Rubinsky et al.
2005/0171575 A1 8/2005 Dev et al.
2005/0177150 A1 8/2005 Amoah et al.
2005/0222646 A1 10/2005 Kroll et al.
2005/0288730 A1 12/2005 Deem et al.
2006/0008808 A1 1/2006 Yang et al.
2006/0264752 A1 11/2006 Rubinsky et al.
2006/0269531 A1 11/2006 Beebe et al.
2006/0293725 A1 12/2006 Rubinsky et al.
2006/0293731 A1 12/2006 Rubinsky et al.
2007/0021803 A1 1/2007 Deem et al.
2007/0025919 A1 2/2007 Deem et al.
2007/0083239 A1 4/2007 Demarais et al.
2007/0093802 A1 4/2007 Danek et al.
2007/0106296 A1 5/2007 Laufer et al.
2007/0106348 A1 5/2007 Laufer
2007/0112349 A1 5/2007 Danek et al.
2007/0118184 A1 5/2007 Danek et al.
2007/0118190 A1 5/2007 Danek et al.
2007/0123958 A1 5/2007 Laufer
2007/0129720 A1 6/2007 Demarais et al.
2007/0156135 A1 7/2007 Rubinsky et al.
2007/0191904 A1 8/2007 Libbus et al.
2007/0239213 A1 10/2007 Palti
2008/0015571 A1 1/2008 Rubinsky et al.
2008/0071264 A1 3/2008 Azure
2008/0132884 A1 6/2008 Rubinsky et al.
2008/0132885 A1 6/2008 Rubinsky et al.
2008/0161801 A1 7/2008 Steinke et al.
2008/0195174 A1 8/2008 Walker et al.
2008/0200912 A1 8/2008 Long
2008/0231337 A1 9/2008 Krishnaswamy et al.
2008/0269586 A1 10/2008 Rubinsky et al.
2008/0306570 A1 12/2008 Rezai et al.
2008/0319372 A1 12/2008 Palti et al.
2009/0043301 A1 2/2009 Jarrard et al.
2009/0069797 A1 3/2009 Danek et al.
2009/0118726 A1 5/2009 Auth et al.
2009/0157002 A1 6/2009 Dumot et al.
2009/0192504 A1 7/2009 Askew
2009/0192505 A1 7/2009 Askew et al.
2009/0192508 A1 7/2009 Laufer et al.
2009/0247933 A1 10/2009 Maor et al.
2009/0281477 A1 11/2009 Mikus et al.
2009/0292342 A1 11/2009 Rubinsky et al.
2009/0306644 A1 12/2009 Mayse et al.
2009/0318914 A1 12/2009 Utley et al.
2010/0004623 A1 1/2010 Hamilton, Jr. et al.
2010/0023004 A1 1/2010 Francischelli et al.
2010/0121270 A1 5/2010 Gunday et al.
2010/0130975 A1 5/2010 Long
2010/0147701 A1 6/2010 Field
2010/0152725 A1 6/2010 Pearson et al.
2010/0160906 A1 6/2010 Jarrard
2010/0179530 A1 7/2010 Long et al.
2010/0204688 A1 8/2010 Hoey et al.
2010/0228248 A1 9/2010 Griffin
2010/0240995 A1 9/2010 Nuccitelli et al.
2010/0256628 A1 10/2010 Pearson et al.
2010/0256630 A1 10/2010 Hamilton, Jr. et al.
2010/0261994 A1 10/2010 Davalos et al.
2010/0274236 A1 10/2010 Krimsky
2010/0324616 A1 12/2010 Livnat et al.
2011/0105726 A1 5/2011 Rosen et al.
2011/0112527 A1 5/2011 Hamilton, Jr. et al.
2011/0118732 A1 5/2011 Rubinsky et al.
2011/0152855 A1 6/2011 Mayse et al.
2011/0166565 A1 7/2011 Wizeman et al.
2011/0190662 A1 8/2011 McWeeney
2011/0196288 A1 8/2011 Kaplan et al.
2011/0202052 A1 8/2011 Gelbart et al.
2011/0208166 A1 8/2011 Dumot et al.
2011/0288545 A1 11/2011 Beebe et al.
2012/0098351 A1 4/2012 Ross
2012/0109122 A1 5/2012 Arena et al.
2012/0143120 A1 6/2012 Goldfarb et al.
2012/0150172 A1 6/2012 Ortiz et al.
2012/0197243 A1 8/2012 Sherman et al.
2012/0220998 A1 8/2012 Long et al.
2012/0220999 A1 8/2012 Long
2012/0226101 A1 9/2012 Tinkham et al.
2012/0226271 A1 9/2012 Callas et al.
2012/0277741 A1 11/2012 Davalos et al.
2012/0310237 A1 12/2012 Swanson
2012/0315704 A1 12/2012 Beebe et al.
2012/0330299 A1 12/2012 Webster et al.
2012/0330306 A1 12/2012 Long et al.
2013/0006144 A1 1/2013 Clancy et al.
2013/0023873 A1 1/2013 Danek et al.
2013/0030425 A1 1/2013 Stewart et al.
2013/0030430 A1 1/2013 Stewart et al.
2013/0035747 A1 2/2013 Danek et al.
2013/0184702 A1 7/2013 Neal, II et al.
2013/0196441 A1 8/2013 Rubinsky et al.
2013/0211402 A1 8/2013 Danek et al.
2013/0218158 A1 8/2013 Danek et al.
2013/0225996 A1 8/2013 Dillard et al.
2013/0226167 A1 8/2013 Kaplan et al.
2013/0253415 A1 9/2013 Sano et al.
2013/0261389 A1 10/2013 Long
2013/0261683 A1 10/2013 Soikum et al.
2014/0018789 A1 1/2014 Kaplan et al.
2014/0018790 A1 1/2014 Kaplan et al.
2014/0025063 A1 1/2014 Kaplan et al.
2014/0039489 A1 2/2014 Davalos et al.
2014/0039491 A1 2/2014 Bakos et al.
2014/0046322 A1 2/2014 Callas et al.
2014/0052126 A1 2/2014 Long et al.
2014/0058294 A1 2/2014 Gross et al.
2014/0066913 A1 3/2014 Sherman
2014/0074078 A1 3/2014 Kumar et al.

(56) References Cited

U.S. PATENT DOCUMENTS

| | | | |
|---|---|---|---|
| 2014/0081263 | A1 | 3/2014 | Mesallum |
| 2014/0107478 | A1 | 4/2014 | Seward et al. |
| 2014/0114378 | A1 | 4/2014 | Danek et al. |
| 2014/0121663 | A1 | 5/2014 | Pearson et al. |
| 2014/0128949 | A1 | 5/2014 | Hollett et al. |
| 2014/0148635 | A1 | 5/2014 | Danek et al. |
| 2014/0296844 | A1 | 10/2014 | Kevin et al. |
| 2014/0324036 | A1 | 10/2014 | Sachs et al. |
| 2014/0324037 | A1 | 10/2014 | Hoey et al. |
| 2014/0330332 | A1 | 11/2014 | Danek et al. |
| 2014/0341801 | A1 | 11/2014 | Laufer et al. |
| 2014/0378964 | A1 | 12/2014 | Pearson |
| 2015/0005766 | A1 | 1/2015 | Rioux et al. |
| 2015/0025605 | A1 | 1/2015 | Kaplan et al. |
| 2015/0038959 | A1 | 2/2015 | Biggs et al. |
| 2015/0039059 | A1 | 2/2015 | Mokelke et al. |
| 2015/0045788 | A1 | 2/2015 | Litscher et al. |
| 2015/0066005 | A1 | 3/2015 | Fan et al. |
| 2015/0066108 | A1 | 3/2015 | Shi et al. |
| 2015/0080884 | A1 | 3/2015 | Zarins et al. |
| 2015/0088120 | A1 | 3/2015 | Garcia et al. |
| 2015/0105775 | A1 | 4/2015 | Wizeman et al. |
| 2015/0112321 | A1 | 4/2015 | Cadouri |
| 2015/0119879 | A1 | 4/2015 | Jameson et al. |
| 2015/0141984 | A1 | 5/2015 | Loomas et al. |
| 2015/0150618 | A1 | 6/2015 | Onik et al. |
| 2015/0164584 | A1 | 6/2015 | Davalos et al. |
| 2015/0173943 | A1 | 6/2015 | Loomas et al. |
| 2015/0182282 | A1 | 7/2015 | Zemel et al. |
| 2015/0182560 | A1 | 7/2015 | Calle et al. |
| 2015/0201996 | A1 | 7/2015 | Rubinsky et al. |
| 2015/0223879 | A1 | 8/2015 | Danek et al. |
| 2015/0230855 | A1 | 8/2015 | Chornenky et al. |
| 2015/0258352 | A1 | 9/2015 | Lin et al. |
| 2015/0289923 | A1 | 10/2015 | Davalos et al. |
| 2015/0305794 | A1 | 10/2015 | Danek et al. |
| 2015/0313664 | A1 | 11/2015 | Jarrard |
| 2015/0320478 | A1 | 11/2015 | Cosman, Jr. et al. |
| 2015/0320479 | A1 | 11/2015 | Cosman, Jr. et al. |
| 2015/0320999 | A1 | 11/2015 | Nuccitelli et al. |
| 2015/0327944 | A1 | 11/2015 | Neal, II et al. |
| 2015/0342669 | A1 | 12/2015 | Flanagan et al. |
| 2016/0000499 | A1 | 1/2016 | Lennox et al. |
| 2016/0008016 | A1 | 1/2016 | Cioanta et al. |
| 2016/0008066 | A1 | 1/2016 | Kaplan et al. |
| 2016/0022349 | A1 | 1/2016 | Woloszko et al. |
| 2016/0030014 | A1 | 2/2016 | McWeeney et al. |
| 2016/0030016 | A1 | 2/2016 | McWeeney et al. |
| 2016/0038230 | A1 | 2/2016 | Danek et al. |
| 2016/0058493 | A1 | 3/2016 | Neal, II et al. |
| 2016/0066977 | A1 | 3/2016 | Neal, II et al. |
| 2016/0066990 | A1 | 3/2016 | Kaplan et al. |
| 2016/0074091 | A1 | 3/2016 | Amoah et al. |
| 2016/0081745 | A1 | 3/2016 | Rajagopalan et al. |
| 2016/0113703 | A1 | 4/2016 | Danek et al. |
| 2016/0128767 | A1 | 5/2016 | Azamian et al. |
| 2016/0166310 | A1 | 6/2016 | Stewart et al. |
| 2016/0199131 | A1 | 7/2016 | Allison et al. |
| 2016/0206370 | A1 | 7/2016 | Fruland et al. |
| 2016/0235974 | A1 | 8/2016 | Holochwost et al. |
| 2016/0262601 | A1 | 9/2016 | Viebach et al. |
| 2016/0262795 | A1 | 9/2016 | Urbanski et al. |
| 2016/0287314 | A1 | 10/2016 | Arena et al. |
| 2016/0303293 | A1 | 10/2016 | Doyle et al. |
| 2016/0310211 | A1 | 10/2016 | Long |
| 2016/0324573 | A1 | 11/2016 | Mickelson et al. |
| 2016/0331441 | A1 | 11/2016 | Konings |
| 2016/0338758 | A9 | 11/2016 | Davalos et al. |
| 2016/0354142 | A1 | 12/2016 | Pearson et al. |
| 2016/0354145 | A1 | 12/2016 | Stern et al. |
| 2016/0361109 | A1 | 12/2016 | Weaver et al. |
| 2016/0367310 | A1 | 12/2016 | Onik et al. |
| 2017/0000584 | A1 | 1/2017 | Blanco et al. |
| 2017/0035499 | A1 | 2/2017 | Stewart et al. |
| 2017/0049513 | A1* | 2/2017 | Cosman, Jr. ........... A61B 18/18 |
| 2017/0065330 | A1 | 3/2017 | Mickelsen et al. |
| 2017/0065339 | A1 | 3/2017 | Mickelsen |
| 2017/0065340 | A1 | 3/2017 | Long |
| 2017/0065343 | A1 | 3/2017 | Mickelsen |
| 2017/0087224 | A1 | 3/2017 | Quake |
| 2017/0105763 | A1 | 4/2017 | Karve et al. |
| 2017/0105793 | A1 | 4/2017 | Cao et al. |
| 2017/0117603 | A1 | 4/2017 | Kreis et al. |
| 2017/0119465 | A1 | 5/2017 | Long et al. |
| 2017/0135723 | A1 | 5/2017 | Zarembinski |
| 2017/0156783 | A1 | 6/2017 | McKernon et al. |
| 2017/0189097 | A1 | 7/2017 | Viswanathan et al. |
| 2017/0189579 | A1 | 7/2017 | Davalos |
| 2017/0215939 | A1 | 8/2017 | Palti et al. |
| 2017/0215953 | A1 | 8/2017 | Long et al. |
| 2017/0216353 | A1 | 8/2017 | Nuccitelli et al. |
| 2017/0216585 | A1 | 8/2017 | Goldfarb et al. |
| 2017/0224363 | A1 | 8/2017 | Watanabe et al. |
| 2017/0239480 | A1 | 8/2017 | Zarins et al. |
| 2017/0246455 | A1 | 8/2017 | Athos et al. |
| 2017/0252090 | A1 | 9/2017 | Smith et al. |
| 2017/0266283 | A1 | 9/2017 | Soikum et al. |
| 2017/0266438 | A1 | 9/2017 | Sano et al. |
| 2017/0281934 | A1 | 10/2017 | Giladi et al. |
| 2017/0304002 | A1 | 10/2017 | Beebe et al. |
| 2017/0311789 | A1 | 11/2017 | Mulcahey et al. |
| 2017/0312021 | A1 | 11/2017 | Pilcher et al. |
| 2017/0319843 | A1 | 11/2017 | Beebe et al. |
| 2017/0319851 | A1 | 11/2017 | Athos et al. |
| 2017/0325894 | A1 | 11/2017 | Krimsky |
| 2017/0326361 | A1 | 11/2017 | Kreis et al. |
| 2017/0333104 | A1 | 11/2017 | Forde et al. |
| 2017/0333109 | A1 | 11/2017 | Gilbert |
| 2017/0333112 | A1 | 11/2017 | Nuccitelli et al. |
| 2017/0360326 | A1 | 12/2017 | Davalos et al. |
| 2018/0000895 | A1 | 1/2018 | Pierce et al. |
| 2018/0001056 | A1 | 1/2018 | Leeflang et al. |
| 2018/0008127 | A1 | 1/2018 | Tinkham et al. |
| 2018/0014868 | A1 | 1/2018 | O'Connor et al. |
| 2018/0028250 | A1 | 2/2018 | O'Connor |
| 2018/0028267 | A1 | 2/2018 | Onik et al. |
| 2018/0036058 | A1 | 2/2018 | Fan et al. |
| 2018/0042655 | A1 | 2/2018 | Burr et al. |
| 2018/0042674 | A1 | 2/2018 | Mickelsen |
| 2018/0042675 | A1 | 2/2018 | Long |
| 2018/0043153 | A1 | 2/2018 | Viswanathan et al. |
| 2018/0064488 | A1 | 3/2018 | Long et al. |
| 2018/0071014 | A1 | 3/2018 | Neal et al. |
| 2018/0078755 | A1 | 3/2018 | Kreis et al. |
| 2018/0085160 | A1 | 3/2018 | Viswanathan et al. |
| 2018/0085575 | A1 | 3/2018 | Travers et al. |
| 2018/0104486 | A1 | 4/2018 | Yoon et al. |
| 2018/0110557 | A1 | 4/2018 | Muratori et al. |
| 2018/0110978 | A1 | 4/2018 | Beebe et al. |
| 2018/0125565 | A1 | 5/2018 | Sano et al. |
| 2018/0132922 | A1 | 5/2018 | Neal, II |
| 2018/0153467 | A1 | 6/2018 | Lichtenstein et al. |
| 2018/0153937 | A1 | 6/2018 | Nuccitelli et al. |
| 2018/0154142 | A1 | 6/2018 | Guo et al. |
| 2018/0193082 | A1 | 7/2018 | Rubinsky et al. |
| 2018/0193088 | A1 | 7/2018 | Sutton et al. |
| 2018/0200510 | A1 | 7/2018 | Nuccitelli et al. |
| 2018/0221078 | A1 | 8/2018 | Howard et al. |
| 2018/0263685 | A1 | 9/2018 | Onik et al. |
| 2018/0289954 | A1 | 10/2018 | Hebb et al. |
| 2018/0303543 | A1 | 10/2018 | Stewart et al. |
| 2018/0311497 | A1 | 11/2018 | Viswanathan et al. |
| 2018/0344378 | A1 | 12/2018 | Wolf et al. |
| 2018/0360531 | A1 | 12/2018 | Holmes, Jr. et al. |
| 2019/0022333 | A1 | 1/2019 | Baillargeon et al. |
| 2019/0030328 | A1 | 1/2019 | Stewart et al. |
| 2019/0038895 | A1 | 2/2019 | Pianca et al. |
| 2019/0046791 | A1 | 2/2019 | Ebbers et al. |
| 2019/0059864 | A1 | 2/2019 | Gonzalez |
| 2019/0069950 | A1 | 3/2019 | Viswanathan et al. |
| 2019/0083169 | A1 | 3/2019 | Single et al. |
| 2019/0099214 | A1 | 4/2019 | Rubinsky et al. |
| 2019/0105408 | A1 | 4/2019 | Heller et al. |
| 2019/0117963 | A1 | 4/2019 | Travers et al. |

(56) References Cited

U.S. PATENT DOCUMENTS

| | | | |
|---|---|---|---|
| 2019/0117969 | A1 | 4/2019 | Schmidt et al. |
| 2019/0126037 | A1 | 5/2019 | Ivorra Cano |
| 2019/0151015 | A1 | 5/2019 | Viswanathan et al. |
| 2019/0160283 | A1 | 5/2019 | Nuccitelli et al. |
| 2019/0201089 | A1 | 7/2019 | Waldstreicher et al. |
| 2019/0216899 | A1 | 7/2019 | Bright |
| 2019/0223938 | A1 | 7/2019 | Arena et al. |
| 2019/0223943 | A1 | 7/2019 | Forsyth et al. |
| 2019/0232048 | A1 | 8/2019 | Latouche et al. |
| 2019/0239949 | A1 | 8/2019 | Nuccitelli et al. |
| 2019/0254735 | A1 | 8/2019 | Stewart et al. |
| 2019/0269826 | A1 | 9/2019 | Peyman |
| 2019/0269912 | A1 | 9/2019 | Viswanathan et al. |
| 2019/0275260 | A1 | 9/2019 | Ralph et al. |
| 2019/0282294 | A1 | 9/2019 | Davalos et al. |
| 2019/0299019 | A1 | 10/2019 | Chornenky et al. |
| 2019/0307781 | A1 | 10/2019 | Krex et al. |
| 2019/0328445 | A1 | 10/2019 | Sano et al. |
| 2019/0350971 | A1 | 11/2019 | Nuccitelli et al. |
| 2019/0351224 | A1 | 11/2019 | Sano et al. |
| 2019/0365362 | A1 | 12/2019 | Ralph |
| 2020/0000938 | A1 | 1/2020 | Pierce et al. |
| 2020/0009377 | A1 | 1/2020 | Chang et al. |
| 2020/0016067 | A1 | 1/2020 | Gotlib et al. |
| 2020/0038093 | A1 | 2/2020 | Onik |
| 2020/0046423 | A1 | 2/2020 | Viswanathan et al. |
| 2020/0046967 | A1 | 2/2020 | Ivey et al. |
| 2020/0060754 | A1 | 2/2020 | Shuman et al. |
| 2020/0060755 | A1 | 2/2020 | Shuman et al. |
| 2020/0078047 | A1 | 3/2020 | Lambe et al. |
| 2020/0129228 | A1 | 4/2020 | Henkes et al. |
| 2020/0260987 | A1 | 8/2020 | Davalos et al. |
| 2020/0275973 | A1 | 9/2020 | O'Brien et al. |
| 2020/0298008 | A1 | 9/2020 | Asirvatham |
| 2020/0323583 | A1 | 10/2020 | Qiao |
| 2020/0398048 | A1 | 12/2020 | Krimsky et al. |
| 2021/0022794 | A1 | 1/2021 | Viswanathan |
| 2021/0023362 | A1* | 1/2021 | Lorenzo ................ A61B 18/12 |
| 2021/0038280 | A1 | 2/2021 | Pikramenos |
| 2021/0052882 | A1 | 2/2021 | Wasson et al. |
| 2021/0085777 | A1 | 3/2021 | Steinmetz et al. |
| 2021/0137410 | A1 | 5/2021 | O'Brien et al. |
| 2021/0146126 | A1 | 5/2021 | Waldstreicher et al. |
| 2021/0161582 | A1 | 6/2021 | Byrd et al. |
| 2021/0236815 | A1 | 8/2021 | Waldstreicher et al. |
| 2021/0236816 | A1 | 8/2021 | Waldstreicher et al. |
| 2021/0315639 | A1 | 10/2021 | Manucherhabadi et al. |
| 2021/0393327 | A1 | 12/2021 | Eyster et al. |
| 2022/0054188 | A1 | 2/2022 | Palushi et al. |
| 2022/0104875 | A1 | 4/2022 | Gleiman et al. |
| 2022/0161027 | A1 | 5/2022 | Aycock et al. |
| 2022/0233237 | A1 | 7/2022 | Adams et al. |
| 2022/0249157 | A1 | 8/2022 | Viswanathan et al. |
| 2022/0330886 | A1 | 10/2022 | Varadan et al. |
| 2022/0387095 | A1 | 12/2022 | Neal, II et al. |
| 2022/0395323 | A1 | 12/2022 | Waldstreicher et al. |
| 2023/0082389 | A1 | 3/2023 | Waldstreicher et al. |
| 2023/0149706 | A1 | 5/2023 | Krimsky et al. |
| 2023/0165629 | A1 | 6/2023 | Tehrani et al. |
| 2023/0172650 | A1 | 6/2023 | Castellvi et al. |
| 2023/0240746 | A1 | 8/2023 | Gundert et al. |
| 2023/0248414 | A1 | 8/2023 | Sano et al. |
| 2023/0405313 | A1 | 12/2023 | Pastori et al. |
| 2024/0032984 | A1 | 2/2024 | Castellvi et al. |
| 2024/0173557 | A1 | 5/2024 | Neal, II et al. |
| 2024/0180878 | A1 | 6/2024 | Spera |
| 2024/0216038 | A1 | 7/2024 | Girouard et al. |
| 2024/0277245 | A1 | 8/2024 | Davalos et al. |
| 2024/0350185 | A1 | 10/2024 | O'Brien et al. |
| 2024/0350187 | A1 | 10/2024 | Waldstreicher et al. |
| 2024/0390672 | A1 | 11/2024 | Neal et al. |
| 2025/0032787 | A1 | 1/2025 | Krimsky et al. |
| 2025/0040985 | A1 | 2/2025 | Girouard et al. |
| 2025/0064510 | A1 | 2/2025 | Waldstreicher et al. |
| 2025/0213299 | A1 | 7/2025 | Nafie et al. |
| 2025/0261991 | A1 | 8/2025 | O'Brien et al. |
| 2025/0295442 | A1 | 9/2025 | Darwish et al. |
| 2026/0014371 | A1 | 1/2026 | Krimsky et al. |

FOREIGN PATENT DOCUMENTS

| | | | |
|---|---|---|---|
| AU | 2004235684 | A1 | 1/2005 |
| AU | 2015355241 | A1 | 6/2017 |
| AU | 2016246146 | A1 | 10/2017 |
| AU | 2020200688 | B2 | 7/2021 |
| CA | 2370223 | A1 | 10/2000 |
| CA | 2981867 | A1 | 10/2016 |
| CN | 1867299 | A | 11/2006 |
| CN | 101198287 | A | 6/2008 |
| CN | 101426551 | A | 5/2009 |
| CN | 101553180 | A | 10/2009 |
| CN | 101909649 | A | 12/2010 |
| CN | 102014779 | A | 4/2011 |
| CN | 102105115 | A | 6/2011 |
| CN | 102421386 | A | 4/2012 |
| CN | 102725021 | A | 10/2012 |
| CN | 103027745 | A | 4/2013 |
| CN | 103252016 | A | 8/2013 |
| CN | 103281978 | A | 9/2013 |
| CN | 103313671 | A | 9/2013 |
| CN | 103582463 | A | 2/2014 |
| CN | 103750899 | A | 4/2014 |
| CN | 103781433 | A | 5/2014 |
| CN | 103796603 | A | 5/2014 |
| CN | 104080418 | A | 10/2014 |
| CN | 104363849 | A | 2/2015 |
| CN | 104470454 | A | 3/2015 |
| CN | 104602634 | A | 5/2015 |
| CN | 104602754 | A | 5/2015 |
| CN | 104703557 | A | 6/2015 |
| CN | 105073051 | A | 11/2015 |
| CN | 105939686 | A | 9/2016 |
| CN | 107194119 | A | 9/2017 |
| CN | 107205772 | A | 9/2017 |
| CN | 107921258 | A | 4/2018 |
| CN | 108024803 | A | 5/2018 |
| CN | 108778172 | A | 11/2018 |
| CN | 108778173 | A | 11/2018 |
| CN | 109788979 | A | 5/2019 |
| CN | 110573104 | A | 12/2019 |
| CN | 113558744 | A | 10/2021 |
| CO | 2017010662 | A2 | 3/2018 |
| DE | 60023283 | T2 | 7/2006 |
| DK | 0987989 | T3 | 10/2006 |
| EP | 1173103 | A2 | 1/2002 |
| EP | 0935482 | B1 | 5/2005 |
| EP | 1173103 | B1 | 10/2005 |
| EP | 1804905 | A1 | 7/2007 |
| EP | 1991303 | A2 | 11/2008 |
| EP | 2170198 | A1 | 4/2010 |
| EP | 2317951 | A1 | 5/2011 |
| EP | 2413833 | A1 | 2/2012 |
| EP | 2488251 | A2 | 8/2012 |
| EP | 2642937 | A2 | 10/2013 |
| EP | 2661236 | A1 | 11/2013 |
| EP | 2736432 | A1 | 6/2014 |
| EP | 2762195 | A2 | 8/2014 |
| EP | 2777579 | A1 | 9/2014 |
| EP | 2170198 | B1 | 4/2015 |
| EP | 1648555 | B1 | 9/2015 |
| EP | 2957248 | A1 | 12/2015 |
| EP | 1804905 | B1 | 2/2016 |
| EP | 2736432 | B1 | 3/2016 |
| EP | 3003461 | A2 | 4/2016 |
| EP | 2661236 | B1 | 8/2016 |
| EP | 3091925 | A1 | 11/2016 |
| EP | 3113605 | A1 | 1/2017 |
| EP | 3142584 | A1 | 3/2017 |
| EP | 3143124 | A1 | 3/2017 |
| EP | 3154464 | A1 | 4/2017 |
| EP | 3003470 | B1 | 8/2017 |
| EP | 3226794 | A1 | 10/2017 |
| EP | 3282953 | A1 | 2/2018 |
| EP | 3290082 | A2 | 3/2018 |

(56) References Cited

FOREIGN PATENT DOCUMENTS

| | | | |
|---|---|---|---|
| EP | 3139997 | B1 | 9/2018 |
| EP | 3113605 | B1 | 10/2018 |
| EP | 3399931 | A1 | 11/2018 |
| EP | 3399933 | A1 | 11/2018 |
| EP | 3154463 | B1 | 3/2019 |
| EP | 3471631 | A1 | 4/2019 |
| EP | 2994045 | B1 | 5/2019 |
| EP | 3003461 | B1 | 5/2019 |
| EP | 3091921 | B1 | 6/2019 |
| EP | 3456278 | A3 | 6/2019 |
| EP | 3495018 | A1 | 6/2019 |
| EP | 3206613 | B1 | 7/2019 |
| EP | 3569144 | A1 | 11/2019 |
| ES | 2246853 | T3 | 3/2006 |
| ES | 2361460 | T3 | 6/2011 |
| IN | 200601622 | | 5/2007 |
| JP | H09285182 | A | 10/1997 |
| JP | 2001103741 | A | 4/2001 |
| JP | 2001506157 | A | 5/2001 |
| JP | 2002065626 | A | 3/2002 |
| JP | 2002541905 | A | 12/2002 |
| JP | 2003529401 | A | 10/2003 |
| JP | 2004516867 | A | 6/2004 |
| JP | 2006320176 | A | 11/2006 |
| JP | 2007504910 | A | 3/2007 |
| JP | 4242436 | B2 | 3/2009 |
| JP | 4243436 | B2 | 3/2009 |
| JP | 2010509032 | A | 3/2010 |
| JP | 2011519699 | A | 7/2011 |
| JP | 2011524785 | A | 9/2011 |
| JP | 2012515018 | A | 7/2012 |
| JP | 2013543745 | A | 12/2013 |
| JP | 2015128596 | A | 7/2015 |
| JP | 2015524732 | A | 8/2015 |
| JP | 2016195826 | A | 11/2016 |
| JP | 2017518805 | A | 7/2017 |
| JP | 2017529169 | A | 10/2017 |
| JP | 2019500170 | A | 1/2019 |
| JP | 2019524396 | A | 9/2019 |
| JP | 2020518335 | A | 6/2020 |
| JP | 2021500153 | A | 1/2021 |
| JP | 2021508533 | A | 3/2021 |
| JP | 2023536906 | A | 8/2023 |
| PT | 987989 | E | 11/2006 |
| WO | WO-9814238 | A1 | 4/1998 |
| WO | WO-9906101 | A1 | 2/1999 |
| WO | WO-2000062699 | A2 | 10/2000 |
| WO | WO-0110319 | A1 | 2/2001 |
| WO | WO-2001055294 | A1 | 8/2001 |
| WO | WO-2002032333 | A1 | 4/2002 |
| WO | WO-02098501 | A2 | 12/2002 |
| WO | WO-03047684 | A2 | 6/2003 |
| WO | WO-2004037341 | A2 | 5/2004 |
| WO | WO-2004110371 | A2 | 12/2004 |
| WO | WO-2005044371 | A1 | 5/2005 |
| WO | WO-2005065284 | A2 | 7/2005 |
| WO | WO-2005065284 | A3 | 11/2005 |
| WO | WO-2005115535 | A2 | 12/2005 |
| WO | WO-2005032646 | A3 | 4/2006 |
| WO | WO-2006036706 | A1 | 4/2006 |
| WO | WO-2006052940 | A2 | 5/2006 |
| WO | WO-2006085150 | A2 | 8/2006 |
| WO | WO-2006116198 | A2 | 11/2006 |
| WO | WO-2006116608 | A2 | 11/2006 |
| WO | WO-2006131816 | A2 | 12/2006 |
| WO | WO-2007001747 | A2 | 1/2007 |
| WO | WO-2007001751 | A1 | 1/2007 |
| WO | WO-2007039799 | A3 | 7/2007 |
| WO | WO-2007100727 | A2 | 9/2007 |
| WO | WO-2007103070 | A2 | 9/2007 |
| WO | WO-2008034100 | A2 | 3/2008 |
| WO | WO-2008063195 | A1 | 5/2008 |
| WO | WO-2008087489 | A2 | 7/2008 |
| WO | WO-2009009398 | A1 | 1/2009 |
| WO | WO-2009137800 | A2 | 11/2009 |
| WO | WO-2009137819 | A1 | 11/2009 |
| WO | WO-2009154654 | A1 | 12/2009 |
| WO | WO-2010014480 | A1 | 2/2010 |
| WO | WO-2010022275 | A1 | 2/2010 |
| WO | WO-2010080974 | A1 | 7/2010 |
| WO | WO-2010093692 | A2 | 8/2010 |
| WO | WO-2010107947 | A1 | 9/2010 |
| WO | WO-2010117806 | A1 | 10/2010 |
| WO | WO-2010118387 | A1 | 10/2010 |
| WO | WO-2010141417 | A2 | 12/2010 |
| WO | WO-2010151277 | A1 | 12/2010 |
| WO | WO-2011047387 | A2 | 4/2011 |
| WO | WO-2011135294 | A1 | 11/2011 |
| WO | WO-2012071526 | A2 | 5/2012 |
| WO | WO-2012088149 | A2 | 6/2012 |
| WO | WO-2012118659 | A1 | 9/2012 |
| WO | WO-2013052501 | A1 | 4/2013 |
| WO | WO-2014025394 | A1 | 2/2014 |
| WO | WO-2014105964 | A1 | 7/2014 |
| WO | WO-2014181167 | A1 | 11/2014 |
| WO | WO-2014197240 | A2 | 12/2014 |
| WO | WO-2014197632 | A2 | 12/2014 |
| WO | WO-2014204978 | A1 | 12/2014 |
| WO | WO-2015085162 | A1 | 6/2015 |
| WO | WO-2015103530 | A1 | 7/2015 |
| WO | WO-2015103574 | A1 | 7/2015 |
| WO | WO-2015171921 | A2 | 11/2015 |
| WO | WO-2015175570 | A1 | 11/2015 |
| WO | WO-2015192018 | A1 | 12/2015 |
| WO | WO-2015192027 | A1 | 12/2015 |
| WO | WO-2016014264 | A1 | 1/2016 |
| WO | WO-2016036891 | A1 | 3/2016 |
| WO | WO-2016060983 | A1 | 4/2016 |
| WO | WO-2016061002 | A1 | 4/2016 |
| WO | WO-2016089781 | A1 | 6/2016 |
| WO | WO-2016100325 | A1 | 6/2016 |
| WO | WO-2016112359 | A1 | 7/2016 |
| WO | WO-2016123608 | A2 | 8/2016 |
| WO | WO-2016126778 | A1 | 8/2016 |
| WO | WO-2016149575 | A1 | 9/2016 |
| WO | WO-2016154473 | A1 | 9/2016 |
| WO | WO-2016164930 | A1 | 10/2016 |
| WO | WO-2016178697 | A1 | 11/2016 |
| WO | WO-2016179712 | A1 | 11/2016 |
| WO | WO-2016180934 | A1 | 11/2016 |
| WO | WO-2016201264 | A1 | 12/2016 |
| WO | WO-2017024123 | A1 | 2/2017 |
| WO | WO-2017109261 | A1 | 6/2017 |
| WO | WO-2017114001 | A1 | 7/2017 |
| WO | WO-2017119934 | A1 | 7/2017 |
| WO | WO-2017120169 | A1 | 7/2017 |
| WO | WO-2017151260 | A1 | 9/2017 |
| WO | WO-2017173089 | A1 | 10/2017 |
| WO | WO-2017175116 | A1 | 10/2017 |
| WO | WO-2017200954 | A1 | 11/2017 |
| WO | WO-2017201394 | A1 | 11/2017 |
| WO | WO-2017218734 | A1 | 12/2017 |
| WO | WO-2018005511 | A1 | 1/2018 |
| WO | WO-2018010659 | A1 | 1/2018 |
| WO | WO-2018026985 | A1 | 2/2018 |
| WO | WO-2018065806 | A1 | 4/2018 |
| WO | WO-2018067999 | A1 | 4/2018 |
| WO | WO-2018075946 | A1 | 4/2018 |
| WO | WO-2018106672 | A1 | 6/2018 |
| WO | WO-2018187244 | A2 | 10/2018 |
| WO | WO-2018200800 | A1 | 11/2018 |
| WO | WO-2018201037 | A1 | 11/2018 |
| WO | WO-2019032474 | A1 | 2/2019 |
| WO | WO-2019055512 | A1 | 3/2019 |
| WO | WO-2019084011 | A1 | 5/2019 |
| WO | WO-2019095604 | A1 | 5/2019 |
| WO | WO-2019100016 | A1 | 5/2019 |
| WO | WO-2019108540 | A1 | 6/2019 |
| WO | WO-2019133606 | A1 | 7/2019 |
| WO | WO-2019133608 | A1 | 7/2019 |
| WO | WO-2019157359 | A1 | 8/2019 |
| WO | WO-2019178500 | A1 | 9/2019 |
| WO | WO-2019197973 | A1 | 10/2019 |
| WO | WO-2020005186 | A2 | 1/2020 |

(56) References Cited

FOREIGN PATENT DOCUMENTS

| | | | |
|---|---|---|---|
| WO | WO-2020010188 | A1 | 1/2020 |
| WO | WO-2020018662 | A1 | 1/2020 |
| WO | WO-2020061192 | A1 | 3/2020 |
| WO | WO-2020118383 | A1 | 6/2020 |
| WO | WO-2020150709 | A1 | 7/2020 |
| WO | WO-2020215007 | A1 | 10/2020 |
| WO | WO-2021011733 | | 1/2021 |
| WO | WO-2021108292 | A1 | 6/2021 |
| WO | WO-2021127558 | A1 | 6/2021 |
| WO | WO-2021207385 | A1 | 10/2021 |
| WO | WO-2022031797 | A1 | 2/2022 |
| WO | WO-2022204479 | A1 | 9/2022 |
| WO | WO-2022260723 | A1 | 12/2022 |
| WO | WO-2022261418 | A1 | 12/2022 |
| WO | WO-2023044124 | A1 | 3/2023 |
| WO | WO-2023172773 | A1 | 9/2023 |
| WO | WO-2023212250 | A1 | 11/2023 |
| WO | WO-2023220419 | A1 | 11/2023 |
| WO | WO-2024196823 | A2 | 9/2024 |
| WO | WO-2024254966 | A1 | 12/2024 |
| WO | WO-2025043024 | A2 | 2/2025 |
| WO | WO-2025081663 | A1 | 4/2025 |
| WO | WO-2025235871 | A1 | 11/2025 |

OTHER PUBLICATIONS

A. Valipour, et Al. *First-in-Human Results of Bronchial Rheoplasty: An Endobronchial Treatment for Chronic Bronchitis* (*CB*), Epidemiology and Therapy, Mini Symposium, May 22, 2019, Abstract.

Appelbaum et al., US Findings after Irreversible Electroporation Ablation: Radiologic-Pathologic Correlation, Radiology: vol. 262: No. 1—Jan. 2012.

Arschang Valipour et al. *Bronchial Rheoplasty for Treatment of Chronic Bronchitis*, American Journal of Respiratory and Critical Care Medicine, vol. 202, No. 5, Sep. 1, 2020, pp. 681-689.

Arschang Valipour et al. Bronchial Rheoplasty for Treatment of Chronic Bronchitis. Twelve-Month Results from a Multicenter Clinical Trial, American Journal of Respiratory and Critical Care Medicine, vol. 202, Issue 5, 2019.

Arschang Valipour, et Al. Late Breaking Abstract—Bronchial Rheoplasty for Treatment of Chronic Bronchitis: 6 Month Results from a Prospective Multi-Center Study, Abstract, European Respiratory Journal 2019, pp. 1-5.

Charalambous et al., The Efficacy and Safety of the Open Approach Irreversible Electroporation in the Treatment of Pancreatic Cancer: A Systematic Review, European Journal of Surgical Oncology; vol. 46, No. 9, Sep. 2020.

Co-pending U.S. Appl. No. 18/416,505, inventor Neal; Robert E., filed Jan. 18, 2024.

Co-pending U.S. Appl. No. 18/423,043, inventor Krimsky; William Sanford, filed Jan. 25, 2024.

Davalos et al., Implications and Considerations of Thermal Effects When Applying Irreversible Electroporation Tissue Ablation Therapy, Prostate; vol. 75, No. 10; pp. 1114-1118, Jul. 1, 2015.

Edd et al., In Vivo Results of a New Focal Tissue Ablation Technique: Irreversible Electroporation, IEEE Transactions on Biomedical Engineering, vol. 53, No. 5; pp. 1409-1415; Jun. 2006.

EP18836576.1 Search Report dated Jun. 8, 2021.

EP20792123.0 Extended and Supplementary European Search Report dated Dec. 21, 2022.

EP23178276.4 Extended European Search Report dated Jun. 26, 2023.

Frandsen et al., Calcium electroporation Q4 in three cell lines; a comparison of bleomycin 2 and calcium, calcium compounds, and pulsing conditions, Biochimica et Biophysica Acta, vol. 1840, No. 3; pp. 1204-1208, Mar. 2014.

International Preliminary Report on Patentability for PCT/US2018/067501 dated Jun. 30, 2020.

International Search Report and Written Opinion for PCT/US2018/067504 on Jun. 30, 2020.

International Search Report and Written Opinion for PCT/US2020/028844 on Sep. 4, 2020.

Kundalia et al., Margin Accentuation for resectable Pancreatic cancer using Irreversible Electroporation e Results from the MACPIE-I study, European Journal of Surgical Oncology, vol. 47, No. 10: pp. 2571-2578; Oct. 2021.

"Lu, et al., "Sequence-Modified Antibiotic Resistance Genes Provide Sustained Plasmid-Mediated Transgene Expression in Mammals" (2017) Molecular Therapy, vol. 25, No. 5, pp. 1187-1198".

Maor et al., Irreversible Electroporation Attenuates Neointimal Formation After Angioplasty, IEEE Transactions on Biomedical Engineering, vol. 55, No. 9, Sep. 2008.

Maor et al., The Effect of Irreversible Electroporation on Blood Vessels, Technology in Cancer Research and Treatment, vol. 6, No. 4, Aug. 2007.

Pallav L Shah, et al. *Epithelial Resurfacing: The Bronchial Skin Peel, American Thoracic Society*, May 22, 2020, pp. 1-8.

PCT/US2018/067501 International Search Report and Written Opinion dated Mar. 13, 2019.

PCT/US2021/026221 International Search Report and Written Opinion dated Jul. 21, 2021.

PCT/US2022/015217 International Search Report and Written Opinion dated May 6, 2022.

PCT/US2022/021888 International Search Report and Written Opinion dated Jun. 16, 2022.

Reddy et al., Pulsed Field Ablation of Paroxysmal Atrial Fibrillation, JACC Clin Electrophysiology vol. 7 No. 5, pp. 614-627, May 2021.

Rubinsky et al., "Irreversible Electroporation: a New Ablation Modality—Clinical Implications," Tech. Cancer Res. Treatment 6:1-12 (2007).

S. Fernandez-Bussy, et Al. *Histopathologic Results Post Bronchial Rheoplasty*, Epidemiology and Therapy, Mini Symposium, May 22, 2019, Abstract.

Timmer et al., Irreversible Electroporation for Locally Advanced Pancreatic Cancer, Techniques in Vascular and Interventional Radiology vol. 23, Issue 2, Jun. 2020.

U.S. Appl. No. 16/914,072 Notice of Allowance dated Jun. 20, 2022.

U.S. Appl. No. 17/214,688 Notice of Allowance dated Feb. 4, 2022.

U.S. Appl. No. 17/214,688 Notice of Allowance dated Mar. 2, 2022.

U.S. Appl. No. 16/914,200 Notice of Allowance dated Sep. 8, 2022.

U.S. Appl. No. 16/914,200 Office Action dated May 4, 2022.

U.S. Appl. No. 16/914,200 Office Action dated Oct. 22, 2021.

U.S. Appl. No. 17/214,688 Office Action dated Sep. 7, 2021.

U.S. Appl. No. 17/502,640 Office Action dated Apr. 28, 2023.

U.S. Appl. No. 17/502,640 Office Action dated Jul. 13, 2022.

U.S. Appl. No. 17/502,640 Office Action dated Mar. 14, 2022.

U.S. Appl. No. 17/502,640 Office Action dated Nov. 27, 2023.

U.S. Appl. No. 18/077,097 Corrected Notice of Allowability dated Dec. 26, 2023.

U.S. Appl. No. 18/077,097 Notice of Allowance dated Oct. 27, 2023.

U.S. Appl. No. 18/077,097 Office Action dated Aug. 3, 2023.

U.S. Appl. No. 17/214,688 Office Action dated May 25, 2021.

U.S. Appl. No. 16/914,072 Office Action dated Nov. 26, 2021.

V. Kim et Al. *Bronchial Rheoplasty Increases Distal Airway Volume in Chronic Bronchitis*, European Respiratory Journal 2019, vol. 54, Suppl. 63, PA2040 Abstract.

Valipour, A., Ing, A., Williamson, J., et al. *Late Breaking Abstract—First-in-Human Results of Bronchial Rheoplasty: An Endobronchial Treatment for Chronic Bronchitis* (*CB*). European Respiratory Journal 2018 52: Suppl. 62, OA2162.

Verma et al., Primer on Pulsed Electrical Field Ablation: Understanding the Benefits and Limitations, Circulation: Arrhythmia and Electrophysiology, vol. 14, No. 9, Sep. 20, 2021.

Xie et al., Ablation of Myocardial Tissue With Nanosecond Pulsed Electric Fields, Plos One, vol. 10, No. 12, Dec. 14, 2015.

Yavin et al., Pulsed Field Ablation Using a Lattice Electrode for Focal Energy Delivery, Circulation: Arrhythmia and Electrophysiology, vol. 13, No. 6, May 6, 2020.

U.S. Appl. No. 17/502,640 Notice of Allowance dated Sep. 26, 2024.

(56) References Cited

OTHER PUBLICATIONS

U.S. Appl. No. 17/502,640 Supplemental Notice of Allowability dated Dec. 23, 2024.
U.S. Appl. No. 18/416,505 Office Action dated Oct. 1, 2024.
U.S. Appl. No. 18/423,043 Office Action dated Nov. 4, 2024.
Al-Sakere, et al., Tumor Ablation with Irreversible Electroporation, *PLoS One*, 2(11):e1135. doi:10.1371/journal.pone.0001135 (Nov. 2007).
Arena C.B., et al., "Chapter 10.13: Electroporation Therapy," Comprehensive Biomedical Physics, Springer, Editor: A. Brahme, 2014, vol. 10, pp. 269-287 (20 Pages), Retrieved from URL: http://dx.doi.org/10.1016/8978-0-444-53632-7.01016-9.
Arena C.B., et al., "High-frequency Irreversible Electroporation (H-FIRE) for Non-thermal Ablation without Muscle Contraction," Biomedical Engineering Online, Nov. 21, 2011, vol. 10, Article No. 102, pp. 1-20 (21 Pages).
Arena, et al., High-frequency irreversible electroporation (H-FIRE) for non-thermal ablation without muscle contraction, *BioMedical Engineering OnLine*, 10:102, http://www.biomedical-engineering-online.com/content/10/1/102 (Nov. 2011).
Bertacchini, et al., Design of an Irreversible Electroporation System for Clinical Use, *Technology in Cancer Research and Treatment*, 6(4):313-320 (Aug. 2007).
Bhonsle S., et al., "Characterization of Irreversible Electroporation Ablation with a Validated Perfused Organ Model," Journal of Vascular and Interventional Radiology, 2016, vol. 27, pp. 1913-1922 (12 Pages), Appendix A—Supplemental Materials and Methods.
Campelo S., et al., "An Evaluation of Irreversible Electroporation Thresholds in Human Prostate Cancer and Potential Correlations to Physiological Measurements," APL Bioengineering, 2017, vol. 1 (016101), pp. 016101-1-016101-10, Retrieved from URL: https://doi.org/10.1063/1.5005828.
Cerveri I., et al., "Variations in the Prevalence Across Countries of Chronic Bronchitis and Smoking Habits in Young Adults," The European Respiratory Journal, 2001, vol. 18, No. 1, pp. 85-92.
Cheetham J., et al., "Effects of Functional Electrical Stimulation on Denervated Laryngeal Muscle in a Large Animal Model," Artificial Organs, 2015, vol. 39, No. 10, pp. 876-885.
Criner G.G., "Chronic Bronchitis: The Case for an Unmet Medical Need," European Respiratory Society (ERS), 2017, 13 Pages.
Davalos, et al., Tissue Ablation with Irreversible Electroporation, *Annals of Biomedical Engineering*, 33(2):223-231 (Feb. 2005).
Dean D.A., "Gene Electrotransfer to Lung," Clinical Aspects of Electroporation, Springer Science Business Media, LLC, Chapter 15, 2011, pp. 165-175.
Dev, et al., Medical Applications of Electroporation, *IEEE Transactions on Plasma Science*, 28(1):206-223 (Feb. 2000).
Dupuy D.E., et al., "Irreversible Electroporation in a Swine Lung Model," Cardiovascular and Interventional Radiology, 2011, vol. 34, No. 2, pp. 391-395.
Edd, et al., In Vivo Results of a New Focal Tissue Ablation Technique: Irreversible Electroporation, *IEEE Transactions On Biomedical Engineering*, 53(5):1409-1415 (Jun. 2006).
Eurostat Statistics Database: "Health at a Glance: Europe (2012 and 2014 Reports)," Dec. 3, 2014, 41 Pages, Retrieved from URL: http://www.oecd-ilibrary.org/social-issues-migration-health/health-at-a-glance-europe-2012_978926418.
Extended European Search Report for European Application No. 20840607.4, dated Jun. 27, 2023, 08 Pages.
Extended European Search Report for European Application No. 21785398.5, dated Apr. 4, 2024, 8 Pages.
Extended European Search Report for European Application No. 21853941.9, dated Jul. 23, 2024, 07 Pages.
Extended European Search Report for European Application No. 22210537.1, dated Apr. 26, 2023, 11 Pages.
Extended European Search Report for European Application No. 22820712.2, dated Apr. 7, 2025, 08 Pages.
Extended European Search Report for European Application No. 22821096.9, dated Aug. 6, 2025, 13 Pages.
Extended European Search Report for European Application No. 23174654.6, dated Jun. 23, 2023, 07 Pages.
Extended European Search Report for European Application No. 25166670.7, dated May 15, 2025, 8 Pages.
Extended European Search Report for European Application No. 25184327.2, dated Jul. 15, 2025, 08 Pages.
Extended European Search Report for European Application No. EP22776703.5, dated Dec. 23, 2024, 8 Pages.
Extended European Search Report for European Application No. EP22870831.9, dated Jun. 16, 2025, 10 Pages.
Faststats-Chronic Lower Respiratory Disease: "Chronic Obstructive Pulmonary Disease (COPD) Includes: Chronic Bronchitis and Emphysema," Centers for Disease Control and Prevention (CDC)/National Center for Health Statistics (NCHS), Jan. 16, 2021, pp. 1-2, [Retrieved on Feb. 4, 2021] Retrieved from URL: https://www.cdc.gov/nchs/fastats/copd.htm.
Fernandez-Bussy S., et al., "Histopathologic Results Post Bronchial Rheoplasty," American Thoracic Society, 2019, 17 Pages.
Garcia P.A., et al., "A Parametric Study Delineating Irreversible Electroporation from Thermal Damage Based on a Minimally Invasive Intracranial Procedure," BioMedical Engineering OnLine, Apr. 30, 2011, vol. 10, Article No. 34, 22 Pages, Retrieved from URL: http://www.biomedical-engineering-online.com/content/10/1/34.
Garcia P.A., et al., "An Experimental Investigation of Temperature Changes During Electroporation," URSI General Assembly and Scientific Symposium, Istanbul, Turkey, Aug. 13-20, 2011, 4 Pages.
Garcia P.A., et al., "Intracranial Nonthermal Irreversible Electroporation: In Vivo Analysis," The Journal of Membrane Biology, 2010, vol. 236, pp. 127-136.
Garcia P.A., et al., "Non-Thermal Irreversible Electroporation for Tissue Ablation," Chapter 3, Electroporation in Laboratory and Clinical Investigations, Editors: E. P. Spugnini and al Baldi, 2010, 22 Pages.
Global Strategy for the Diagnosis, Management, and Prevention of COPD: "Global Initiative for Chronic Obstructive Lung Disease," 2017, pp. 1-42.
Gowrishankar, et al., Electrical behavior and por accumulation in a multicellular model for conventional and supra-electroporation, Biochem. Biophys. Res. Commun., 349(2):643-653 (Oct. 2006).
Ibey, et al., Plasma Membrane Permeabilization by Trains of Ultrashort Electric Pulses, Bioelectrochemistry, 79(1):114-121 (Aug. 2010).
International Search Report & Written Opinion dated Aug. 29, 2025 in Int'l PCT Patent Appl. Serial No. PCT/US2025/028619 (181001).
International Search Report and Written Opinion for International Application No. PCT/US2017/039527, dated Dec. 7, 2017, 22 Pages.
International Search Report and Written Opinion for International Application No. PCT/US2018/067504, dated Mar. 13, 2019, 13 Pages.
International Search Report and Written Opinion for International Application No. PCT/US2020/042260, dated Oct. 14, 2020, 12 Pages.
International Search Report and Written Opinion for International Application No. PCT/US2021/030911, dated Aug. 16, 2021, 10 Pages.
International Search Report and Written Opinion for International Application No. PCT/US2021/044469, dated Nov. 8, 2021, 17 Pages.
International Search Report and Written Opinion for International Application No. PCT/US2022/032981, dated Aug. 29, 2022, 15 Pages.
International Search Report and Written Opinion for International Application No. PCT/US2022/044021, dated Jan. 11, 2023, 11 Pages.
International Search Report and Written Opinion for International Application No. PCT/US2023/020282, dated Jul. 21, 2023, 14 Pages.
International Search Report and Written Opinion for International Application No. PCT/US2023/022109, dated Aug. 15, 2023, 10 Pages.

(56) References Cited

OTHER PUBLICATIONS

International Search Report and Written Opinion for International Application No. PCT/US2023/060897, dated Jul. 7, 2023, 15 Pages.
International Search Report and Written Opinion for International Application No. PCT/US2024/020309, dated Jul. 29, 2024, 10 Pages.
International Search Report and Written Opinion for International Application No. PCT/US2024/043295, dated Oct. 30, 2024, 9 Pages.
Invitation to Pay Additional Fees for International Application No. PCT/US2023060897, dated May 15, 2023, 10 Pages.
Jourabchi, et al., Irreversible Electroporation (NanoKnife) in Cancer Treatment, *Gastrointestinal Intervention*, 3:8-18 (Feb. 2014).
Kim, et al., Technical Feasibility and Safety of Image-Guided Biphasic Monopolar Pulsed Electric Field Ablation of Metastatic and Primary Malignancies, J. Vasc. Interv. Radiol., 35:1644-1654 (2024).
Kim H.B., et al., "Physicochemical Factors That Affect Electroporation of Lung Cancer and Normal Cell Lines," Biochemical and Biophysical Research Communications, 2019, vol. 517, No. 4, pp. 703-708.
Kim V., et al., "The Chronic Bronchitic Phenotype of COPD: An Analysis of the COPD Gene Study," Chest, Sep. 2011, vol. 140, No. 3, pp. 626-633.
Krassowska, et al., Viability of Cancer Cells Exposed to Pulsed Electric Fields: The Role of Pulse Charge, *Annals of Biomedical Engineering*, 31:80-90 (2003).
Lee, et al., Advanced Hepatic Ablation Technique for Creating Complete Cell Death: Irreversible Electroporation,*Radiology*, 255(2) (Apr. 8, 2010).
Mercadal, et al., Avoiding nerve stimulation in irreversible electroporation: a numerical modeling study, *Phys. Med. Biol.*, 62(20):8060-8079 (Oct. 2004).
Miklavcic, et al., A validated model of in vitro electric field distribution in tissues for electrochemotherapy and for DNA electrotransfer for gene therapy, *Biochimica et Biophysica Acta*, 1523:73-83 (2000).
Miklavcic, et al., The effect of high frequency electric pulses on muscle contractions and antitumor efficiency in vivo for a potential use in clinical electrochemotherapy, *Bioelectrochemistry*, 65:121-128 (2005).
Miklovic T., et al., "A Comprehensive Characterization of Parameters Affecting High-frequency Irreversible Electroporation Lesions," Annals of Biomedical Engineering, 2017, vol. 45, pp. 2524-2534 (11 Pages).
Miller, et al., Cancer Cells Ablation with Irreversible Electroporation, *Technology in Cancer Research & Treatment*, 4(6):699-705 (Dec. 2005).
Mir, et al., Mechanisms of electrochemotherapy, *Advanced Drug Delivery Reviews*, 35:107-118 (1999).
Moore, et al., Early experience with PEF in the setting of recalcitrant stage IV lung cancer, Lung Cancer, 204:08575 (May 2025).
Napotnik, et al., Cell death due to electroporation—A Review, *Bioelectrochemistry*, 141:107871, pp. 1-18 (2021).
Neal II, R. E. et al., "The Feasibility of Irreversible Electroporation for the Treatment of Breast Cancer and Other Heterogeneous Systems," Annals of Biomedical Engineering, Dec. 2009, vol. 37, No. 12, pp. 2615-2625.
Neal II R.E., et al., "An "Off-the-Shelf" System for Intraprocedural Electrical Current Evaluation and Monitoring of Irreversible Electroporation Therapy," Cardio Vascular and Interventional Radiology, 2014, vol. 38, No. 3, pp. 736-741 (6 Pages).
Neal II R.E., et al., "Chapter 5.4: Clinical Implications of Irreversible Electroporation: Clinical and Preclinical Findings," Springer, Editors: H Akiyama and R Heller (In Press), 10 Pages.
Neal II R.E., et al., "Experimental Characterization and Numerical Modeling of Tissue Electrical Conductivity during Pulsed Electric Fields for Irreversible Electroporation Treatment Planning," IEEE Transactions on Biomedical Engineering, Apr. 2012, vol. 59, No. 4, pp. 1076-1085.
Neal II R.E., et al., "Hepatic Epithelioid Hemangioendothelioma Treated With Irreversible Electroporation and Antibiotics," Journal of Clinical Oncology, 2013, vol. 31, 5 Pages, Retrieved from URL: http://jco.ascopubs.org/cgl/dol/10.1200/JCO.2012.44.9736.
Neal II R.E., et al., "Improved Local and Systemic Anti-Tumor Efficacy for Irreversible Electroporation in Immunocompetent versus Immunodeficient Mice," Plos One, May 24, 2013, vol. 8, No. 5 (e64559), 10 Pages, DOI:10.1371/journal.pone.0064559.
Neal II R.E., et al., "In Vitro and Numerical Support for Combinatorial Irreversible Electroporation and Electrochemotherapy Glioma Treatment," Annals of Biomedical Engineering, 2013, vol. 42, 13 Pages, DOI: 10.1007/s10439-013-0923-2.
Neal II R.E., et al., "In vivo Characterization and Numerical Simulation of Prostate Properties for Non-Thermal Irreversible Electroporation Ablation," The Prostate, 2014, vol. 17, No. 10 (22760), 11 Pages.
Neal II R.E., et al., "In Vivo Irreversible Electroporation Kidney Ablation: Experimentally Correlated Numerical Models," IEEE Transactions on Biomedical Engineering, 2013, 10 Pages, DOI: 10.1109/TBME.2014.2360374.
Neal II R.E., et al., "Spectrum of Imaging and Characteristics for Liver Tumors Treated With Irreversible Electroporation," Journal of Biomedical Science and Engineering, 2012, vol. 5, pp. 813-818.
Neal II R.E., et al., "The Effects of Metallic Implants on Electroporation Therapies: Feasibility of Irreversible Electroporation for Brachytherapy Salvage," CardioVascular and Interventional Radiology, 2013, vol. 36, No. 6, pp. 1638-1645 (08 Pages).
Neal II R.E., et al., "Treatment of Breast Cancer through the Application of Irreversible Electroporation Using a Novel Minimally Invasive Single Needle Electrode," Breast Cancer Research and Treatment, Aug. 2010, vol. 123, No. 1, pp. 295-301 (13 Pages).
Neal II R.E., et al., "Successful Treatment of a Large Soft Tissue Sarcoma with Irreversible Electroporation," Journal of Clinical Oncology, May 1, 2011, vol. 29, No. 13, pp. e372-e377, DOI: 10.1200/JCO.2010.33.0902.
Novickij V., et al., "High Frequency Electroporation Efficiency is Under Control of Membrane Capacitive Charging and Voltage Potential Relaxation," Bioelectrochemistry, 2018, vol. 119, pp. 92-97.
O'Brien T.J., et al., "Effects of Internal Electrode Cooling on Irreversible Electroporation Using a Perfused Organ Model," International Journal of Hyperthermia, 2019, vol. 35, No. 1, pp. 44-55 (12 Pages).
Reddy, et al., Pulsed Field Ablation For Pulmonary Vein Isolation in Atrial Fibrillation, Journal of the American College of Cardiology, 74(3):315-326 (Jul. 2019).
Ricke J., et al., "Irreversible Electroporation (IRE) Fails to Demonstrate Efficacy in a Prospective Multicenter Phase II Trial on Lung Malignancies: The ALICE Trial," Cardiovascular and Interventional Radiology, 2015, vol. 38, No. 2, pp. 401-408.
Rogers, et al., Strength-Duration Curve for an Electrically Excitable Tissue Extended Down to Near 1 Nanosecond, *IEEE Transactions on Plasma Science*, 32(4):1587-1599 (Aug. 2004).
Rossmeisl J.H., Jr., et al., "Safety and Feasibility of the Nanoknife System for Irreversible Electroporation Ablative Treatment of Canine Spontaneous Intracranial Gliomas," Journal of Neurosurgery, Jul. 3, 2015, vol. 123, No. 4, pp. 1008-1025 (18 Pages).
Rubinsky, et al., Optimal Parameters for the Destruction of Prostate Cancer Using Irreversible Electroporation, *The Journal of Urology*, 180:2668-2674 (Dec. 2008).
Sano M.B., et al., "Burst and Continuous High Frequency Irreversible Electroporation Protocols Evaluated in a 3D Tumor Model," Physics in Medicine and Biology, Jul. 6, 2018, vol. 63, No. 13 (135022), pp. 1-18.
Sano M.B., et al., "Towards the Creation of Decellularized Organ Constructs Using Irreversible Electroporation and Active Mechanical Perfusion," BioMedical Engineering OnLine, 2010, vol. 9, No. 83, 16 Pages, Retrieved from URL: http://www.biomedical-engineering-online.com/content/9/1/83.
Scheffer H.J., et al., "The Influence of a Metal Stent on the Distribution of Thermal Energy during Irreversible Electroporation," Plos One, Feb. 4, 2016, vol. 11, No. 2 (e0148457), 13 Pages, DOI:10.1371/journal.pone.0148457.

(56) References Cited

OTHER PUBLICATIONS

Schoenbach, et al., Bioelectric Effects of Intense Nanosecond Pulses, IEEE Transactions on Dielectrics & Electrical Insulation, 14(5):1088-1109 (2007).
Schoenbach K.H., et al., "Bioelectrics," Springer, Editors: H. Akiyama, R. Heller, 2017, 491 Pages, ISBN 978-4-431-56093-7, ISBN 978-4-431-56095-1 (eBook), DOI: 10.1007/978-4-431-56095-1.
Shah P.L., et al., "Epithelial Resurfacing: The Bronchial Skin Peel," American Journal of Respiratory and Critical Care Medicine, Sep. 1, 2020, Vo,. 202, No. 5, pp. 641-642.
Tang P.S., et al., "Acute Lung Injury and Cell Death: How Many Ways Can Cells Die," American Journal of Physiology Lung Cellular and Molecular Physiology, Jan. 18, 2008, vol. 294, No. 4, pp. L632-L641.
Thomson K.R., et al., "Introduction to Irreversible Electroporation-Principles and Techniques," Techniques in Vascular and Interventional Radiology, 2015, vol. 18, No. 3, pp. 128-134.
Tri J.A., et al., "Electroporation Ablation of Bronchial Smooth Muscle Cells: A Novel Non-thermal Asthma Therapy," Pulmonary and Critical Care Medicine, 2016, vol. 1, No. 4, pp. 1-4.
Valipour A., et al., "First-in-Human Results of Bronchial Rheoplasty: An endobronchial Treatment for Chronic Bronchitis (CB)," American Thoracic Society, 2019, pp. 1-20.
Vollmer, Robin T., Tumor Length In Prostate Cancer, *American Journal of Clinical Pathology*, 130(1):77-82 (Jul. 2008).
Wandel A., et al., "Optimizing Irreversible Electroporation Ablation with a Bipolar Electrode," The Journal of Vascular and Interventional Radiology, Sep. 2016, vol. 27, No. 9, pp. 1441-1450 (12 Pages).
Weaver, et al., Theory of electroporation: A Review, Bioelectrochemistry and Bioenergetics, 41(2):135-160 (Dec. 1996).

* cited by examiner

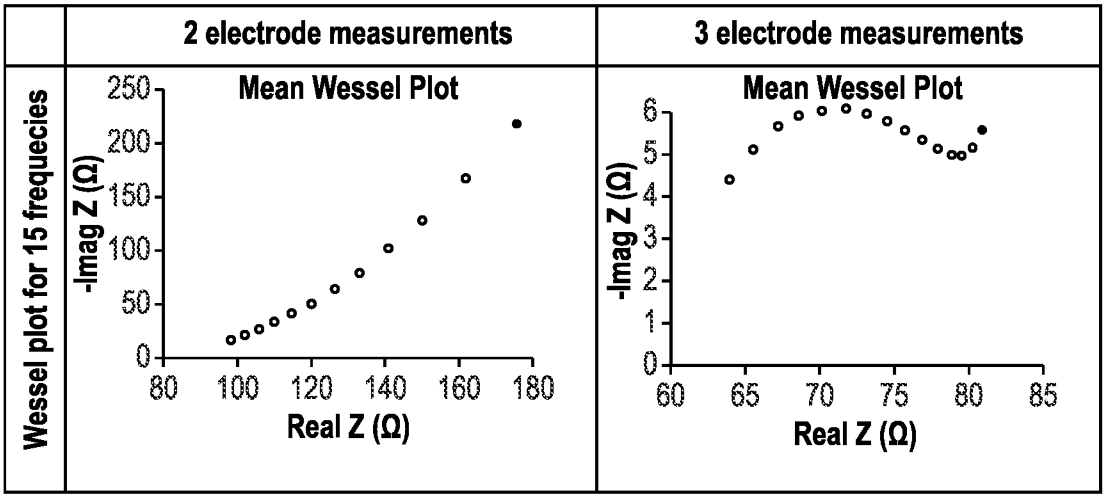
FIG. 6A
FIG. 6B
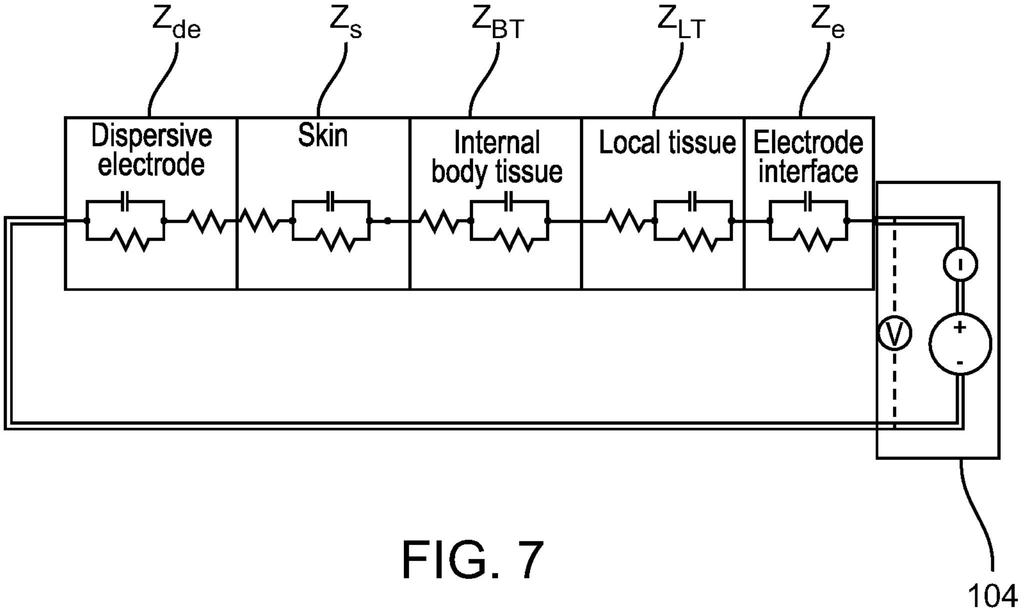
FIG. 7

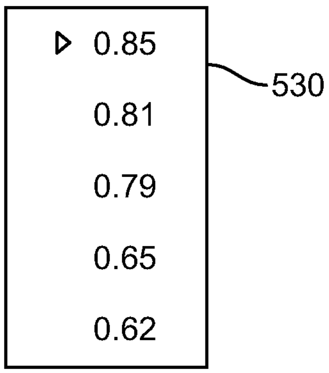
FIG. 25
IBI: 0.85
FIG. 26
PROGRESS: 40%
FIG. 27
DEPTH: 1.2mm
FIG. 28
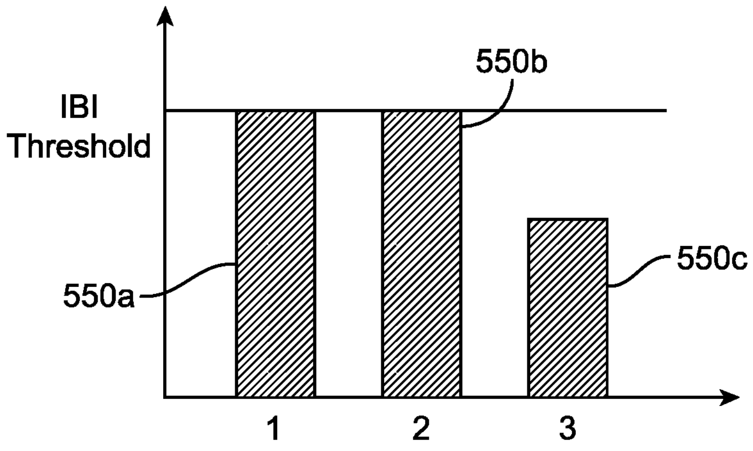
FIG. 29
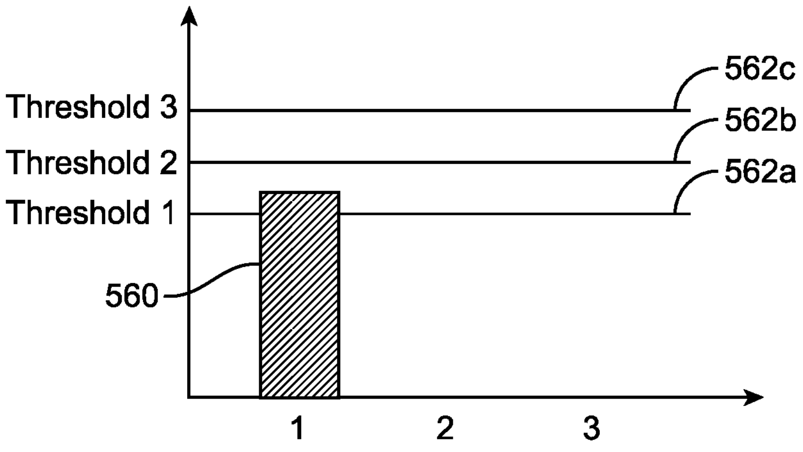
FIG. 30

MULTI-ELECTRODE SYSTEM AND METHOD FOR DEDUCING TREATMENT EFFECT OUTCOMES

PRIORITY CLAIM

This application is a continuation of PCT Application No. PCT/US2022/021888, filed Mar. 25, 2022, which claims priority to and the benefit of U.S. Provisional Patent Application No. 63/166,145, filed Mar. 25, 2021, entitled "Multi-Electrode System and Method for Deducing Treatment Effect Outcomes," the disclosures of which are incorporated herein by reference in their entirety for all purposes.

BACKGROUND

Delivery of electrical energy to the body has been used in a variety of applications ranging from nerve stimulation to ablation of tissue to drug delivery and more. Typically, one or more electrodes are applied to the body, either invasively or non-invasively, and are electrically connected to a waveform generator. Energy is delivered to the body via the one or more electrodes so as to perform a treatment or therapy. The ability to monitor the progress or success of the treatment can vary depending on the location of the tissue targeted for energy delivery. Surface ablation of the skin is typically readily visualizable. Other target locations are internal to the body, such as within the heart, which are more challenging to monitor. Ablation therapy using radio frequency waves delivered to cardiac tissue is used to cure a variety of cardiac arrhythmias such as supraventricular tachycardia, Wolff-Parkinson-White syndrome (WPW), ventricular tachycardia, and more recently as management of atrial fibrillation. Radiofrequency (RF) ablation induces gas bubbles in ablation zones (necrosis zone or thermal lesion) because ablation heating raises the tissue temperature to near the boiling point, generating gas bubbles as strong acoustic scatterers that interact with incident ultrasound to produce hyperechoic regions in brightness scans. Consequently, clinicians have employed a brightness scan to observe the bubble-related hyperechoic region and preliminarily evaluate the ablation zones. However, the performance of the brightness scan in monitoring the RF ablation is operator-dependent and difficult. As a complement, ultrasound elastography techniques have been extensively examined. The fundamental principle of ultrasound elastography in monitoring RF ablation is that the ablated tissues are stiffer compared with normal, untreated tissues. Ultrasound elastography has gradually become the predominant technique used for imaging RF ablation.

However, other types of energy have been used within the body which do not create necrosis zones or thermal lesions, and therefore such monitoring techniques are not usable. For example, pulsed electric field (PEF) therapies deliver non-thermal energy to body tissues. Such energy modifies or destroys cells within the tissue but preserves the underlying protein extracellular matrix of tissues that provides the interstitial architectural structure and structure-related functions of the tissue. Consequently, direct visualization of treatment effects or real-time monitoring of depth or volume of treatment cannot be adequately and accurately interpreted by direct visualization or typical imaging modalities. This is especially true for applications of PEFs where cell death is not the targeted objective of the therapy.

One proposed solution for providing real-time feedback to clinicians is to examine the pulsed electrical energy metrics, such as electric current, resistance, or impedance. This has been proposed for bipolar electrode systems. The clinician either uses the inherent therapeutic pulse metrics or relies on using the therapeutic electrodes to also deliver test signals. The effectiveness is dependent on the close proximity of the electrodes to the affected regions, generally immersing them within the tissue where the properties are changing, enabling presentation of the affected changes. In research environments, four-probe systems are occasionally employed to increase the sensitivity of the probing system. However, these systems are more complex to establish within the in vivo environment and are thus generally reserved for academic investigations under highly controlled environments and conditions. Likewise, such systems are only applicable to bipolar electrode systems.

Thus, improved real-time monitoring systems are desired for use in vivo, particularly for monopolar energy delivery systems. Such systems should be reliable, cost effective and easy to use. At least some of these objectives will be met by the systems, methods and devices described herein.

SUMMARY

Certain embodiments of the present technology are directed to a monopolar treatment delivery system, comprising an energy delivery electrode, a dispersive electrode, a reference electrode, and a generator in electrical communication with the energy delivery electrode, the dispersive electrode, and the reference electrode. In certain such embodiments, the generator is configured to deliver an impedance measurement signal to target tissue using the energy delivery electrode and the dispersive electrode, while the energy delivery electrode is proximate to the target tissue and the dispersive electrode is remote from the target tissue. The generator is also configured to measure a voltage between the energy delivery electrode and the reference electrode. Additionally, the generator is configured to monitor an impedance of the target tissue based on a current of the impedance measurement signal and the voltage between the energy delivery electrode and the reference electrode. In certain such embodiments, the generator is configured to measure the current of the impedance measurement signal directly or indirectly, or to control the current of the impedance measurement signal.

In accordance with certain embodiments, the generator is configured to deliver a monopolar treatment signal to the target tissue using the energy delivery electrode and the dispersive electrode, deliver the impedance measurement signal to the target tissue prior to the monopolar treatment signal being delivered to the target tissue to thereby enable a baseline impedance measurement to be obtained, and deliver a further instance of the impedance measurement signal to the target tissue after the monopolar treatment signal is delivered to the target tissue to thereby enable a post-treatment impedance measurement to be obtained.

In accordance with certain embodiments, the impedance measurement signal includes a low frequency portion and a high frequency portion, wherein the low frequency portion of the impedance measurement signal temporally precedes the high frequency portion of the impedance measurement signal, or vice versa.

In accordance with certain embodiments, the controller is configured to calculate, based on both the baseline impedance measurement and the post-treatment impedance measurement, a metric indicative of changes to the target tissue caused by the delivery of the monopolar treatment signal.

In accordance with certain embodiments, the controller is configured to calculate the metric indicative of changes to the target tissue caused by the delivery of the monopolar treatment signal by calculating an impedance-based indicator (IBI), which includes: calculating a difference between a post-treatment low frequency impedance phase angle value measurement $\angle Z_{LF}$(t) measured at a time t after the monopolar treatment signal has been delivered, and a baseline low frequency impedance phase angle value measurement $\angle Z_{LF}$(0) measured at a time t=0 prior to the monopolar treatment signal being delivered; and calculating the IBI based on the difference between the post-treatment low frequency impedance phase angle value measurement $\angle Z_{LF}$(t) and the baseline low frequency impedance phase value measurement $\angle Z_{LF}$(0).

In accordance with certain embodiments, at least one of the baseline impedance measurement and the post-treatment impedance measurement obtained by the controller includes a high frequency impedance magnitude value $Z_{HF}$. Additionally, the controller is configured to scale the difference between the post-treatment low frequency impedance phase value measurement $\angle Z_{LF}$(t) and the baseline low frequency impedance phase value measurement $\angle Z_{LF}$(0) by the high frequency impedance magnitude value $Z_{HF}$, when the controller calculates the impedance-based indicator (IBI). More specifically, in accordance with certain embodiments, the controller is configured to calculate the IBI using the following equation:

$$IBI=(\angle Z_{LF}(t)-\angle Z_{LF}(0))\cdot|Z_{HF}|,$$

where

- $\angle Z_{LF}$(0) is a low frequency impedance phase angle value measured at a time t=0 prior to the monopolar treatment signal being delivered,
- $\angle Z_{LF}$(t) is a low frequency impedance phase angle value measured at a time t after the monopolar treatment signal has been delivered, and
- $Z_{HF}$ is a high frequency impedance magnitude value measured prior to the monopolar treatment signal being delivered, or after the monopolar treatment signal has been delivered, which magnitude value is used as a scaling factor.

In accordance with certain embodiments, the monopolar treatment signal comprises a pulsed electric field (PEF) treatment signal. Alternatively, the monopolar treatment signal comprises one of a radio frequency (RF) treatment signal, a microwave treatment signal, a cryogenic treatment signal, an electrochemical treatment signal, or a high frequency ultrasound signal.

Certain embodiments of the present technology are directed to methods for use with a monopolar treatment delivery system that is configured to use an energy delivery electrode and a dispersive electrode to deliver a monopolar treatment signal to target tissue of a patient. As will be appreciated from the below discussion, such a method can be used to deduce a treatment effect outcome resulting from delivery of the monopolar treatment signal.

In accordance with certain embodiments, such a method includes delivering an impedance measurement signal to the target tissue using the energy delivery electrode and the dispersive electrode, while the energy delivery electrode is proximate to the target tissue and the dispersive electrode is remote from the target tissue. The method also includes measuring a voltage between the energy delivery electrode and a reference electrode that is distinct from the dispersive electrode. Additionally, the method includes monitoring an impedance of the target tissue based on a current of the impedance measurement signal and the voltage between the energy delivery electrode and the reference electrode that is distinct from the dispersive electrode. The current of the impedance measurement signal can measured directly (e.g., using an Amp meter, or the like). Alternatively, the current of the impedance measurement signal can be measured indirectly, e.g., by measuring a voltage drop across a resistor having a known resistance, and calculating the current using Ohms law (e.g., I=V/R). Alternatively, the current can be known because it is controlled using a controlled current source, or the like.

In accordance with certain embodiments, a first instance of the delivering the impedance measurement signal to the target tissue, a first instance of the measuring the voltage between the energy delivery electrode and the reference electrode, and a first instance of the monitoring the impedance of the target tissue, are performed prior to a monopolar treatment signal being delivered to the target tissue using the energy delivery electrode and the dispersive electrode, to thereby enable a baseline impedance measurement to be obtained. Following the baseline impedance measurement being obtained, the method further comprises delivering the monopolar treatment signal to the target tissue using the energy delivery electrode and the dispersive electrode. Thereafter, following the delivering the monopolar treatment signal to the target tissue, the method comprises a second instance of the delivering the impedance measurement signal to the target tissue, a second instance of the measuring the voltage between the energy delivery electrode and the reference electrode, and a second instance of the monitoring the impedance of the target tissue, to thereby enable a post-treatment impedance measurement to be obtained.

In accordance with certain embodiments, the impedance measurement signal includes a low frequency portion and a high frequency portion, wherein the low frequency portion of the impedance measurement signal temporally precedes the high frequency portion of the impedance measurement signal, or vice versa.

In accordance with certain embodiments, the method can include calculating, based on both the baseline impedance measurement and the post-treatment impedance measurement, a metric indicative of changes to the target tissue caused by the delivery of the monopolar treatment signal. More specifically, in accordance with certain embodiments, the calculating the metric indicative of changes to the target tissue caused by the delivery of the monopolar treatment signal comprises calculating an impedance-based indicator (IBI), which includes calculating a difference between a post-treatment low frequency impedance phase angle value measurement $\angle Z_{LF}$(t) measured at a time t after the monopolar treatment signal has been delivered, and a baseline low frequency impedance phase angle value measurement $\angle Z_{LF}$(0) measured at a time t=0 prior to the monopolar treatment signal being delivered, and calculating the IBI based on the difference between the post-treatment low frequency impedance phase angle value measurement $\angle Z_{LF}$(t) and the baseline low frequency impedance phase value measurement $\angle Z_{LF}$(0).

In accordance with certain embodiments, at least one of baseline impedance measurement and the post-treatment impedance measurement includes a high frequency impedance magnitude value $Z_{HF}$. In certain such embodiments, the difference between the post-treatment low frequency impedance phase value measurement $\angle Z_{LF}$(t) and the baseline low frequency impedance phase value measurement $\angle Z_{LF}$(0) is scaled by the high frequency impedance magnitude value $Z_{HF}$ when calculating the IBI. More specifically, in accordance with certain embodiments, the IBI is calculated using the following equation:

$$IBI=(\angle Z_{LF}(t)-\angle Z_{LF}(0))\cdot|Z_{HF}|,$$

where $\angle Z_{LF}(0)$ is a low frequency impedance phase angle value measured at a time t=0 prior to the monopolar treatment signal being delivered, $\angle Z_{LF}(t)$ is a low frequency impedance phase angle value measured at a time t after the monopolar treatment signal has been delivered, and $Z_{HF}$ is a high frequency impedance magnitude value measured prior to or after the monopolar treatment signal has been delivered, which magnitude value is used as a scaling factor.

One or more of the above summarized methods can be used to deduce a treatment effect outcome resulting from delivery of the monopolar treatment signal.

In accordance with certain embodiments, one or more of the methods summarized above is/are performed by at least one processor of a monopolar treatment delivery system, which at least one processor can be part of a controller of the monopolar treatment delivery system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

These and other embodiments are described in further detail in the following description related to the appended drawing figures.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 6A-6B provide example measurements performed over the same sample using a conventional two electrode method and a multi-electrode method described herein.

FIG. 7 provides a model of the impedances encountered in FIG. 5 when measuring the voltage signal developed across the tissue.

FIG. 25 illustrates a scrolling display of IBI values.

FIG. 26 illustrates a display of a single IBI value.

FIG. 27 illustrates progress provided as a numerical percentage of completion that changes over time.

FIG. 28 illustrates progress provided as depth of penetration of the treatment.

FIG. 29 illustrates a series of treatment bar graphs that each approach an IBI threshold indicating completion of each individual treatment.

FIG. 30 illustrates a series of a treatment bar graph approaching a plurality of thresholds.

DETAILED DESCRIPTION

A variety of therapeutic energy delivery systems rely on monopolar delivery methods. Monopolar delivery is considered the application of a current to a treatment site using a comparatively small active electrode under which the treatment effects occur and a large dispersive (also referred to as a return electrode) somewhere else on or in the patient's body. The current passes through the patient as it completes the circuit from the active electrode to the dispersive electrode.

Example Monopolar System

Figure 1:
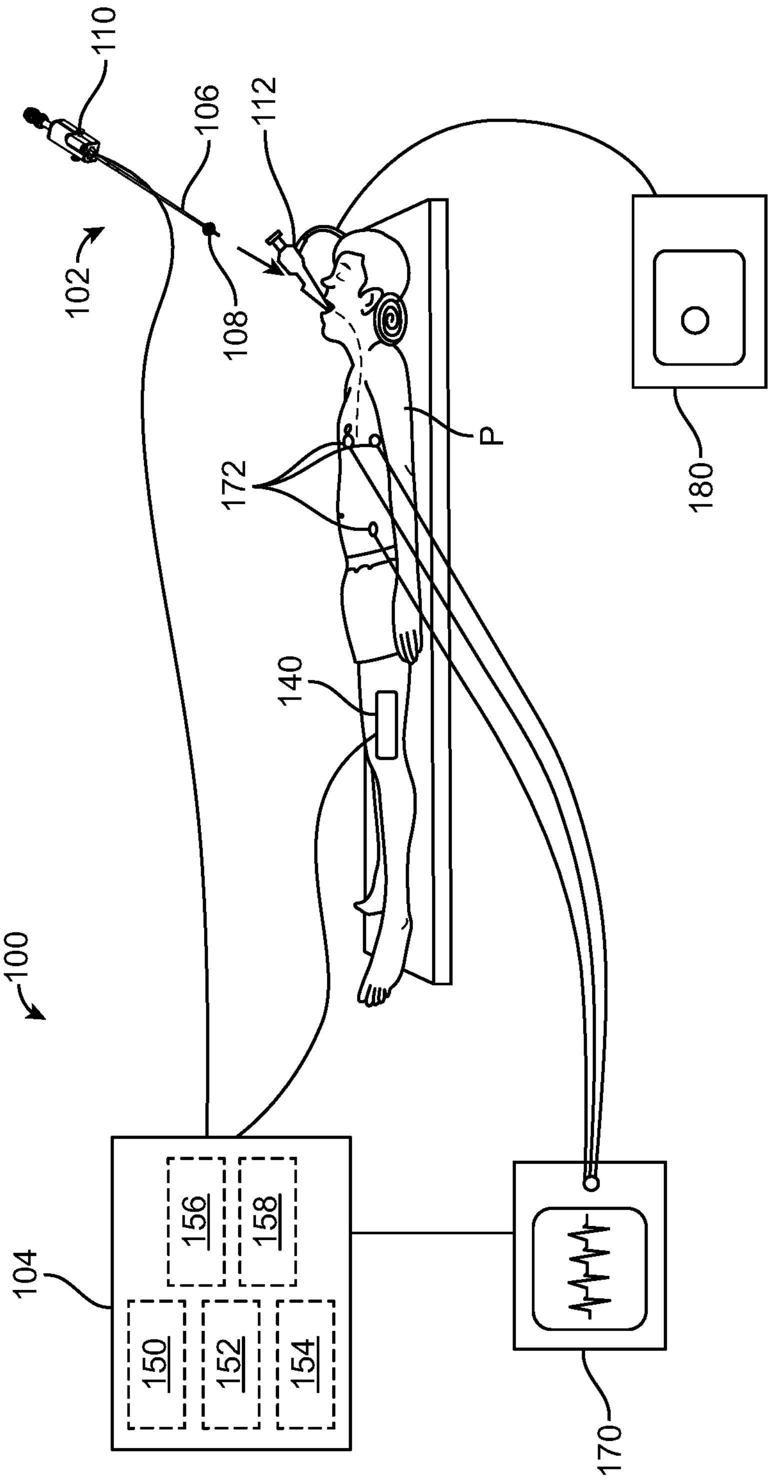
FIG. 1 illustrates an example embodiment of such a monopolar delivery system.

An example of such a monopolar delivery system is illustrated in FIG. 1. FIG. 1 illustrates an embodiment of a pulmonary tissue modification system 100 used in treatment of a patient P. In this embodiment, the system 100 comprises a therapeutic energy delivery catheter 102 connectable to a generator 104. The catheter 102 comprises an elongated shaft 106 having at least one energy delivery body 108 near its distal end and a handle 110 at its proximal end. Connection of the catheter 102 to the generator 104 provides electrical energy to the energy delivery body 108, among other features. In this embodiment, the catheter 102 is insertable into the bronchial passageways of the patient P by a variety of methods, such as through a lumen in a bronchoscope 112, as illustrated in FIG. 1.

Figure 2:
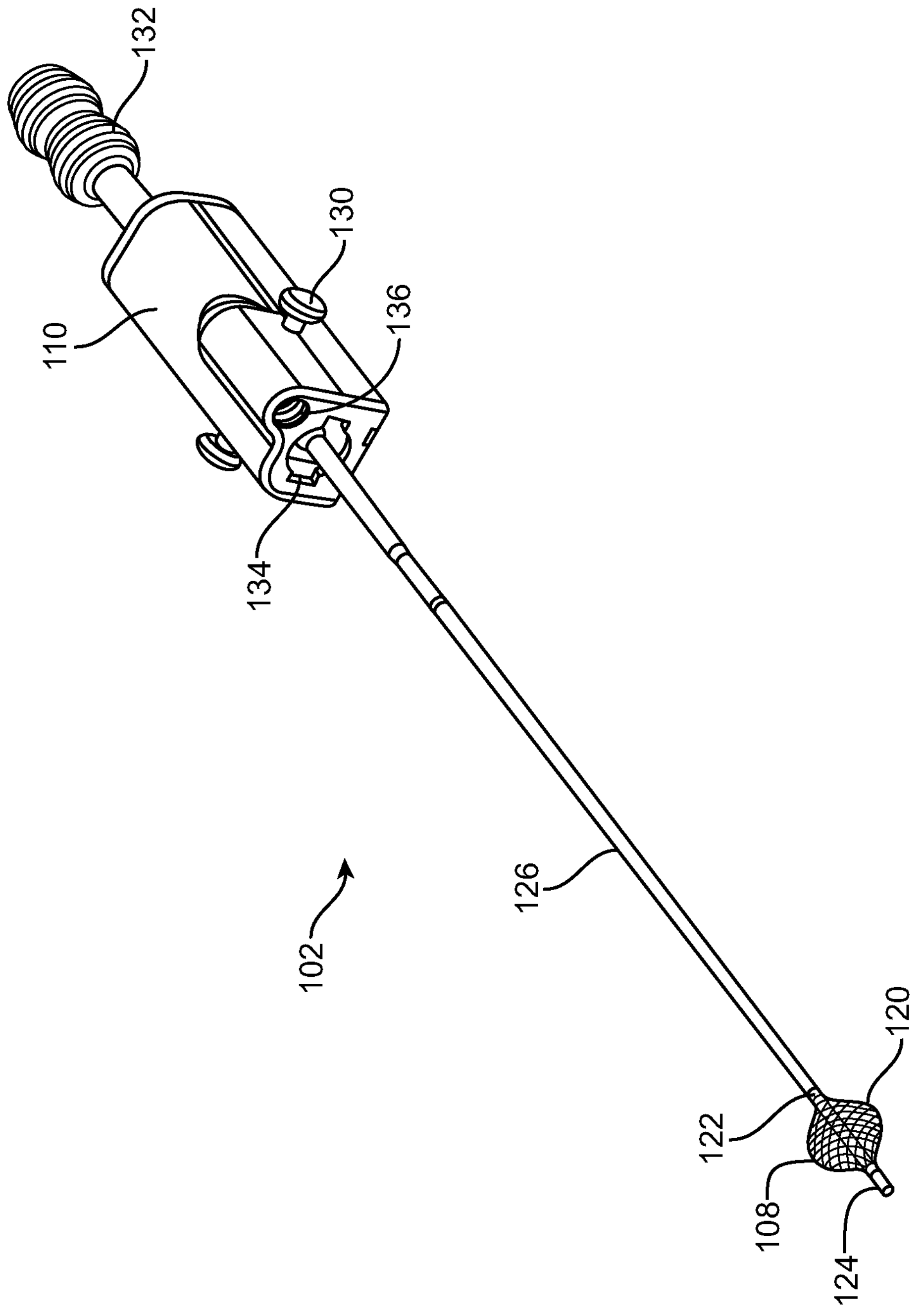
FIG. 2 provides a closer view of the embodiment of the therapeutic energy delivery catheter illustrated in FIG. 1.

FIG. 2 provides a closer view of the embodiment of the therapeutic energy delivery catheter 102 illustrated in FIG. 1. In this embodiment, the energy delivery body 108 comprises a single monopolar energy delivery electrode, however it may be appreciated that other types, numbers and arrangements may be used, further examples of which will be provided herein. In this embodiment, the energy delivery body 108 is comprised of a plurality of wires or ribbons 120 constrained by a proximal end constraint 122 and a distal end constraint 124 forming a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. In some embodiments, the energy delivery body 108 is self-expandable and delivered to a targeted area in a collapsed configuration. This collapsed configuration can be achieved, for example, by placing a sheath 126 over the energy delivery body 108. In FIG. 2, the catheter shaft 106 (within the sheath 126) terminates at the proximal end constraint 122, leaving the distal end constraint 124 essentially unconstrained and free to move relative to the shaft 106 of the catheter 102. Advancing the sheath 126 over the energy delivery body 108 allows the distal end constraint 124 to move forward, thereby lengthening/collapsing and constraining the energy delivery body 108.

The catheter 102 includes a handle 110 at its proximal end. In some embodiments, the handle 110 is removable, such as by pressing a handle removal button 130. In this embodiment, the handle 110 includes an energy delivery body manipulation knob 132 wherein movement of the knob 132 causes expansion or retraction/collapse of the basket-shaped electrode. In this example, the handle 110 also includes a bronchoscope working port snap 134 for connection with the bronchoscope 112 and a cable plug-in port 136 for connection with the generator 104.

Referring back to FIG. 1, in this embodiment, the therapeutic energy delivery catheter 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the catheter 102 and the return electrode 140. It may be appreciated that bipolar energy delivery and other arrangements may alternatively be used, as will be described in further detail herein. In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, but as new technology is developed any suitable element(s) may be used. In addition, one or more communication ports are included.

In some embodiments, the therapeutic energy comprises pulsed electric fields and is characterized by high voltage pulses which allow for removal of target tissue with little or no destruction of critical anatomy, such as tissue-level architectural proteins among extracellular matrices. It may be appreciated that a variety of energy delivery algorithms 152 may be used to deliver such energy. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail in later sections. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 3:
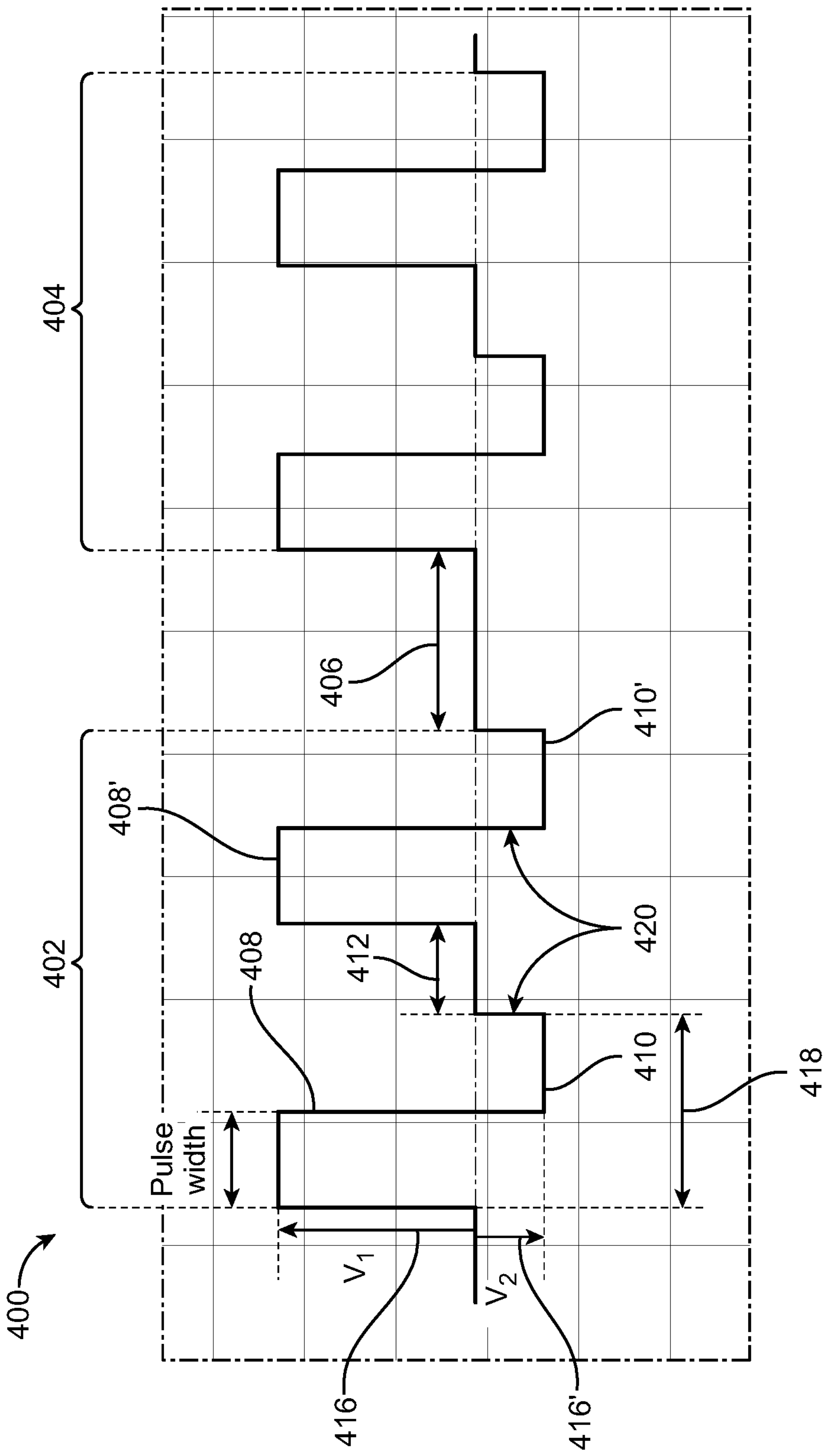
FIG. 3 illustrates an embodiment of a waveform of a signal prescribed by an energy delivery algorithm.

FIG. 3 illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave.

It may be appreciated that, in other embodiments, other waveforms may be used, such as a train of pure monophasic pulses (e.g., a sequence of short (<10 μs) or long (>10 μs) pulses is delivered with relatively long (>1 ms) delays between them, all of the same polarity), alternating monophasic (e.g., a sequence of long pulses is delivered with relatively long delays between them, with alternating polarity), and biphasic (where pulses are delivered with relatively brief delays (<1 ms) between changes in polarity), to name a few. Likewise, when packets are present, packets may be bundled with delays therebetween. Similarly, delays may be present within packets, such as cycle delays or phase delays.

It may be appreciated that in some embodiments, the generator 104 is comprised of three sub-systems; 1) a high energy storage system, 2) a high voltage, medium frequency switching amplifier, and 3) the system control, firmware, and user interface. The system controller includes a cardiac synchronization trigger monitor that allows for synchronizing the pulsed energy output to the patient's cardiac rhythm. The generator takes in AC (alternating current) mains to power multiple DC (direct current) power supplies. The generator's controller instructs the DC power supplies to charge a high-energy capacitor storage bank before energy delivery is initiated. At the initiation of therapeutic energy delivery, the generator's controller, high-energy storage banks and a bi-phasic pulse amplifier operate simultaneously to create a high-voltage, medium frequency output.

The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

The user interface 150 can include a touch screen and/or more traditional buttons to allow for the operator to enter patient data, select a treatment algorithm (i.e., energy delivery algorithm 152), initiate energy delivery, view records stored on the storage/retrieval unit 156, or otherwise communicate with the generator 104.

Any of the systems disclosed herein can include a user interface 150 configured to allow operator-defined inputs. The operator-defined inputs can include duration of energy delivery or other timing aspects of the energy delivery pulse, power, target temperature, mode of operation, or a combination thereof. For example, various modes of operation can include system initiation and self-test, operator input, algorithm selection, pre-treatment system status and feedback, energy delivery, post energy delivery display or feedback, treatment data review and/or download, software update, or a combination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. Here, the cardiac monitor 170 is used to continuously acquire the ECG. External electrodes 172 may be applied to the patient P and to acquire the ECG. The generator 104 analyzes one or more cardiac cycles and identifies the beginning of a time period where it is safe to apply energy to the patient P, thus providing the ability to synchronize energy delivery with the cardiac cycle. In some embodiments, this time period is within milliseconds (ms) of the R wave to avoid induction of an arrhythmia which may occur if the energy pulse is delivered on a T wave. It may be appreciated that such cardiac synchronization is typically utilized when using monopolar energy delivery, however it may be utilized in other instances.

In some embodiments, the processor 154, among other activities, modifies and/or switches between the energy-delivery algorithms, monitors the energy delivery and any sensor data, and reacts to monitored data via a feedback loop. It may be appreciated that in some embodiments the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data related to the treatments delivered and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154. Examples algorithms will be described in detail herein below. In some embodiments, the catheter 102 includes one or more sensors 160 that can be used to determine temperature, impedance, resistance, capacitance, conductivity, permittivity, and/or conductance, to name a few. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It may be appreciated that any of the systems disclosed herein can include an automated treatment delivery algorithm that could dynamically respond and adjust and/or terminate treatment in response to inputs such as temperature, impedance, treatment duration or other timing aspects of the energy delivery pulse, treatment power and/or system status.

In some embodiments, imaging is achieved with the use of a commercially-available system, such as a bronchoscope 112 connected with a separate imaging screen 180, as illustrated in FIG. 1. It may be appreciated that imaging modalities can be incorporated into the catheter 102 or used alongside or in conjunction with the catheter 102. The imaging modality can be mechanically, operatively, and/or communicatively coupled to the catheter 102 using any suitable mechanism.

Figure 4:
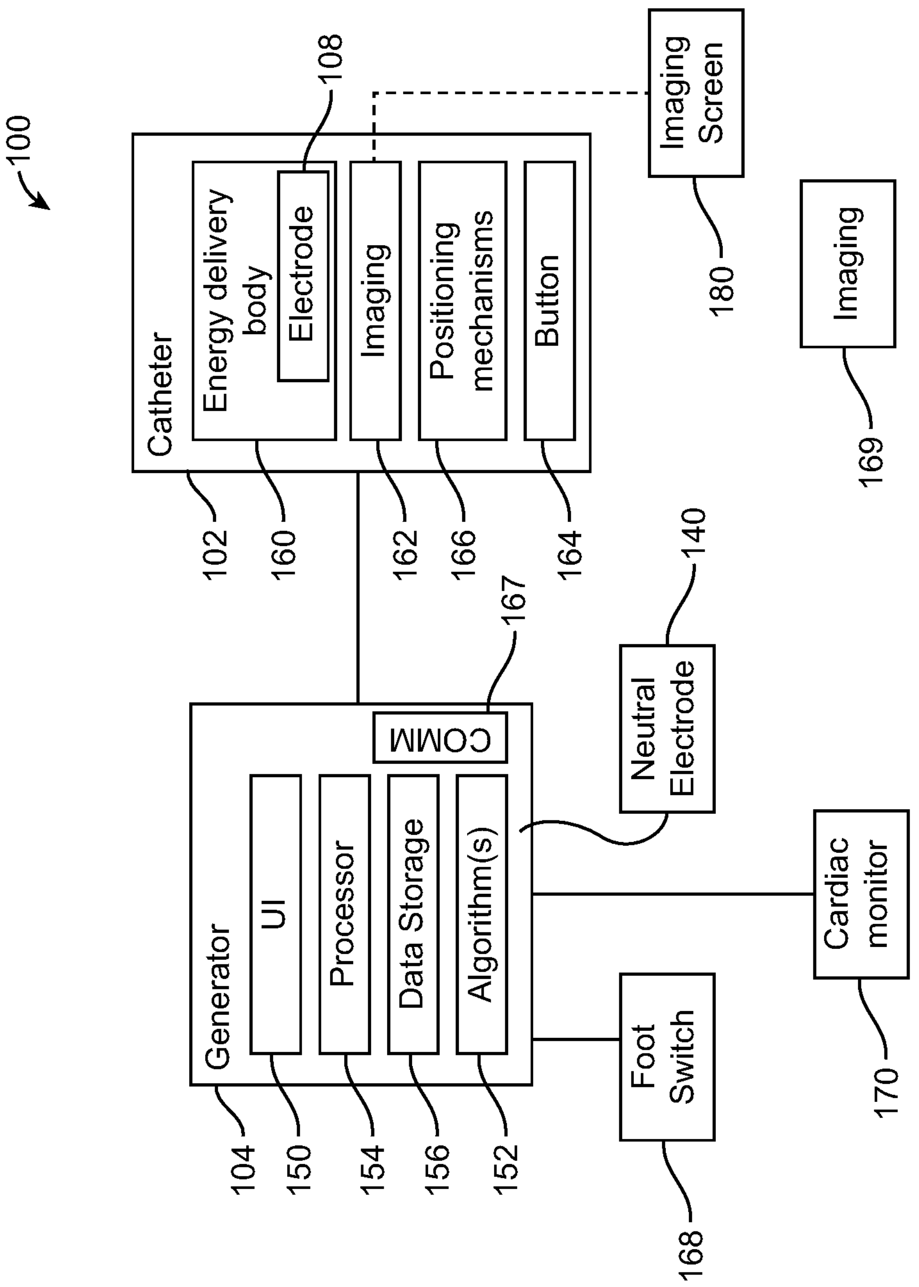
FIG. 4 is a schematic illustration of an embodiment of a pulmonary tissue modification system.

FIG. 4 is a schematic illustration of an embodiment of a pulmonary tissue modification system 100. In this embodiment, the catheter 102 is configured for monopolar energy delivery. As shown, a dispersive (neutral) or return electrode 140 is operatively connected to the generator 104 while affixed to the patient's skin to provide a return path for the energy delivered via the catheter 102. The energy-delivery catheter 102 includes one or more energy delivery bodies 108 (comprised of electrode(s)), one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like). The one or more energy delivery bodies 108 can be configured to come into contact with the tissue. In some embodiments, a foot switch 168 is operatively connected to the generator 104 and used to initiate energy delivery.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The catheter 102 is operatively connected to the generator 104 and/or a separate imaging screen 180. Imaging modalities 162 can be incorporated into the catheter 102 or used alongside or in conjunction with the catheter 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the catheter 102 using any suitable mechanism.

Impedance Measurements

Figure 5:
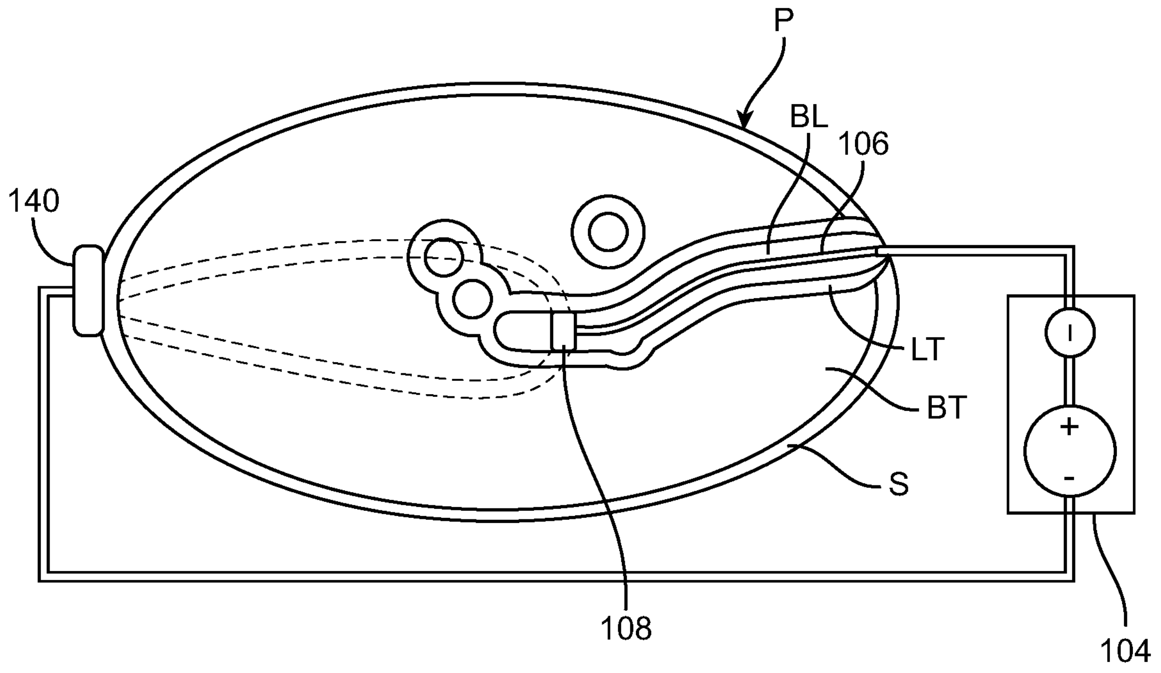
FIG. 5 provides a schematic illustration of monopolar energy delivery to a patient, such as according to FIG. 1 wherein the patient is illustrated as an oval mass having an internal body lumen.

FIG. 5 provides a schematic illustration of monopolar energy delivery to a patient P, such as according to FIG. 1. Here, the patient P is illustrated as an oval mass having an internal body lumen BL which represents a lung airway. It may be appreciated that in other embodiments the body lumen BL represents a different type of lumen within the body. The shaft 106 of the catheter 102 is inserted into the body lumen BL so that the energy delivery body 108 is positioned therein. When energy is delivered from the energy delivery body 108, the energy travels through various interfaces and tissue layers (indicated by dashed lines) to the dispersive electrode 140 positioned outside of the body and against the skin S. In particular, the energy flows through the interface of the energy delivery body 108 (e.g., electrode) and the local tissue LT (e.g., airway wall), through the local tissue LT, through the internal body tissue BT, through the skin S, and through the interface of the dispersive electrode 140 and the skin S. The dispersive electrode 140 has a broad contact area which draws the energy over a large area. Thus, a large portion of the patient's body serves as an electrical conduit, diluting the treatment intensity to sub-therapeutic levels throughout the body mass. The overall tissue system electrical properties and metrics includes the relatively small volume of affected or treated tissues and the much larger volume of unaffected tissues from the bulk of the body. Consequently, discerning the presence and amount of local effects in a measurable way is very difficult due to its comparatively small proportion.

One electrical property that has been used to characterize tissue effects is impedance. Impedance is a measure of the tissue's opposition to the flow of alternating electric currents of various frequencies. The patient's body is comprised of a variety of types of tissue in a very complex structure, and each tissue is comprised of a three-dimensional arrangement of biological cells. The biological cells, containing intracellular fluids and cell membranes, are suspended in the extracellular fluids and extracellular matrix of proteins, and show a frequency dependent behavior to an alternating electrical signal. Under an alternating electrical excitation, the biological cells and tissues produce a complex bioelectrical impedance or electrical bioimpedance which depends on tissue composition and frequency of the applied signal. Therefore, the frequency response of the electrical impedance of the biological tissues is highly influenced by their physiological and physiochemical status and varies from subject to subject, tissue to tissue, and physiological and physiochemical changes due to treatment and other effects. Hence, the measurements of complex bioimpedance of a tissue can provide information about its status, including its treatment status. Thus, impedance can be used in real-time monitoring of tissue at various times during treatment.

Electrical impedance of a particular tissue can be estimated by measuring the voltage signal developed across the tissue when a current signal is provided to the tissue. Mathematically, the impedance (Z) is measured by dividing the voltage signal measured (V) by the current signal applied (I). Impedance (Z) is a complex quantity and it will have a particular phase angle (θ) depending on the tissue properties. In electrical impedance tomography measurements, the bioelectrical impedance of a body tissue is measured by injecting a low amplitude low frequency alternating current to the tissue through an array of surface electrodes attached to the tissue surface (tissue boundary). Since cell membranes behave as electric capacitors, the electrical properties of biological tissue at low frequencies (ideally between 10 Hz and 10 kHz) will show the highest sensitivity to physiological changes of the cell membranes. The changes induced at the cell membrane using pulse electric field technologies will have an impact on its capacitive behavior, and thus, will affect the impedance at these low frequencies. However, some pulsed electric field treatments use high frequency signals (ideally greater than or equal to 100 kHz), such as to avoid or reduce undesired electrical stimulation of muscle tissue. At this range of high frequencies, the intrinsic impedance of the conventional dispersive electrodes can be disregarded. However, if the same electrodes are intended to be used for low frequency signals, such as the ones more sensible to detect cell membrane changes, the intrinsic dispersive electrode impedance can significantly affect the overall measured impedance value(s). This undesired interference can prevent the detection of the capacitive behavior of the tissue, and thus, small changes of the tissue properties at the region of interest will not be detectable. This is illustrated in FIG. 6A.

FIG. 7 provides a model of the impedances encountered in FIG. 5 when measuring the voltage signal developed across the tissue. The measured impedance is comprised of at least five individual impedances which can be identified as the delivery electrode impedance $Z_e$ (related to the interface of the energy delivery body 108 with local tissue LT), local tissue impedance $Z_{LT}$, internal body tissue impedance $Z_{BT}$, skin impedance $Z_S$, and the dispersive electrode impedance $Z_{de}$ (related to the interface of the dispersive electrode 140 and skin S). Typically, the skin impedance $Z_S$ and the dispersive electrode impedance $Z_{de}$ are disproportionately large, overwhelming the other measurements. Therefore, it is desired to minimize these impedances (i.e., to minimize the skin impedance $Z_S$ and the dispersive electrode impedance $Z_{de}$) to allow identification of changes in the other impedance values, such as, and most importantly, changes to the local tissue impedance $Z_{LT}$.

Figure 8:
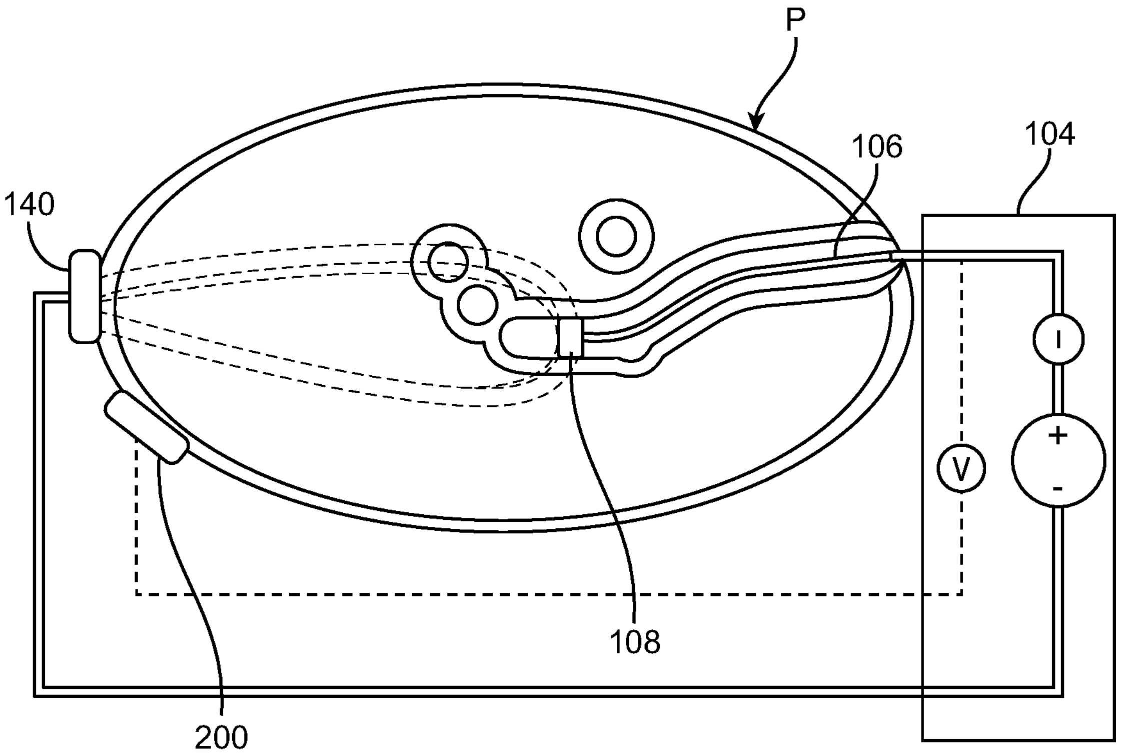
FIG. 8 illustrates positioning a reference electrode against the skin on the outside of the body of the patient.

In some embodiments, such minimization is achieved with the use of a reference electrode 200 positioned against the skin S on the outside of the body of the patient P, as illustrated in FIG. 8. Again, the patient P is illustrated as an oval mass with the same tissues and interfaces as illustrated in FIG. 5. When energy is delivered from the energy delivery body 108 during treatment, the energy travels through various interfaces and tissue layers (indicated by dashed lines) to the dispersive electrode 140.

The reference electrode 200 is used to measure the induced voltage when electric current signals are injected between the energy delivery body 108 and the dispersive electrode 140. Using the measurements setup described herein, the absence of current flowing towards the reference electrode 200 minimizes the sensitivity of measurements around the dispersive electrode 140, as illustrated in FIG. 6B. Thus, FIGS. 6A-6B show the impedance measurements performed on a same tissue sample using a conventional two electrode method (FIG. 6A) and using a multi-electrode (3 electrode) method (FIG. 6B) according to an embodiment of the present technology described herein. The conventional two electrode method refers to using only the energy delivery body 108 and the dispersive electrode 140 to obtain impedance measurements. By contrast, the multi-electrode (3 electrode) method refers to using the energy deliver body 108 and the dispersive electrode 140 to deliver an impedance measurement signal, and using the energy delivery body 108 and the reference electrode 200 to obtain one or more impedance measurements. Unlike the conventional 2 electrode method, the multi-electrode method allows one to observe the characteristic semicircle shape of a NYQUIST-plot (also known as a Cole-Cole plot) of biological tissues corresponding to the capacitive behavior of the cell membranes.

The dispersive electrode 140 is a type of return electrode that is used together with the energy delivery body 108 to deliver treatment energy, such as pulsed electric field (PEF) energy or RF energy to target tissue. The energy delivery body 108 includes one or more energy delivery electrodes (also known as active electrodes) that are configured (e.g., sized) to deliver treatment therapy to tissue proximate to the energy deliver body 108, or more specifically, proximate to the one or more energy delivery electrodes thereof. By contrast, the dispersive electrode 140, which can also be referred to as an indifferent electrode, is an electrode (e.g., configured to be placed on patient skin) that is larger than the energy delivery electrode(s) and configured (e.g., sized) to contribute little or nothing to the treatment delivered between the energy delivery electrode(s) of the energy delivery body 108 and the dispersive electrode 140. In other words, it is intended for there to be little or no treatment effects responsive to a treatment signal on the patient tissue (e.g., skin) that is in contact with the dispersive electrode 140. In order to increase the probability of the dispersive electrode 140 contributing little or nothing to the treatment delivered between the energy delivery electrode(s) of the energy delivery body 108 and the dispersive electrode 140, the dispersive electrode 140 should have a surface area that is at least twice (i.e., 2×) the surface area of an individual energy deliver electrode, and preferably has a surface area that is at least ten times (i.e., 10×) the surface area of an individual energy delivery electrode, and ideally has a surface area that is at least one hundred times (i.e., 100×) the surface area of an individual energy delivery electrode. More generally, the larger the surface area of the dispersive electrode 140 relative to the surface area of the energy delivery electrode(s) of the energy delivery body 108, the better.

Figure 9:
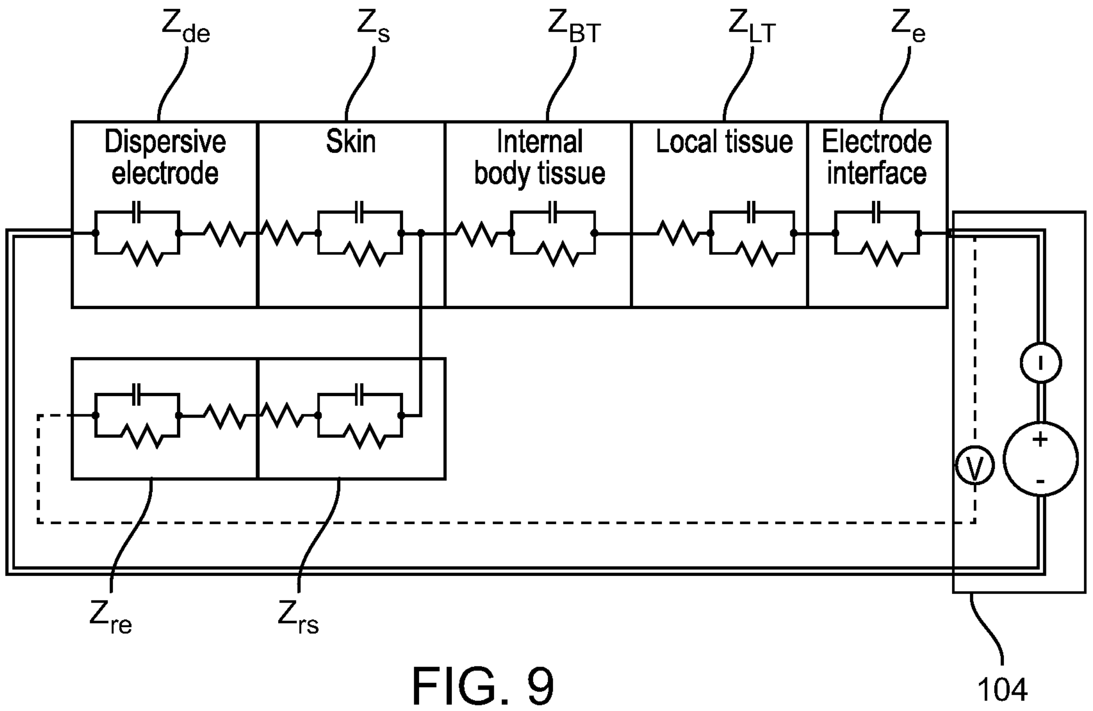
FIG. 9 provides a model of the impedances encountered in FIG. 8.

FIG. 9 provides a model of the impedances encountered in FIG. 8. As mentioned previously, measuring the voltage signal developed across the tissue provides at least the following impedances: delivery electrode impedance $Z_e$ (related to the interface of the energy delivery body 108 with local tissue LT), local tissue impedance $Z_{LT}$, internal body tissue impedance $Z_{BT}$, skin impedance $Z_S$, and the dispersive electrode impedance $Z_{de}$. The absence of current flowing through the reference electrode impedance Z re and reference skin impedance $Z_{rS}$ implies that the measured potential will be independent to the dispersive electrode impedance $Z_{de}$ and the skin impedance, $Z_S$. Consequently, the overwhelming values of these impedances can be minimized, elucidating the impedances of interest, such as local tissue impedance $Z_{LT}$.

In some instances, the measured values may still be influenced by electric properties of tissue outside of the area of interest (e.g., resulting from breathing, movements, etc.). By monitoring the treatment effects assessing only the impedances at low frequencies, an unrelated change affecting tissue outside the treatment area could potentially induce a misinterpretation of the measured data. For instance, pulmonary parenchyma shows a higher conductivity during exhalation (compared to during inhalation) since the air content decrease. At the same time, the therapeutic pulses will increase the affected tissue conductivity. According to that, performing an impedance measurement during the exhalation of the patient can be misinterpreted as a successful treatment insight. In order to obtain a treatment effect metric resilient to macroscopic patient changes, an empirical impedance-based indicator (IBI) is provided as a more robust metric related to the changes induced by the pulse electric field treatments.

In accordance with certain embodiments of the present technology, the IBI is generated using the following equation:

$$IBI=(\angle Z_{LF}(t)-\angle Z_{LF}(0))\cdot|Z_{HF}|$$

where $\angle Z_{LF}(0)$ is a low frequency impedance phase angle value measured at a time t=0 prior to a treatment signal being delivered, $\angle Z_{LF}(t)$ is a low frequency impedance phase angle value measured at a time t after the treatment signal was delivered, and $Z_{HF}$ is a high frequency impedance magnitude value measured before or after the treatment signal was delivered.

Figure 10:
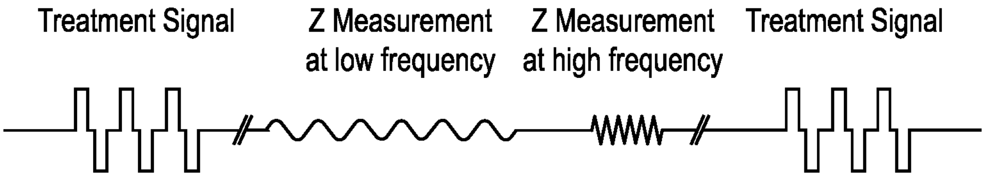
FIG. 10 illustrates taking low frequency and high frequency impedance measurements between the delivery of treatment signals.

The impedance phase angle of a biological tissue ($\angle Z$) is highly correlated to the capacitive behavior of the cell membranes of the biological tissue. The provided metric uses an initial impedance phase angle value $\angle Z_{LF}(0)$, measured at t=0 that is before delivering the therapeutic energy (e.g., a monopolar treatment signal), which is used to monitor a reduction of the impedance phase over the time (t). The successive phase angle impedance measurement at a low frequency (i.e., $\angle Z_{LF}(t)$) and impedance magnitude measurement at a high frequency (i.e., $Z_{HF}$) should also be obtained. More specifically, FIG. 10 shows delivery of a treatment signal, followed by delivery of an impedance measurement signal, followed by delivery of another treatment signal. In the example of FIG. 10, the impedance measurement signal (which can also be referred to as a Z measurement signal), which is given that name because it is used to measure the impedance of target tissue, includes a low frequency portion (labeled Z Measurement at low frequency) that temporally precedes a high frequency portion (labeled Z Measurement at high frequency). However it is noted that the impedance measurement signal can alternatively include a high frequency portion that temporally precedes the low frequency portion. In accordance with certain embodiments, delivery of the impedance measurement signal includes delivery of a low frequency current signal during which a low frequency impedance phase measurement (i.e., $\angle Z_{LF}(t)$) is obtained, followed by delivery of a high frequency current signal during which a high frequency impedance magnitude measurement (i.e., $Z_{HF}$) is obtained. In other words, the impedance measurement signal includes a low frequency portion (e.g., a low frequency current signal) and a high frequency portion (e.g., a high frequency current signal), wherein the low frequency portion of the impedance measurement signal temporally precedes the high frequency portion of the impedance measurement signal, or vice versa. In FIG. 10, the impedance measurement signal is shown as being delivered between the delivery of a pair of treatment signals. While not specifically shown in FIG. 10, an instance of the impedance measurement signal can also be delivered to target tissue prior to the delivery of any treatment signal to that target tissue, to thereby enable a baseline impedance measurement to be obtained for the target tissue. The impedance phase angle value $\angle Z_{LF}(0)$, measured at t=0 that is before delivering the therapeutic energy (e.g., a monopolar treatment signal), is an example of the baseline impedance measurement.

The terms low frequency (LF) and high frequency (HF), as used herein to refer to the frequencies of signals, are terms that are relative to one another. More specifically, as the terms are used herein, a high frequency signal has a frequency that is at least two times (i.e., 2×) the frequency of a low frequency signal, is preferably at least ten times (i.e., 10×) the frequency of the low frequency signal, and ideally is at least one hundred times (i.e., 100×) the frequency of the low frequency signal. As explained above with reference to FIG. 10, the impedance measurement signal that is used in accordance with certain embodiments of the present technology includes a low frequency portion and a high frequency portion, wherein the low frequency portion of the impedance measurement signal temporally precedes the high frequency portion of the impedance measurement signal, or alternatively, the high frequency portion of the impedance measurement signal temporally precedes the low frequency portion of the impedance measurement signal. More specifically, a low frequency portion of an impedance measurement signal can be within the range of 1 Hz to 200 MHz, is preferably within the range of 1 Hz to 100 kHz, and is ideally within the range of 10 Hz to 10 kHz. A high frequency portion of an impedance measurement signal can be within the range of 50 kHz to 1 GHz, is preferably within the range of 50 kHz to 200 MHz, and is ideally within the range of 100 kHz and 3 MHz.

Figure 11:
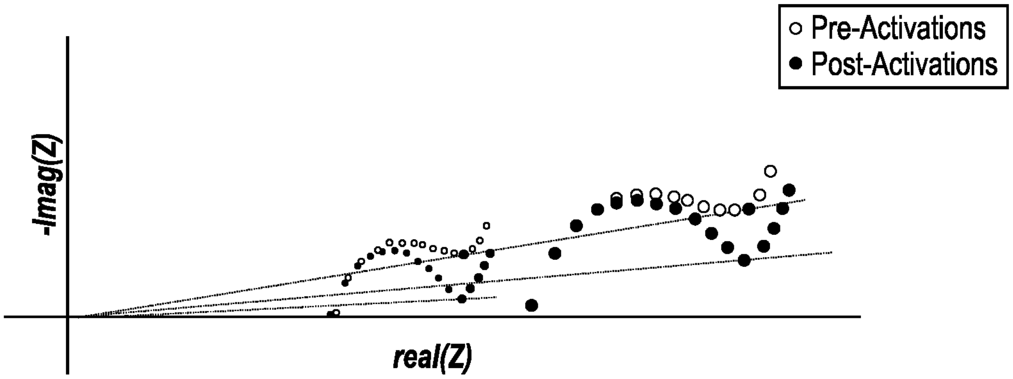
FIG. 11 shows a Wessel impedance plot of two different tissues where a low frequency impedance value, before and after therapeutic treatment is performed.

As stated before, a sudden change of the impedance outside the region of interest (i.e., outside the local tissue LT) could also affect the measured impedance magnitudes. FIG. 11 shows the Wessel impedance plot of two different tissues (left and right) where a low frequency impedance value (dots), before (circle dots) and after (solid dots) therapeutic treatment is performed. Under the same treatment intensity, in case of a general body impedance the phase (dashed line angle) change is relatively lower than in case of lower body impedance.

In order to scale the phase changes to the bulky body impedance, the relative change of phase between a most recent impedance phase measurement (i.e., $\angle Z_{LF}(t)$) and the basal phase value (i.e., $\angle Z_{LF}(0)$) is scaled by the current impedance magnitude at a high frequency (i.e., $Z_{HF}$), which is a value relatively insensitive to changes induced by the treatment. Since the current impedance magnitude of target tissue at the high frequency (i.e., $Z_{HF}$) should be unaffected by a treatment signal, the current impedance magnitude of target tissue at the high frequency (i.e., $Z_{HF}$) can either be measurement before the delivery of a treatment signal to target tissue, or following the delivery of a treatment signal to the target tissue.

In accordance with certain embodiments, a magnitude of the monopolar treatment signal should be at least ten times (i.e., 10×) the magnitude of the impedance measurement signal, and ideally is at least fifty times (i.e., 50×) the magnitude of the impedance measurement signal. For an example, the magnitude of the monopolar treatment signal can be within the range of 1000 V to 5000 V (e.g., 3000 V), and the magnitude of the impedance measurement signal can be within the range of 0.1 V to 100 V (e.g., 1 V).

Figure 12A:
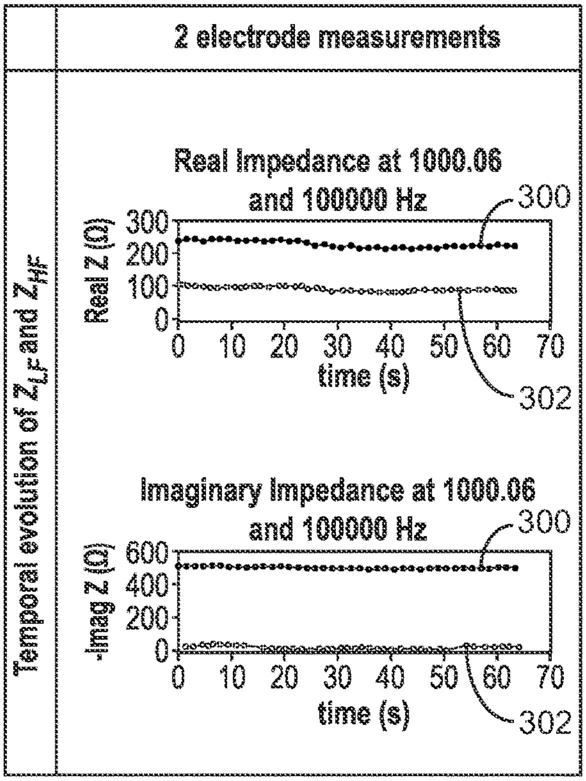
FIGS. 12A-12B illustrate the temporal evolution of the impedance values at low frequency and high frequency over the application of therapeutic pulses.
Figure 12B:
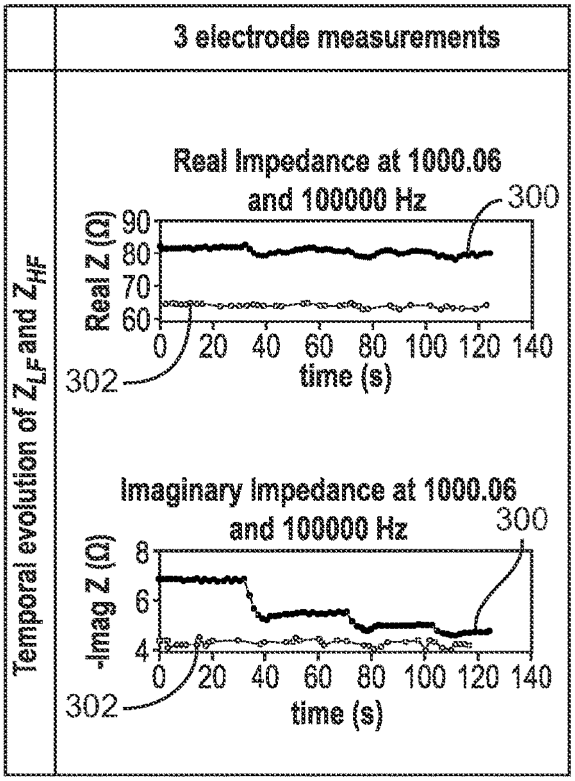

FIGS. 12A-12B show the temporal evolution of the impedance values at low frequency 300 and high frequency 302 over the application of therapeutic pulses. FIG. 12A shows the measurements using a typical two (2) electrode setup and FIG. 12B shows the measured values using the 3 electrode setup described herein.

Figure 13A:
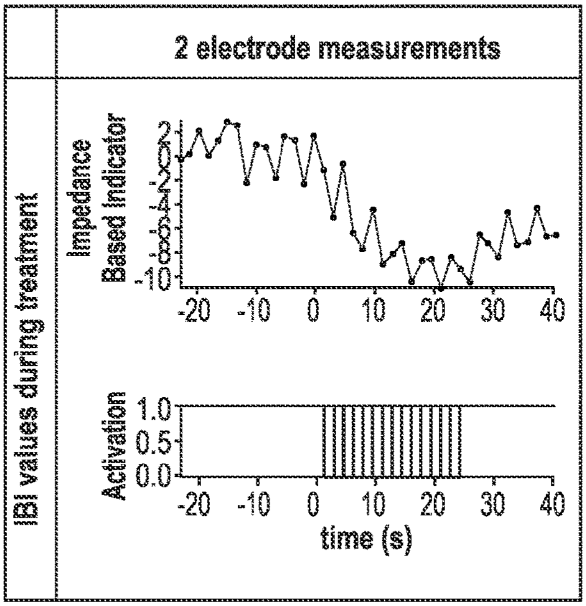
FIGS. 13A-13B illustrate the impedance-based indicator (IBI) evolution after delivering therapeutic treatments in measurements using a typical 2 electrode setup and using an embodiment of the 3 electrode setup described herein.
Figure 13B:
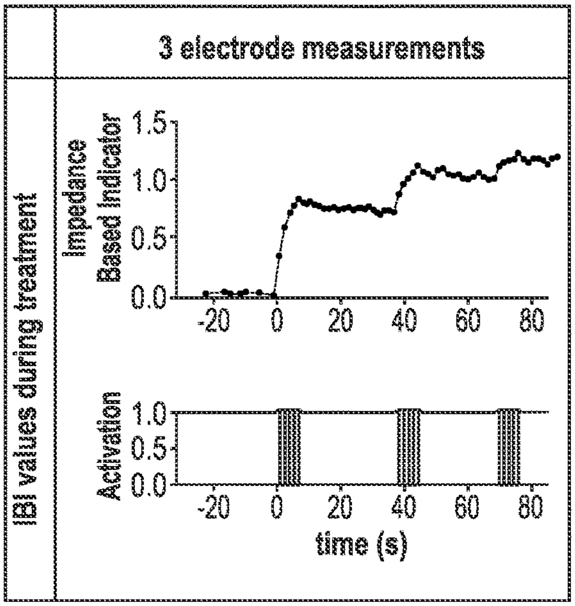

FIGS. 13A-13B denotes the IBI evolution after delivering therapeutic treatments in measurements using a typical two (2) electrode setup (FIG. 13A) and using the three (3) electrode setup described herein (FIG. 13B).

Additional Reference Electrode Embodiments

Figure 14:
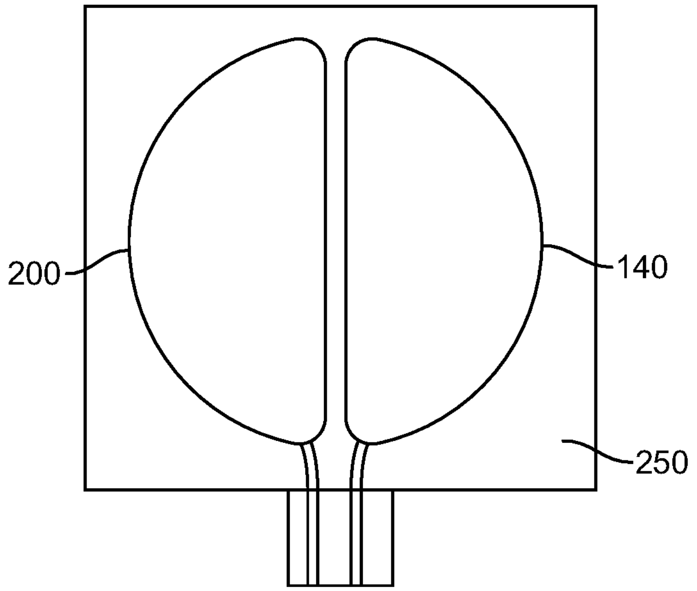
FIG. 14 illustrate the reference electrode and dispersive electrode formed together in a single pad.

It may be appreciated that the reference electrode 200 may be positioned in a variety of alternative locations. In one embodiment, the reference electrode 200 and dispersive electrode 140 are formed together in a single pad, such as illustrated in FIG. 14. Here, each electrode 200, 140 is comprised of a layer of electrically conductive material, and both electrodes 200, 140 are disposed on a single sheet or pad 250, yet are electrically isolated from one another. This allows the pad 250 to be affixed to the patient's skin S in a single action for convenience. Typically, the pad 250 is covered by an electrolyte gel which makes contact with the skin S. Thus, using a dual electrode uses less gel and requires less clean up. Using this approach, one of the electrodes would be employed as a dispersive electrode 140 for the current injection (i.e., for the delivery of impedance measurement signal) and the other electrode would be employed as a reference electrode 200 to monitor the induced voltage and the corresponding impedance as described by the main embodiment.

Figure 15:
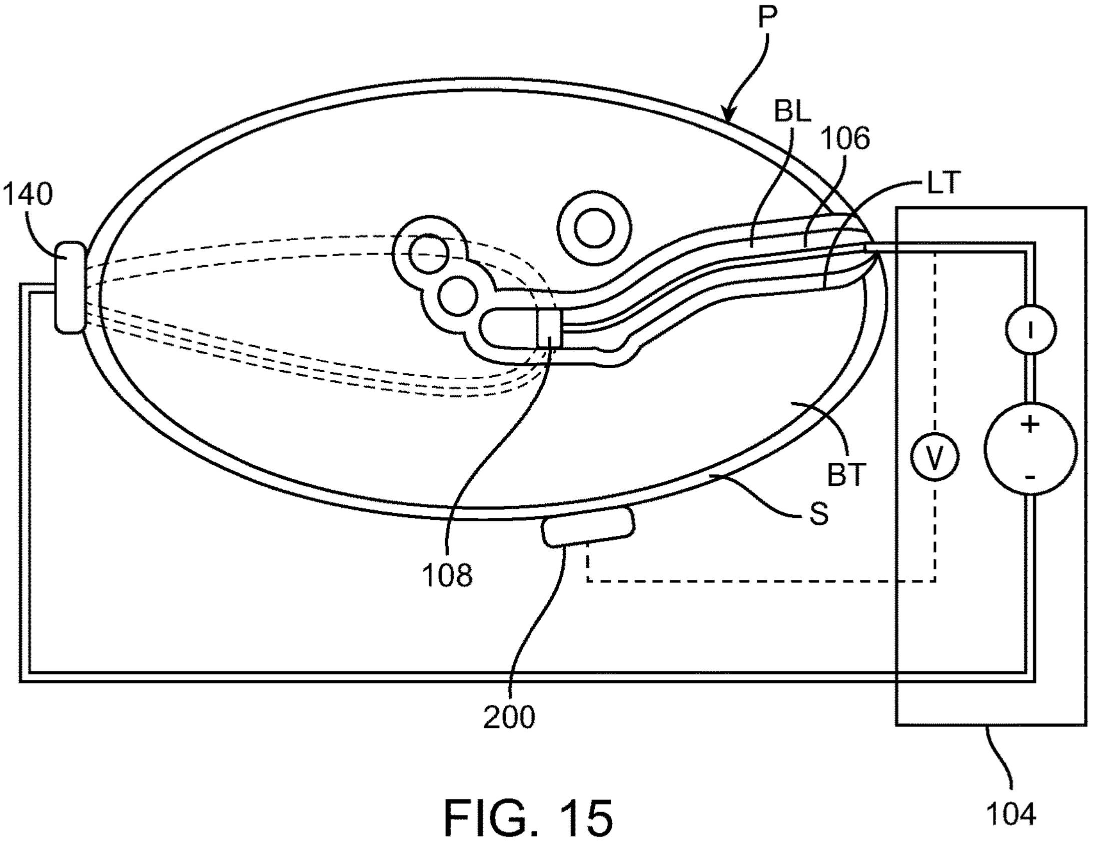
FIG. 15 illustrates an embodiment wherein the reference electrode is positioned against the skin of the patient at a location closer to the energy delivery body.

In other embodiments, the reference electrode 200 is positioned closer to the treatment area than the dispersive electrode 140. For example, FIG. 15 illustrates an embodiment wherein the reference electrode 200 is positioned against the skin S of the patient at a location closer to the energy delivery body 108 than the dispersive electrode 140. Again, the patient P is illustrated as an oval mass with the same tissues and interfaces as illustrated in FIG. 5. When energy is delivered from the energy delivery body 108 during treatment, the energy travels through various interfaces and tissue layers (indicated by dashed lines) to the dispersive electrode 140. The reference electrode 200 is used to detect the voltage drop during periods when treatment energy is not present and energy designed for impedance measurement is used.

Figure 16:
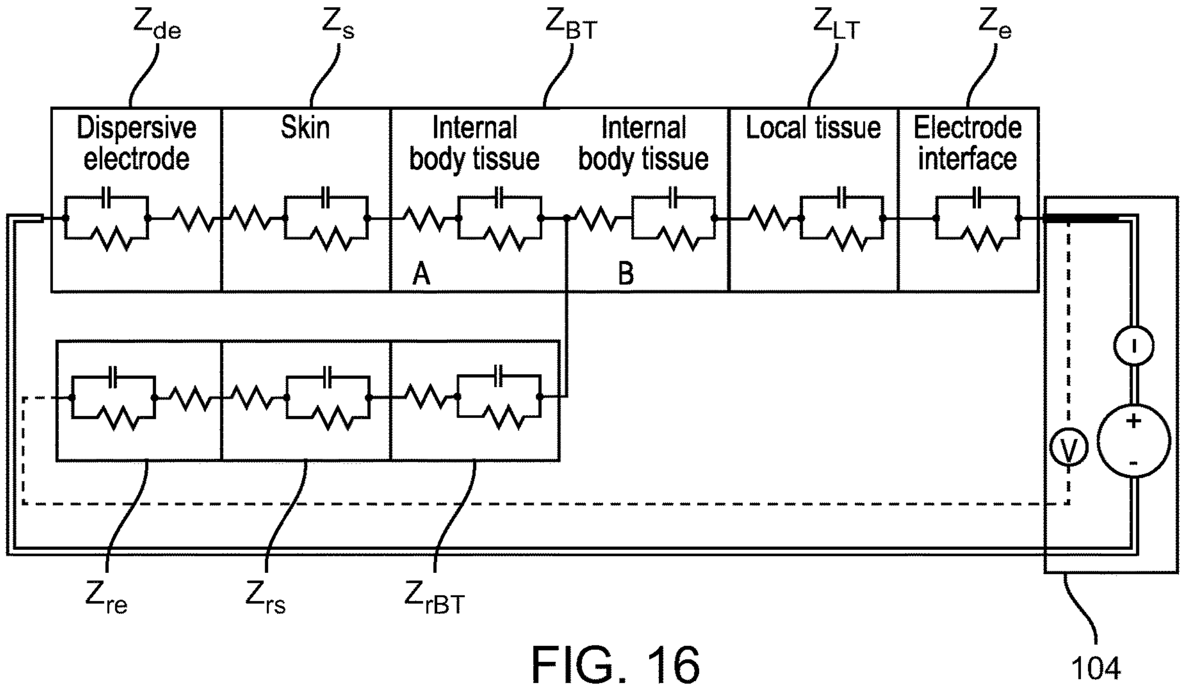
FIG. 16 provides a model of the impedances encountered in FIG. 15.

FIG. 16 provides a model of the impedances encountered in FIG. 15. As mentioned previously, measuring the voltage signal developed across the tissue provides at least the following impedances: delivery electrode impedance $Z_e$ (related to the interface of the energy delivery body 108 with local tissue LT), local tissue impedance $Z_{LT}$, internal body tissue impedance $Z_{BT}$, skin impedance $Z_S$, and the dispersive electrode impedance $Z_{de}$ (related to the interface of the dispersive electrode 140 and skin S). Measuring the voltage signal at the reference electrode 200 provides a reference electrode impedance $Z_{re}$, a reference skin impedance $Z_{rS}$ and a reference internal body tissue impedance $Z_{rBT}$ which can account for the dispersive electrode impedance $Z_{de}$, the skin impedance $Z_S$, and a portion of the internal body tissue impedance $Z_{BT}$. Consequently, the overwhelming values of these impedances can be minimized, elucidating the impedances of interest, such as local tissue impedance $Z_{LT}$.

Figure 17:
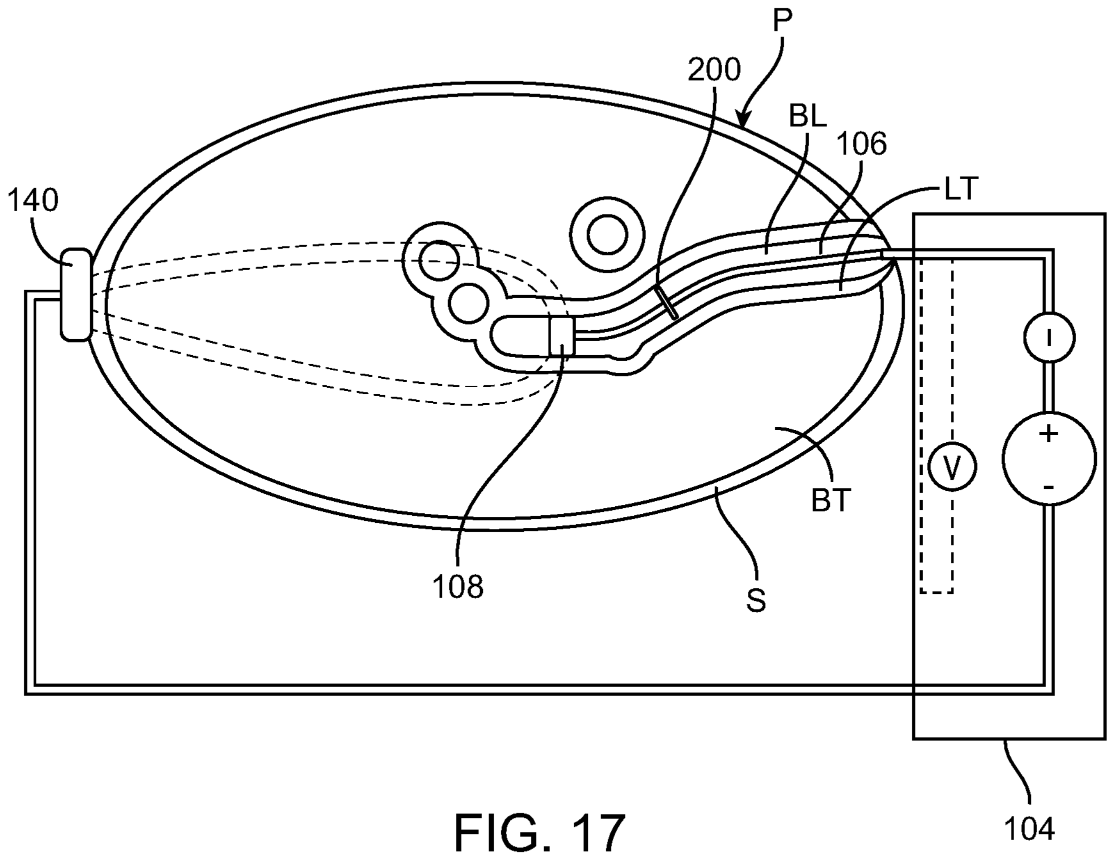
FIG. 17 illustrates an embodiment wherein the reference electrode is disposed along the shaft of the catheter so that it resides within the body lumen.

In other embodiments, the reference electrode 200 is positioned internally, such as near, within or adjacent to the treatment area (i.e., near, within or adjacent to the local tissue). For example, FIG. 17 illustrates an embodiment wherein the reference electrode 200 is disposed along the shaft 106 of the catheter 102 so that it resides within the body lumen BL. Again, the patient P is illustrated as an oval mass with the same tissues and interfaces as illustrated in FIG. 5. When energy is delivered from the energy delivery body 108 during treatment, the energy travels through various interfaces and tissue layers (indicated by dashed lines) to the dispersive electrode 140. The reference electrode 200 is used to detect the voltage drop during periods when treatment energy is not present and energy designed for impedance measurement is used.

Figure 18:
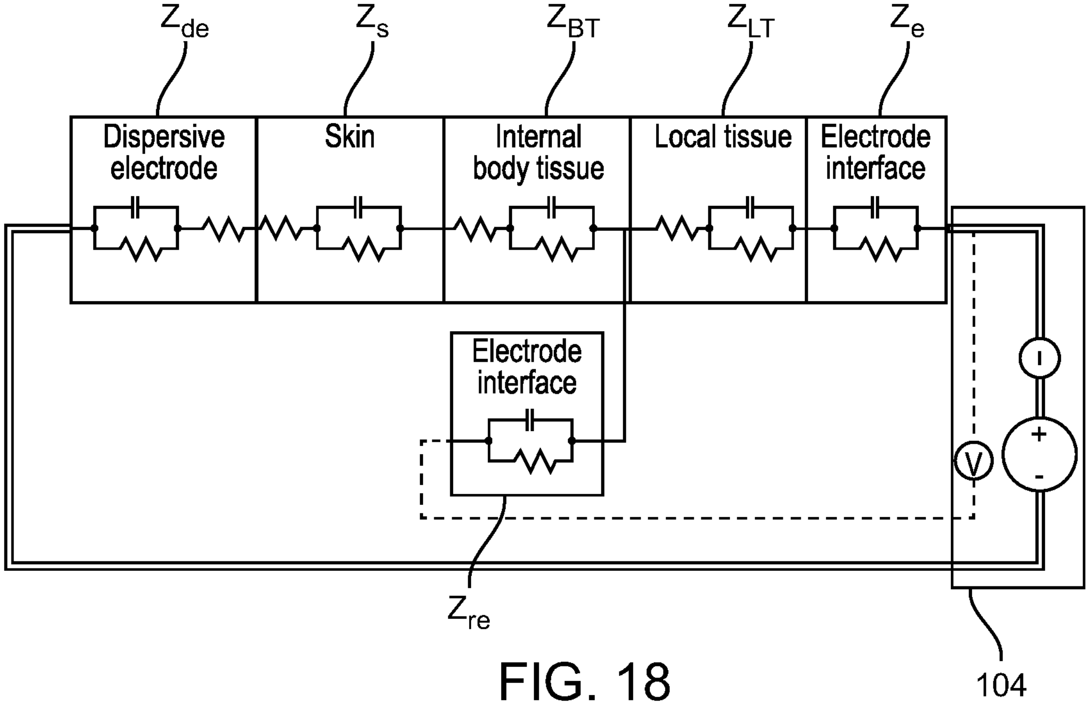
FIG. 18 provides a model of the impedances encountered in FIG. 17.

FIG. 18 provides a model of the impedances encountered in FIG. 17. As mentioned previously, measuring the voltage signal developed across the tissue provides at least the following impedances: delivery electrode impedance $Z_e$ (related to the interface of the energy delivery body 108 with local tissue LT), local tissue impedance $Z_{LT}$, internal body tissue impedance $Z_{BT}$, skin impedance $Z_S$, and the dispersive electrode impedance $Z_{de}$ (related to the interface of the dispersive electrode 140 and skin S). Measuring the voltage signal at the reference electrode 200 provides a reference electrode impedance $Z_{re}$, which can account for the delivery electrode impedance $Z_e$. Consequently, the performed measurements will be insensitive to potential internal body tissue impedances $Z_{BT}$, thus, increasing the sensitivity of the performed measurements to changes at the local tissue.

It may be appreciated that the reference electrode 200 may be mounted on the outside of the catheter 102 or integral with the catheter 102. Likewise, the reference electrode 200 may be mounted on or integral with a device which is passed through a lumen in the catheter 102. For example, the reference electrode 200 may be disposed on a guidewire which is passable through at least a portion of the catheter 102 so as to position the reference electrode 200 near the treatment area.

Figure 19:
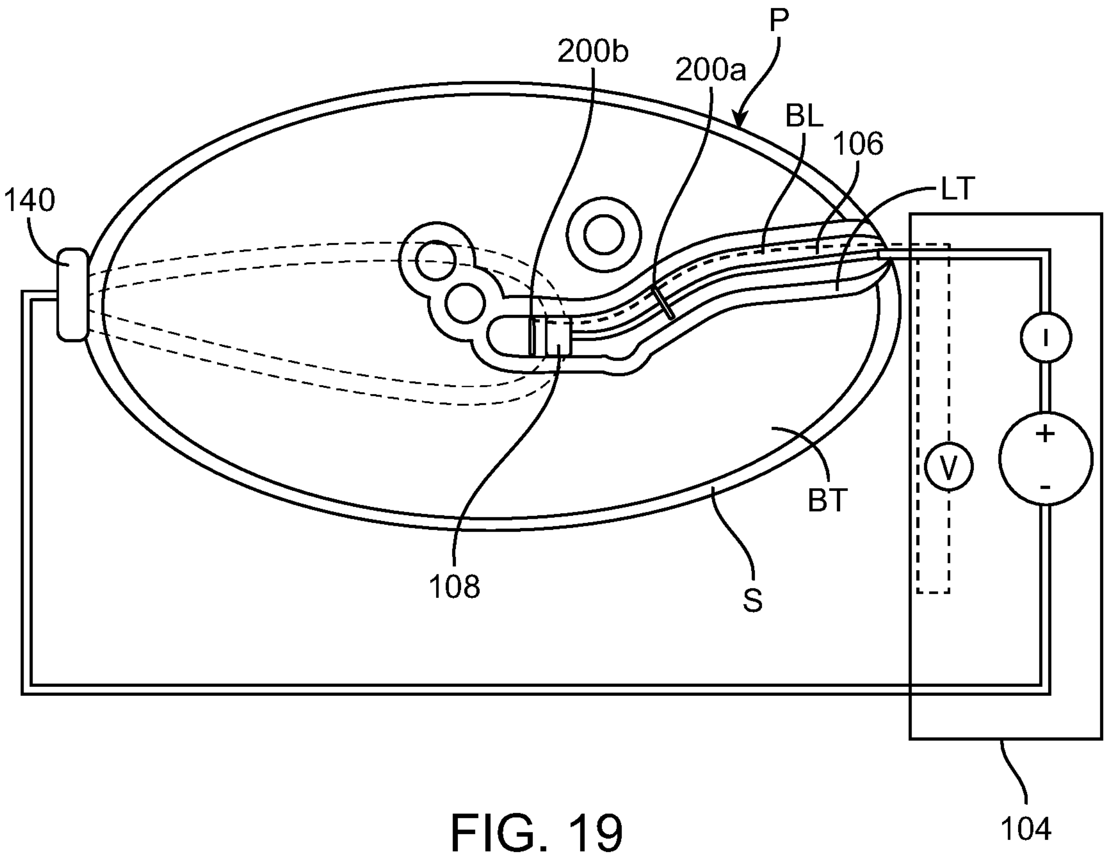
FIG. 19 illustrates an embodiment wherein the first reference electrode is disposed along the shaft proximally of the energy delivery body and the second reference electrode is disposed along the shaft distally of the energy delivery body.

In other embodiments, two reference electrodes (a first reference electrode 200*a* and a second reference electrode 200*b*) are positioned internally, such as near, within or adjacent to the treatment area. For example, FIG. 19 illustrates an embodiment wherein the first reference electrode 200*a* is disposed along the shaft 106 proximally of the energy delivery body 108 and the second reference electrode 200*b* is disposed along the shaft 106 (or on a guide wire) distally of the energy delivery body 108. When energy is delivered from the energy delivery body 108 during treatment, the energy travels through various interfaces and tissue layers (indicated by dashed lines) to the dispersive electrode 140. The reference electrodes 200*a*, 200*b* are used to detect the voltage drop therebetween during periods when treatment energy is not present and energy designed for impedance measurement is used (i.e., when the impedance measurement signal is delivered using the energy delivery body 108 and the dispersive electrode 140).

Figure 20:
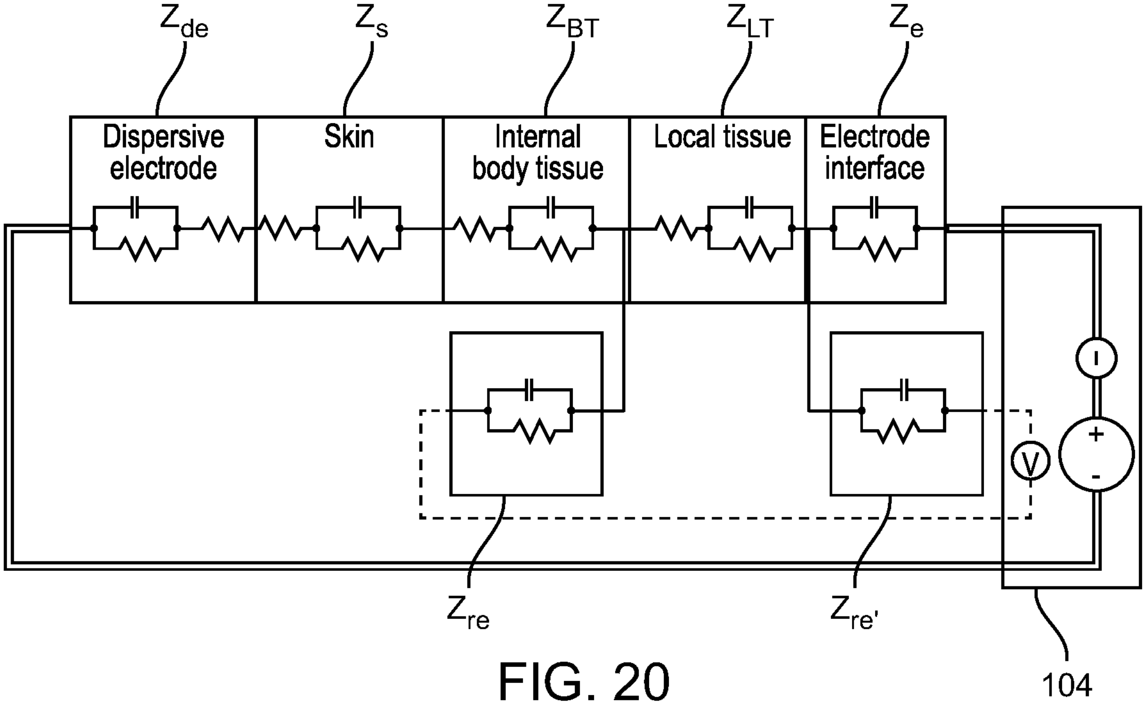
FIG. 20 provides a model of the impedances encountered in FIG. 19.

FIG. 20 provides a model of the impedances encountered in FIG. 19. As mentioned previously, measuring the voltage signal developed across the tissue provides at least the following impedances: delivery electrode impedance $Z_e$ (related to the interface of the energy delivery body 108 with local tissue LT), local tissue impedance $Z_{LT}$, internal body tissue impedance $Z_{BT}$, skin impedance, $Z_S$, and the dispersive electrode impedance $Z_{de}$ (related to the interface of the dispersive electrode 140 and skin S). Measuring the voltage signal at the first reference electrode 200*a* provides a reference electrode impedance $Z_{re}$, which can account for the delivery electrode impedance $Z_e$. Measuring the voltage signal at the second reference electrode 200*b* provides a reference electrode impedance $Z_{re'}$, which can account for the delivery electrode impedance $Z_e$. Consequently, performed measurements will be insensitive to the impedance at the therapeutic electrode interface $Z_e$, thus, increasing the sensitivity of the performed measurements to changes at the local tissue.

It may be appreciated that although the featured embodiments involve monopolar energy delivery, at least some of the devices, systems and methods described herein may be utilized in bipolar energy delivery. In particular, the use of the reference electrode 200 and generation of the IBI values may alternatively be of use when delivering energy in a bipolar arrangement.

Implementation of Impedance-Based Indicator

The impedance-based indicator (IBI) can be used in a variety of ways. For example, IBI values can be used during treatment, such as to monitor progress, ensure completeness of treatment and/or to provide feedback that may be used to alter the treatment protocol (either manually or automatically), to name a few. Likewise, the IBI values may be used to record the treatment for historical recordation or future analysis. In some embodiments, the IBI values are used to improve the generation of the IBI values, such as via machine learning algorithms.

As mentioned previously, in some embodiments, the generator 104 includes a user interface 150 that can include a touch screen and/or more traditional buttons to allow for the operator to enter patient data, select a treatment algorithm (i.e., energy delivery algorithm 152), initiate energy delivery, view records stored on the storage/retrieval unit 156, or otherwise communicate with the generator 104. In some embodiments, the generator 104 includes a display 500. Such a display 500 may be integral with the user interface 150 (e.g., touchscreen) or may be separate (e.g., display screen). In either case, it may be appreciated that the display 500 may be separate from the generator 104 but in communication with the generator 104 and/or other apparatuses.

Figure 21:
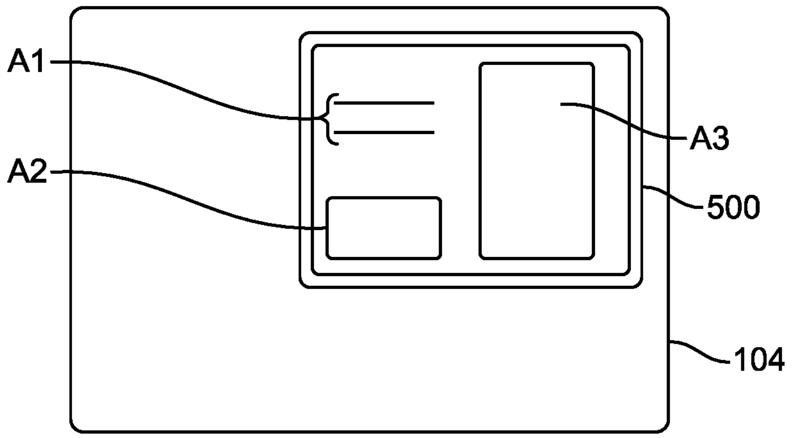
FIG. 21 illustrates a generator having a display which includes various areas for displaying information or data.

FIG. 21 illustrates a generator 104 having a display 500. In this embodiment, the display 500 includes various areas for displaying information or data. For example, in some embodiments, the display 500 includes an area A1 for displaying target information, such as organ type (e.g., heart, lung, cervix, etc.), tissue type (e.g., endothelial cells, myocardium, etc.), disease type (e.g., chronic bronchitis, asthma, atrial fibrillation, etc.), and/or treatment target depth (e.g., 0.1 mm, 0.5 mm, 1 mm, 2 mm, etc.), to name a few. Typically, such information is static and is pre-programmed or programmable, such as via the user interface 150. In some embodiments, such information is used to select a treatment algorithm 152.

In some embodiments, the display 500 includes an area A2 for waveform information, such as voltage, frequency, treatment duration, packet number, etc. In some embodiments, such information is static and is pre-programmed or programmable, such as via the user interface 150. In some embodiments, such information is used to generate a treatment waveform and/or select a treatment algorithm 152. In other embodiments, the user selects a particular treatment algorithm 152, such as from choices displayed in area A2. In some embodiments, at least a portion of the information is dynamic, such as including a packet counter which displays the number of packets delivered real-time during the treatment.

Figure 22A:
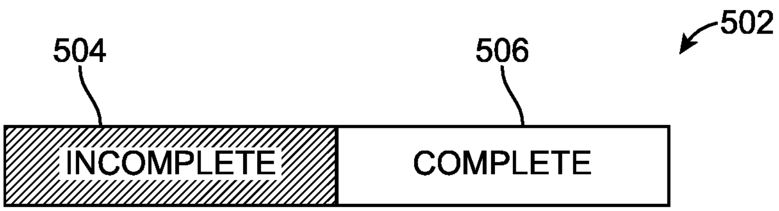
FIGS. 22A-22B illustrate an example of a completion indicator.
Figure 22B:
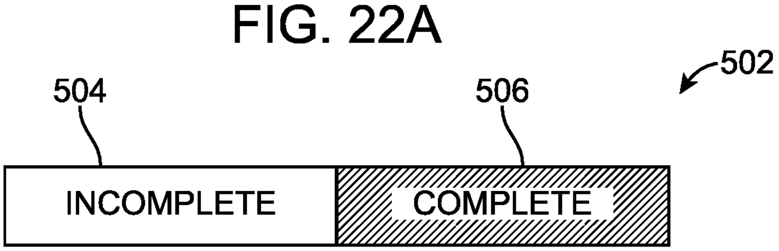

In some embodiments, the display includes an area A3 for progress information. In some embodiments, the progress information utilizes an impedance-based indicator (IBI), such as measured at various times throughout the treatment protocol. Since the IBI indicates condition of the tissue, it can convey how close the tissue is to being fully treated and when full treatment has been reached. Thus, an IBI value is established that correlates to complete treatment of the tissue. This IBI value is pre-programmed or determined based on inputted information from the user. In some embodiments, a completion indicator 502 is provided on the display 500 that simply indicates when completion of the treatment has been achieved at a particular target tissue site. FIGS. 22A-22B illustrate an example of a completion indicator 502 comprising a first portion 504 labeled "incomplete" that illuminates during the treatment prior to completion of the treatment (FIG. 22A). The indicator 502 also includes a second portion 506 labeled "complete" that illuminates once the treatment has been completed (FIG. 22B). Typically, the transition from incomplete to complete is based on reaching a predetermined IBI value. However, it may be appreciated that other measurements may be used in determining the transition. It may also be appreciated that the indictor 502 may be comprised of a single portion that illuminates upon completion of the treatment. However, in some instances it is desired to provide feedback to the user during the treatment leading up to completion by the illumination of the "incomplete" label. It may also be appreciated that other types of labels may be used or other types of indications, such as color illumination or sound.

Figure 23:
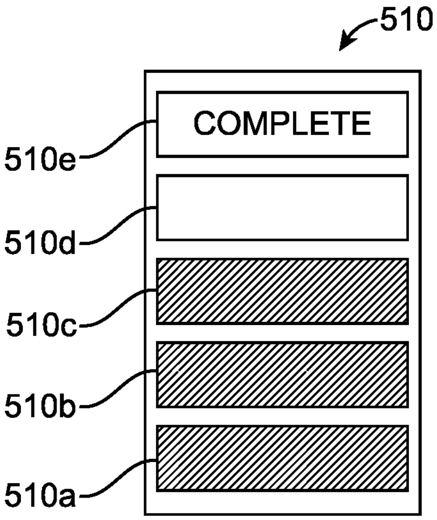
FIG. 23 illustrates an example of a progress indicator.
Figure 24:
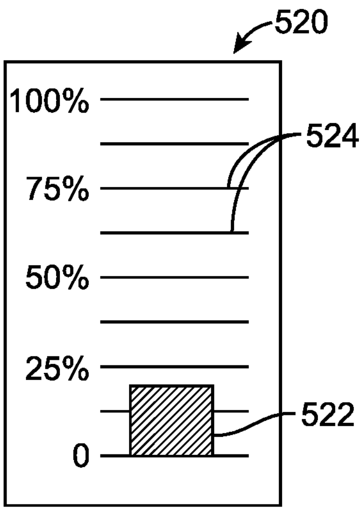
FIG. 24 illustrates a bar graph providing a real-time graphical visualization of progress.

In other embodiments, real-time progress of the treatment is conveyed by a progress indicator 510, such as illustrated in FIG. 23. In this embodiment, the indicator 510 comprises a series of portions that are illuminable as the treatment progresses. For example, in this embodiment, the indicator 510 comprises five illuminable portions (510*a*, 510*b*, 510*c*, 510*d*, 510*e*). Each portion has a threshold at which it is illuminated based on the status of the treatment. In some embodiments, the thresholds are correlated to IBI values. As the treatment progresses, the target tissue is evaluated at various time points generating IBI values over time. IBI values are expected to increase as treatment progresses. Each time a measured/generated IBI value crosses a threshold IBI value, the correlating portion of the indicator 510 is illuminated. As an example, FIG. 23 illustrates a treatment scenario wherein the target tissue has been treated to an extent wherein the measured IBI values have exceeded the thresholds for the first three portions 510*a*, 510*b*, 510*c*, thereby illuminating those portions. The last portion 510*e* indicates completion and it will be illuminated when the measured IBI value meets the threshold for completion. In other embodiments, progress is indicated by a real-time graphical visualization 520, such as including a bar graph 522 as illustrated in FIG. 24. In this embodiment, the bar graph 522 incrementally increases in size throughout the progression of the treatment. Typically, the visualization 520 includes various threshold indicators 524 to provide context to the user as to how the size of the bar graph 522 correlates to completion of the treatment (e.g., 25% completion, 50% completion, 75% completion, 100% completion). It may be appreciated that typically the thresholds are correlated to IBI values. As the treatment progresses, the target tissue is evaluated at various time points generating IBI values over time. Each time a measured IBI value crosses the next threshold IBI value, the bar graph 522 raises to the next level. It may be appreciated that any number of threshold indicators 524 may be provided and the bar graph 522 may increase gradually or in steps.

In some embodiments, one or more measured IBI values are provided to the user throughout the treatment in number form. For example, FIG. 25 illustrates a scrolling display 530 of IBI values (e.g., 0.62, 0.65, 0.79, 0.81, 0.85, etc.) that the user can utilize to determine the progress and rate of progression of the treatment. In some instances, the user is familiar with the desired IBI value(s) and can simply monitor the flow of measurements. In other instances, a look up chart is provided to assist in correlating the IBI values to known tissue status. It may be appreciated that any suitable number of historical IBI values may be provided at any given time. Likewise, it may be appreciated that a single IBI value may be provided, such as illustrated in FIG. 26, without historical values. In such embodiments, the single IBI value changes during the procedure so that the user is able to see the most recently measured IBI value. It may be appreciated that progression information can be provided in forms other than IBI values. For example, FIG. 27 illustrates progress provided as a numerical percentage of completion that changes over time. Likewise, FIG. 28 illustrates progress provided as depth of penetration of the treatment. Thus, in some embodiments, the measured IBI value is correlated to depth of tissue penetration and the penetration depth is provided to the user (such as in millimeters or another unit of measure).

In some embodiments, the treatment progress is provided to the user over multiple treatments, such as illustrated in FIG. 29. For example, when treating a lung passageway, treatment may be provided at a series of target locations along the passageway so as to treat a length of the passageway. In some embodiments, treatment progress is provided during an application of energy to a first target location along the passageway. Then the device is moved along the passageway to provide energy to a second target location, typically adjacent or overlapping with the first target location. Treatment progress can then be provided during application of energy to the second target location. This continues for as many treatment locations as desired. FIG. 29 illustrates a series of treatment bar graphs 550*a*, 550*b*, 550*c* that each approach an IBI threshold indicating completion of each individual treatment. Thus, the first bar graph 550*a* incrementally increases in size throughout the progression of the treatment at the first treatment location. Once completion has been reached, energy is delivered to the second treatment location. The second bar graph 550*b* incrementally increases in size throughout the progression of the treatment at the second treatment location. Likewise, once completion has been reached, energy is delivered to the third treatment location. The third bar graph 550*c* incrementally increases in size throughout the progression of the treatment at the third treatment location. Thus, the user is able to track the progress of each of the treatments over time.

It may be appreciated that progress other than completion of treatment may be tracked. For example, a variety of thresholds may be set, each indicating a status of interest. Example statuses include various depths of penetration, various effects on cells (e.g., reversible modification, permanent cell death, etc.) and others. FIG. 30 illustrates a series of a treatment bar graph 560 approaching a plurality of thresholds 562*a*, 562*b*, 562*c*. Such thresholds may be set by known IBI values and as the treatment progresses, measured IBI values can be displayed via the growing bar graph 560 in relation to the thresholds 562*a*, 562*b*, 562*c*. Once the desired threshold has been reached, the user can stop treatment or move on to the next treatment location. Likewise, it may be appreciated that the treatment may be automatically ceased based on measured IBI values, such as once completion or a desired threshold has been reached.

Figure 31:
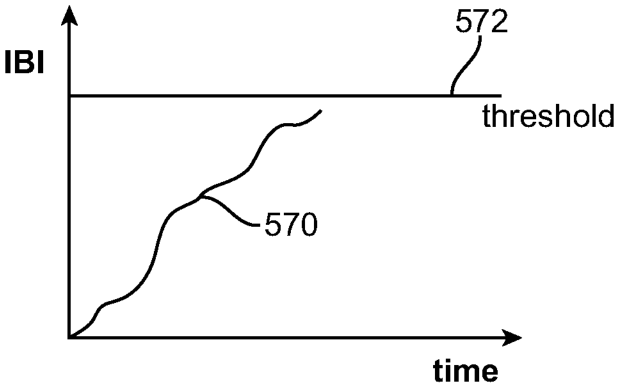
FIG. 31 illustrates progress status conveyed as a line graph.
Figure 32:
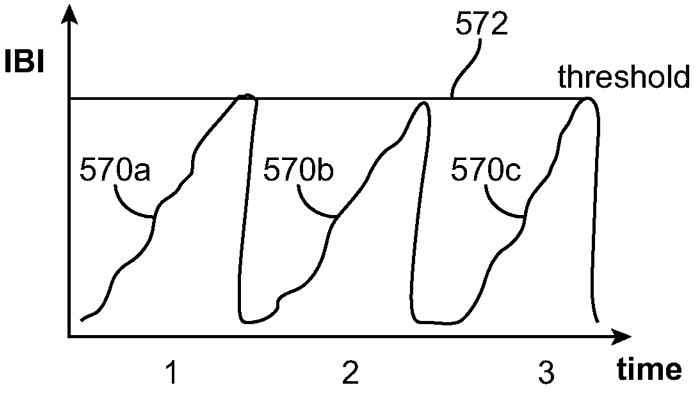
FIG. 32 illustrates treatment progress conveyed as a line graph over multiple treatments.

In some embodiments, progress status is conveyed in other formats, such as a line graph. FIG. 31 illustrates measured IBI values during a treatment protocol. Thus, a line 570 indicating IBI values progresses over time. Such a line 570 is typically provided real-time so the user can track the progress of the treatment. As illustrated, the line 570 approaches a threshold 572, such as a particular effect or treatment completion, so that the user can anticipate and visualize fulfillment of the goal. It may be appreciated that the treatment progress may be provided to the user over multiple treatments, such as illustrated in FIG. 32. Here, the line graph continues over multiple treatments. For example, a first segment of the line 570*a* incrementally approaches the threshold throughout the progression of the treatment at the first treatment location. Once the threshold 572 has been reached, energy is delivered to the second treatment location, starting again at baseline. The second portion of the line 570*b* incrementally increases throughout the progression of the treatment at the second treatment location. Likewise, once completion has been reached, energy is delivered to the third treatment location. The third portion of the line 570*c* incrementally increases throughout the progression of the treatment at the third treatment location. Thus, the user is able to track the progress of each of the treatments over time.

Figure 33:
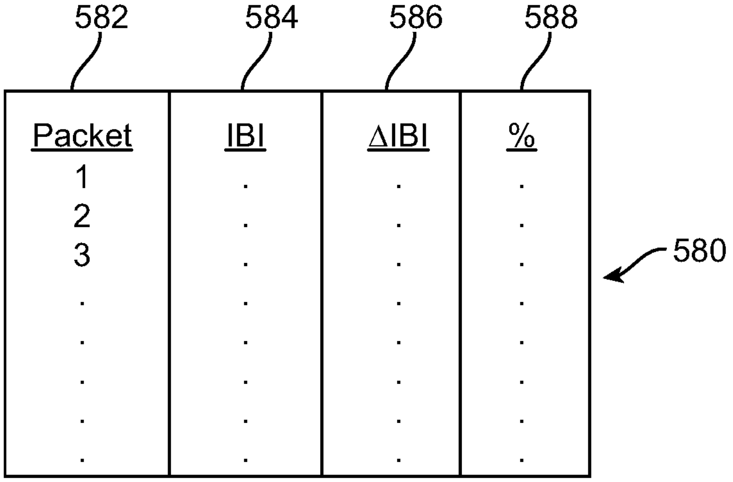
FIG. 33 illustrates a table displayed so as to provide a variety of treatment information.

In some embodiments, a table 580 is displayed providing a variety of treatment information, such as illustrated in FIG. 33. In this embodiment, the table 580 includes packet number 582, corresponding IBI value 584, change in IBI value from previous measurement 586, and percent of progress made toward completion 588 (e.g., based on IBI values). The values in the table typically update real-time to allow the user to track the progress of the treatment.

It may be appreciated that the information provided to the user, such as via the display 500 (e.g., target information, waveform information, progress information, etc.) may be utilized in a variety of ways. For example, the information may be utilized even before treatment begins to ensure that the proper treatment area has been selected, particularly when treating multiple tissue areas in a treatment protocol. For instance, in some embodiments, one or more test signals (e.g., very low voltage such as 100 volts) are delivered so as to generate at least one IBI value which may be utilized to determine if the treatment area was previously treated, and optionally to what extent it was treated. In some embodiments, a determination of previous completed treatment prevents the generator 104 or other devices in the system from delivering the treatment energy to the previously treated area. Optionally, the user may reposition the energy delivery body 108 to a new treatment location. The amount the user repositions the energy delivery body 108 may be based on the percent confidence of prior treatment overlap (e.g., as indicated by IBI), such a 70% overlap, 20% overlap, etc. For example, if the IBI indicates a 50% reduction in expected IBI gain from the testing signal, the user may assume that the energy delivery body 108 is overlapping a previously treated site by half the length of the energy delivery body 108 contact distance and thus would over the energy delivery body 108 by an additional half the length of the energy delivery body 108 in a direction away from the prior treatments. In some embodiments, the user may aim to have a small degree of overlap of treatment areas. In such embodiments, the user may target placements of the energy delivery body 108 where the IBI indicates a small degree of overlap (e.g., 5%, 10%, 20%). This may assist in creating a contiguous treatment area without excessive unnecessary regions of treatment area overlap. This method may reduce overtreatment and/or undesired collateral tissue effects which may be dangerous or simply not accrue meaningful clinical benefits.

In other embodiments, the information may be provided to the user as assurance that the treatment is set up and progressing as desired. For example, the user may be able to anticipate next steps in the procedure and anticipate when completion will be reached. Likewise, the provided information may be utilized by the user to interfere or alter the treatment during progression, such as if the treatment is not progressing as desired or has encountered an error. The user may then make changes to the devices and/or treatment to attain the desired affects (e.g., increase or decrease the voltage, add additional packets to the treatment plan, halt delivery of remaining packets in the treatment plan, adjust electrode placement, select a new algorithm, etc.). In some embodiments, the information triggers one or more alarm systems to assist in notifying the user of an undesired situation. Likewise, in some embodiments, the information triggers an automatic shutdown or other safety measures.

It may also be appreciated that the information provided to the user via the display 500 (and/or other progress information) may be automatically utilized by the generator 104 to alter the treatment during the treatment protocol. Thus, the information may act as a feedback loop to adjust the treatment parameters throughout the treatment.

Likewise, the information may be used in machine learning to improve the ability of the generator 104 to provide useful progress information and optionally automatic altering of the treatment protocol. In such situations, the information is typically recorded and correlated with treatment outcomes (e.g., areas of potential or real undertreatment, overtreatment, etc.). These analyses could be used to establish and/or strengthen the predictive abilities of the IBI values thus building in an iterative and evolving utility to the IBI as the data sets continue to expand. The recorded data could also be utilized by the user to summarize the procedure and detect tissue areas that may benefit from retreatment or closer follow up.

It may be appreciated that the devices, systems and methods described herein may be used with a variety of monopolar energy delivery systems and is not limited to the pulmonary tissue modification systems 100 described herein. Example alternative systems include, but are not limited to, those described in PCT/US2020/066205 filed Dec. 18, 2020 entitled, "TREATMENT OF CARDIAC TISSUE WITH PULSED ELECTRIC FIELDS" and in PCT/US2020/028844 filed Apr. 17, 2020 entitled, "DEVICES, SYSTEMS AND METHODS FOR THE TREATMENT OF ABNORMAL TISSUE", both of which are incorporated by reference for all purposes. It may be appreciated that in some embodiments, the systems and devices described herein are when treating tissue in or near a luminal structure such as a blood vessel, an esophagus, a stomach, a pancreatic duct, a biliary duct, a small intestine, a large intestine, a colon, a rectum, a bladder, a urethra, a urinary collecting duct, a uterus, a vagina, a fallopian tube, a ureter, a renal tubule, a spinal canal, a spinal cord, an airway, a nasal cavity, a mouth, a heart chamber, a heart lumen, a kidney lumen, and/or an organ lumen. Endoluminal access allows treatment of target tissue from within various lumens in the body. Lumens are the spaces inside of tubular-shaped or hollow structures within the body and include passageways, canals, ducts and cavities to name a few. Example luminal structures include blood vessels, esophagus, stomach, small and large intestines, colon, bladder, urethra, urinary collecting ducts, uterus, vagina, fallopian tubes, ureters, kidneys, renal tubules, spinal canal, spinal cord, and others throughout the body, as well as structures within and including such organs as the lung, heart and kidneys, to name a few. In some embodiments, the target tissue is accessed via a nearby luminal structure. In some instances, an energy delivery device is advanced through various luminal structures or branches of a luminal system to reach the target tissue location. For example, when accessing a target tissue site via a blood vessel, the energy delivery device may be inserted remotely and advanced through various branches of the vasculature to reach the target site. Likewise, if the luminal structure originates in a natural orifice, such as the nose, mouth, urethra or rectum, entry may occur through the natural orifice and the energy delivery device is then advanced through the branches of the luminal system to reach the target tissue location. Alternatively, a luminal structure may be entered near the target tissue via cut-down or other methods. This may be the case when accessing luminal structures that are not part of a large system or that are difficult to access otherwise.

It may be appreciated that a variety of anatomical locations may be treated endoluminally with the systems and methods described herein. Examples include luminal structures themselves, soft tissues throughout the body located near luminal structures and solid organs accessible from luminal structures, including but not limited to liver, pancreas, gall bladder, kidney, prostate, ovary, lymph nodes and lymphatic drainage ducts, underlying musculature, bony tissue, brain, eyes, thyroid, etc. It may also be appreciated that a variety of tissue locations can be accessed percutaneously or by other methods.

Target tissue cells may be treated in any location throughout the body, including cells of the digestive system (e.g. mouth, glands, esophagus, stomach, duodenum, jejunum, ileum, intestines, colon, rectum, liver, gall bladder, pancreas, anal canal, etc.), cells of the respiratory system (e.g. nasal cavity, pharynx larynx, trachea, bronchi, lungs, etc.), cells of the urinary system (e.g. kidneys, ureter, bladder, urethra, etc.), cells of the reproductive system (e.g. reproductive organs, ovaries, fallopian tubes, uterus, cervix, vagina, testes, epididymis, vas deferens, seminal vesicles, prostate, glands, penis, scrotum, etc.), cells of the endocrine system (e.g. pituitary gland, pineal gland, thyroid gland, parathyroid gland, adrenal gland), cells of the circulatory system (e.g. heart, arteries, veins, etc.), cells of the lymphatic system (e.g. lymph node, bone marrow, thymus, spleen, etc.), cells of the nervous system (e.g. brain, spinal cord, nerves, ganglia, etc.), cells of the muscular system, and cells of the skin, to name a few.

It may be appreciated that the devices, systems and methods described herein may be particularly suitable for treating patients wherein direct visualization of treatment effects or real-time monitoring of depth or volume of treatment cannot be adequately and accurately interpreted by direct visualization or typical imaging modalities. This is especially true for applications of PEFs where cell death is not the targeted objective of the therapy, such as treatments involving uptake of agents or genes.

For example, in some embodiments a subtler, calibrated change may be observed, monitored or measured and compared to a previously determined metric or a metric established by first testing the system in the patient for their specific setup (their baseline impedance profile, absolute values, etc.). In other embodiments, monitoring of IBI/imaginary impedance differences is undertaken to see if they occur and then to see if they resolve, such as over the course of ms, sec, or 10s of secs. In some embodiments, treatment continues until the values do not resolve back to the same level. In still other embodiments, additional (such as a 3rd) frequency(ies) may be used wherein monitoring is undertaken to observe how they all change respective of each other. Thus, it may be appreciated that any number (or continuous) evaluation of frequencies may be used, and additional patterns from the multiple comparisons can be used, to provide even more granular information regarding treatment progression. For example, in some embodiments, monitoring 1 kHz v. 100 kHz may indicate cell death, but changes in the spread between 50 kHz v. 100 kHz may provide insight to other phenomena, including reversible effects on cells.

It may be appreciated that in some embodiments the dispersive electrode and/or the reference electrode may be located within the patient rather than on a surface of the patient's skin. For example, in some embodiments, the dispersive electrode and/or reference electrode are in the form of or are located on a needle. For example, one or more small subcutaneous needles may be used. Similarly, the dispersive electrode and/or reference electrode may be placed onto or into tissue of a patient through a procedure, such as a laparoscopic or open procedure. For another example, the dispersive electrode and/or reference electrode may be placed on or near a distal end of a bronchoscope (e.g., 112 in FIG. 1) or an introducer sheath that is used to introduce a catheter shaft (e.g., 106 in FIG. 1) into a body lumen.

Figure 34:
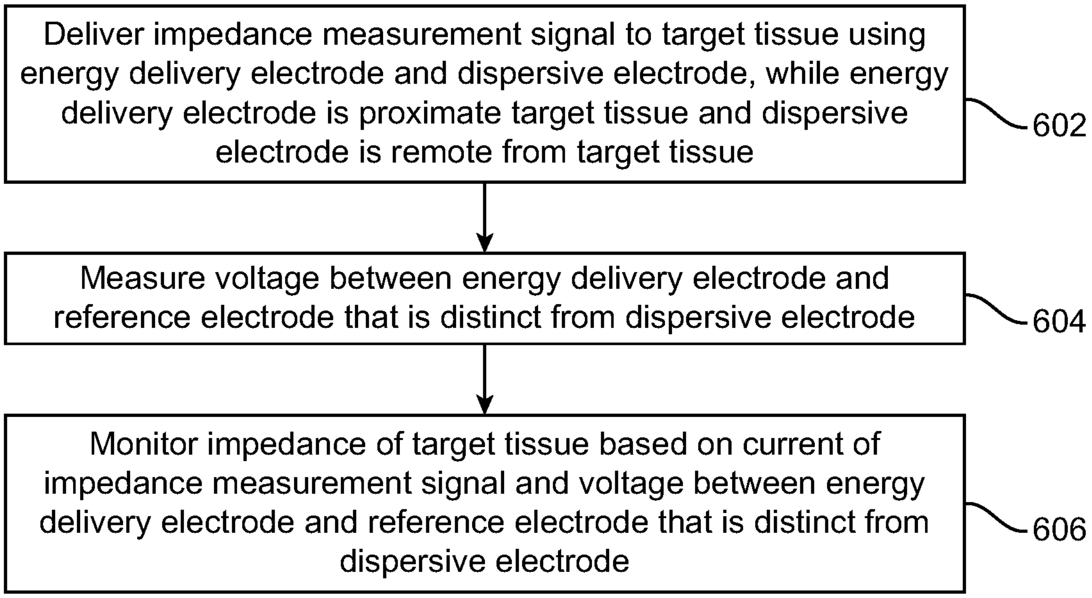
FIGS. 34 and 35 are high level flow diagrams used to summarize methods according to certain embodiments of the present technology.
Figure 35:
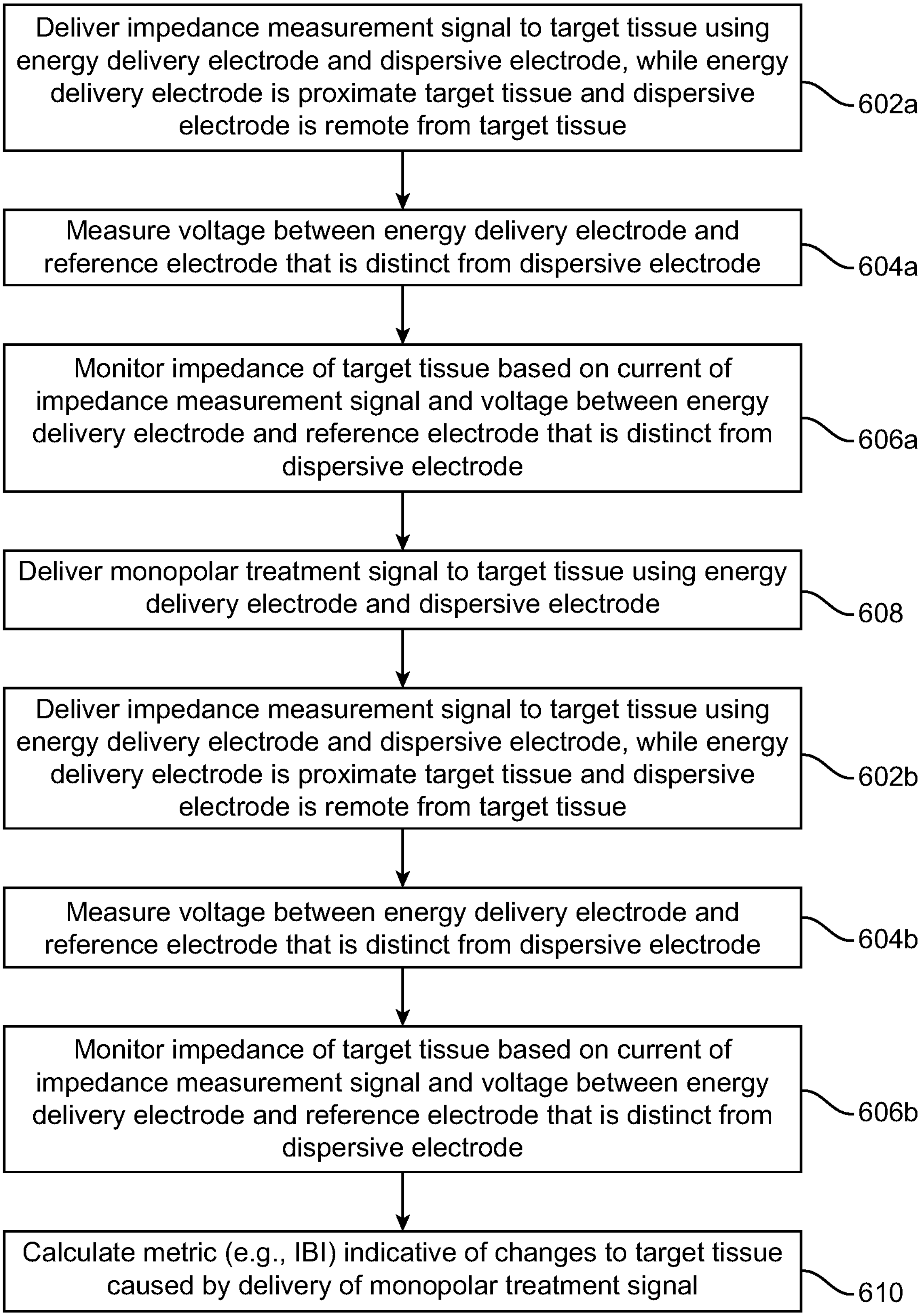

FIGS. 34 and 35 are high level flow diagrams used to summarize methods according to certain embodiments of the present technology, which were introduced above. More specifically, the methods summarized with reference to FIGS. 34 and 35 are for use with a monopolar treatment delivery system (e.g., 100) that is configured to use an energy delivery electrode (e.g., 108) and a dispersive electrode (e.g., 140) to deliver a monopolar treatment signal to target tissue of a patient (e.g., P). As will be appreciated from the below discussion, such a method can be used to deduce a treatment effect outcome resulting from delivery of the monopolar treatment signal.

Referring to FIG. 34, step 602 involves delivering an impedance measurement signal to the target tissue using the energy delivery electrode and the dispersive electrode, while the energy delivery electrode is proximate to the target tissue and the dispersive electrode is remote from the target tissue. Step 604 involves measuring a voltage between the energy delivery electrode and a reference electrode (e.g., 200) that is distinct from the dispersive electrode (e.g., 140). Step 606 involves monitoring an impedance of the target tissue based on a current of the impedance measurement signal and the voltage between the energy delivery electrode and the reference electrode that is distinct from the dispersive electrode. The current of the impedance measurement signal can measured directly (e.g., using an amp meter, or the like). Alternatively, the current of the impedance measurement signal can be measured indirectly, e.g., by measuring a voltage drop across a resistor having a known resistance, and calculating the current using Ohms law (e.g., I=V/R). Alternatively, the current can be known because it is controlled using a controlled current source, or the like. An example of the impedance measurement signal is shown in and discussed above with reference to FIG. 10. As was described above with reference to FIG. 10, in accordance with certain embodiments, the impedance measurement signal includes a low frequency portion and a high frequency portion, wherein the low frequency portion of the impedance measurement signal temporally precedes the high frequency portion of the impedance measurement signal (as shown in FIG. 10), or vice versa.

Referring now to FIG. 35, in accordance with certain embodiments, a first instance of the delivering the impedance measurement signal to the target tissue, a first instance of the measuring the voltage between the energy delivery electrode and the reference electrode, and a first instance of the monitoring the impedance of the target tissue (which first instances of these steps are labeled 602*a*, 604*a*, and 606*a* in FIG. 35), are performed prior to a monopolar treatment signal being delivered to the target tissue using the energy delivery electrode and the dispersive electrode, to thereby enable a baseline impedance measurement to be obtained (at step 606*a*).

Following the baseline impedance measurement being obtained, the method further comprises, at step 608, delivering the monopolar treatment signal to the target tissue using the energy delivery electrode and the dispersive electrode. Thereafter, following the monopolar treatment signal being delivered to the target tissue, the method comprises a second instance of the delivering the impedance measurement signal to the target tissue, a second instance of the measuring the voltage between the energy delivery electrode and the reference electrode, and a second instance of the monitoring the impedance of the target tissue (which second instances of these steps are labeled 602*b*, 604*b*, and 606*b* in FIG. 35), to thereby enable a post-treatment impedance measurement to be obtained (at step 606*b*).

In accordance with certain embodiments, the method can include calculating, based on both the baseline impedance measurement and the post-treatment impedance measurement, a metric indicative of changes to the target tissue caused by the delivery of the monopolar treatment signal, at step 610. More specifically, in accordance with certain embodiments, the metric indicative of changes to the target tissue caused by the delivery of the monopolar treatment signal comprises an impedance-based indicator (IBI). Calculating the IBI includes calculating a difference between a post-treatment low frequency impedance phase angle value measurement $\angle Z_{LF}(t)$ measured at a time t after the monopolar treatment signal has been delivered, and a baseline low frequency impedance phase angle value measurement $\angle Z_{LF}(0)$ measured at a time t=0 prior to the monopolar treatment signal being delivered, and calculating the IBI based on the difference between the post-treatment low frequency impedance phase angle value measurement $\angle Z_{LF}(t)$ and the baseline low frequency impedance phase value measurement $\angle Z_{LF}(0)$.

In accordance with certain embodiments, at least one of baseline impedance measurement and the post-treatment impedance measurement includes a high frequency impedance magnitude value $Z_{HF}$, which is used as a scaling factor. In certain such embodiments, the difference between the post-treatment low frequency impedance phase value measurement $\angle Z_{LF}(t)$ and the baseline low frequency impedance phase value measurement $\angle Z_{LF}(0)$ is scaled by the high frequency impedance magnitude value $Z_{HF}$ when calculating the impedance-based indicator (IBI). More specifically, in accordance with certain embodiments, the IBI is calculated using the following equation:

$$IBI=(\angle Z_{LF}(t)-\angle Z_{LF}(0))\cdot|Z_{HF}|,$$

where $\angle Z_{LF}(0)$ is a low frequency impedance phase angle value measured at a time t=0 prior to the monopolar treatment signal being delivered, $\angle Z_{LF}(t)$ is a low frequency impedance phase angle value measured at a time t after the monopolar treatment signal has been delivered, and $Z_{HF}$ is a high frequency impedance magnitude value measured prior to or after the monopolar treatment signal has been delivered.

In accordance with certain embodiments, the monopolar treatment signal comprises a pulsed electric field (PEF) treatment signal. Alternatively, the monopolar treatment signal can be a radio frequency (RF) treatment signal, a microwave treatment signal, a cryogenic treatment signal, an electrochemical treatment signal, or a high frequency ultrasound signal. Other variations are also possible, and within the scope of certain embodiments described herein.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A monopolar treatment delivery system configured to utilize multiple electrodes to deduce tissue properties at a target tissue, the system comprising:

an energy delivery electrode;

a dispersive electrode;

a reference electrode; and a generator in electrical communication with the energy delivery electrode, the dispersive electrode, and the reference electrode, the generator configured to:

deliver a first impedance measurement signal to the target tissue using the energy delivery electrode and the dispersive electrode, while the energy delivery electrode is proximate to the target tissue and the dispersive electrode is remote from the target tissue;

measure a first voltage between the energy delivery electrode and the reference electrode;

monitor a first impedance of the target tissue based on a current of the first impedance measurement signal and the first voltage between the energy delivery electrode and the reference electrode;

deliver a second impedance measurement signal to the target tissue using the energy delivery electrode and the dispersive electrode, while the energy delivery electrode is proximate to the target tissue and the dispersive electrode is remote from the target tissue;

measure a second voltage between the energy delivery electrode and the reference electrode;

monitor a second impedance of the target tissue based on a current of the second impedance measurement signal and the second voltage between the energy delivery electrode and the reference electrode; and determine a metric indicative of properties of the target tissue based on the first and second impedances.

2. The system of claim 1, wherein the generator is configured to measure the current of the first and second impedance measurement signals directly or indirectly, or to control the current of the first and second impedance measurement signals.

3. The system of claim 1, wherein each of the impedance measurement signals includes a low frequency portion and a high frequency portion that temporally precedes or follows the other.

4. The system of claim 1, wherein the generator is configured to:

deliver a monopolar treatment signal to the target tissue using the energy delivery electrode and the dispersive electrode;

deliver the first impedance measurement signal to the target tissue prior to the monopolar treatment signal being delivered to the target tissue to thereby enable a baseline impedance measurement to be obtained; and deliver the second impedance measurement signal to the target tissue after the monopolar treatment signal is delivered to the target tissue to thereby enable a post-treatment impedance measurement to be obtained.

5. The system of claim 4, wherein the metric is indicative of changes to the target tissue caused by the delivery of the monopolar treatment signal.

6. The system of claim 5, wherein the generator is configured to calculate the metric indicative of changes to the target tissue caused by delivery of the monopolar treatment signal by calculating an impedance-based indicator (IBI), which includes:

calculating a difference between a post-treatment low frequency impedance phase angle value measurement $\angle Z_{LF}(t)$ measured at a time t after the monopolar treatment signal has been delivered, and a baseline low frequency impedance phase angle value measurement $\angle Z_{LF}(0)$ measured at a time t=0 prior to the monopolar treatment signal being delivered; and calculating the IBI based on the difference between the post-treatment low frequency impedance phase angle value measurement $\angle Z_{LF}(t)$ and the baseline low frequency impedance phase value measurement $\angle Z_{LF}(0)$.

7. The system of claim 6, wherein at least one of baseline impedance measurement and the post-treatment impedance measurement includes a high frequency impedance magnitude value $Z_{HF}$, and wherein the generator is configured to scale the difference between the post-treatment low frequency impedance phase value measurement $\angle Z_{LF}(t)$ and the baseline low frequency impedance phase value measurement $\angle Z_{LF}(0)$ by the high frequency impedance magnitude value $Z_{HF}$ when calculating the impedance-based indicator (IBI).

8. The system of claim 5, wherein the generator is configured to calculate the IBI using the following equation:

$$IBI=(\angle Z_{LF}(t)-\angle Z_{LF}(0))\cdot|Z_{HF}|,$$

where $\angle Z_{LF}(0)$ is a low frequency impedance phase angle value measured at a time t=0 prior to the monopolar treatment signal being delivered, $\angle Z_{LF}(t)$ is a low frequency impedance phase angle value measured at a time t after the monopolar treatment signal has been delivered, and $Z_{HF}$ is a high frequency impedance magnitude value measured prior to the monopolar treatment signal being delivered or after the monopolar treatment signal has been delivered.

9. The system of claim 4, wherein the monopolar treatment signal comprises a pulsed electric field (PEF) treatment signal.

10. The system of claim 4, wherein the monopolar treatment signal comprises one of:

a radio frequency (RF) treatment signal;
a microwave treatment signal;
a cryogenic treatment signal;
an electrochemical treatment signal; or
a high frequency ultrasound signal.

11. A method for use with a monopolar treatment delivery system that is configured to use an energy delivery electrode and a dispersive electrode to deliver a monopolar treatment signal to target tissue of a patient, the method comprising:

delivering a first impedance measurement signal to the target tissue using the energy delivery electrode and the dispersive electrode, while the energy delivery electrode is proximate to the target tissue and the dispersive electrode is remote from the target tissue;

measuring a first voltage between the energy delivery electrode and a reference electrode that is distinct from the dispersive electrode; and monitoring a first impedance of the target tissue based on a current of the first impedance measurement signal and the first voltage between the energy delivery electrode and the reference electrode that is distinct from the dispersive electrode;

delivering a second impedance measurement signal to the target tissue using the energy delivery electrode and the dispersive electrode, while the energy delivery electrode is proximate to the target tissue and the dispersive electrode is remote from the target tissue;

measuring a second voltage between the energy delivery electrode and the reference electrode that is distinct from the dispersive electrode;

monitoring a second impedance of the target tissue based on a current of the second impedance measurement signal and the second voltage between the energy delivery electrode and the reference electrode that is distinct from the dispersive electrode; and determining a metric indicative of properties of the target tissue based on the first and second impedances.

12. The method of claim 11, wherein the current of the first and second impedance measurement signals is measured directly or indirectly, or is known because it is controlled.

13. The method of claim 11, wherein:

a first instance of the delivering the first impedance measurement signal to the target tissue, a first instance of the measuring the first voltage between the energy delivery electrode and the reference electrode, and a first instance of the monitoring the first impedance of the target tissue, are performed prior to a monopolar treatment signal being delivered to the target tissue using the energy delivery electrode and the dispersive electrode, to thereby enable a baseline impedance measurement to be obtained;

following the baseline impedance measurement being obtained, the method further comprises delivering the monopolar treatment signal to the target tissue using the energy delivery electrode and the dispersive electrode; and following the delivering the monopolar treatment signal to the target tissue, the method comprises a second instance of the delivering the second impedance measurement signal to the target tissue, a second instance of the measuring the second voltage between the energy delivery electrode and the reference electrode, and a second instance of the monitoring the second impedance of the target tissue, to thereby enable a post-treatment impedance measurement to be obtained.

14. The method of claim 11, wherein:

each of the first and second impedance measurement signals includes a low frequency portion and a high frequency portion; and the low frequency portion of each of the first and second impedance measurement signals temporally precedes the high frequency portion of the impedance measurement signal, or vice versa.

15. The method of claim 14, further comprising:

calculating, based on both a baseline impedance measurement and a post-treatment impedance measurement, a metric indicative of changes to the target tissue caused by the delivery of the monopolar treatment signal.

16. The method of claim 11, wherein the monopolar treatment signal comprises a pulsed electric field (PEF) treatment signal.

17. The method of claim 11, wherein the monopolar treatment signal comprises one of:
a radio frequency (RF) treatment signal;
a microwave treatment signal;
a cryogenic treatment signal;
an electrochemical treatment signal; or
a high frequency ultrasound signal.

18. The method of claim 11 wherein the method is used to deduce a treatment effect outcome resulting from delivery of the monopolar treatment signal.

19. The method of claim 11, wherein the method is performed by at least one processor of a monopolar treatment delivery system, which at least one processor can be part of a controller of the monopolar treatment delivery system.

20. A method for use with a monopolar treatment delivery system that is configured to use an energy delivery electrode and a dispersive electrode to deliver a monopolar treatment signal to target tissue of a patient, the method comprising:
delivering an impedance measurement signal to the target tissue using the energy delivery electrode and the dispersive electrode, while the energy delivery electrode is proximate to the target tissue and the dispersive electrode is remote from the target tissue;
measuring a voltage between the energy delivery electrode and a reference electrode that is distinct from the dispersive electrode;
monitoring an impedance of the target tissue based on a current of the impedance measurement signal and the voltage between the energy delivery electrode and the reference electrode that is distinct from the dispersive electrode, wherein the impedance measurement signal includes a low frequency portion and a high frequency portion, and the low frequency portion of the impedance measurement signal temporally precedes the high frequency portion of the impedance measurement signal, or vice versa; and
calculating, based on both the baseline impedance measurement and the post-treatment impedance measurement, a metric indicative of changes to the target tissue caused by the delivery of the monopolar treatment signal,
wherein the calculating the metric indicative of changes to the target tissue caused by the delivery of the monopolar treatment signal comprises calculating an impedance-based indicator (IBI), which includes:
calculating a difference between a post-treatment low frequency impedance phase angle value measurement $\angle Z_{LF}(t)$ measured at a time t after the monopolar treatment signal has been delivered, and a baseline low frequency impedance phase angle value measurement $\angle Z_{LF}(0)$ measured at a time t=0 prior to the monopolar treatment signal being delivered; and
calculating the IBI based on the difference between the post-treatment low frequency impedance phase angle value measurement $\angle Z_{LF}(t)$ and the baseline low frequency impedance phase value measurement $\angle Z_{LF}(0)$.

21. The method of claim 20, wherein:
at least one of the baseline impedance measurement and the post-treatment impedance measurement includes a high frequency impedance magnitude value $Z_{HF}$; and
the difference between the post-treatment low frequency impedance phase value measurement $\angle Z_{LF}(t)$ and the baseline low frequency impedance phase value measurement $\angle Z_{LF}(0)$ is scaled by the high frequency impedance magnitude value $Z_{HF}$ when calculating the impedance-based indicator (IBI).

22. A method for use with a monopolar treatment delivery system that is configured to use an energy delivery electrode and a dispersive electrode to deliver a monopolar treatment signal to target tissue of a patient, the method comprising:
delivering an impedance measurement signal to the target tissue using the energy delivery electrode and the dispersive electrode, while the energy delivery electrode is proximate to the target tissue and the dispersive electrode is remote from the target tissue;
measuring a voltage between the energy delivery electrode and a reference electrode that is distinct from the dispersive electrode;
monitoring an impedance of the target tissue based on a current of the impedance measurement signal and the voltage between the energy delivery electrode and the reference electrode that is distinct from the dispersive electrode, wherein the impedance measurement signal includes a low frequency portion and a high frequency portion, and the low frequency portion of the impedance measurement signal temporally precedes the high frequency portion of the impedance measurement signal, or vice versa;
calculating, based on both the baseline impedance measurement and the post-treatment impedance measurement, a metric indicative of changes to the target tissue caused by the delivery of the monopolar treatment signal; and
calculating an impedance-based indicator (IBI), wherein the calculating the IBI is performed using the following equation:

$$IBI=(\angle Z_{LF}(t)-\angle Z_{LF}(0))\cdot|Z_{HF}|,$$

where
$\angle Z_{LF}(0)$ is a low frequency impedance phase angle value measured at a time t=0 prior to the monopolar treatment signal being delivered,
$\angle Z_{LF}(t)$ is a low frequency impedance phase angle value measured at a time t after the monopolar treatment signal has been delivered, and
$Z_{HF}$ is a high frequency impedance magnitude value measured prior to or after the monopolar treatment signal has been delivered.

* * * * *